United States Patent
DeGoey et al.

(10) Patent No.: US 7,718,633 B2
(45) Date of Patent: May 18, 2010

(54) PRODRUGS OF HIV PROTEASE INHIBITORS

(75) Inventors: David A. DeGoey, Salem, WI (US); William J. Flosi, Evanston, IL (US); David J. Grampovnik, Waukegan, IL (US); Larry L. Klein, Lake Forest, IL (US); Dale J. Kempf, Libertyville, IL (US); Xiu C. Wang, Green Oaks, IL (US)

(73) Assignee: Abbott Laboratories, Abbott Park, IL (US)

( * ) Notice: Subject to any disclaimer, the term of this patent is extended or adjusted under 35 U.S.C. 154(b) by 806 days.

(21) Appl. No.: 11/170,197

(22) Filed: Jun. 29, 2005

(65) Prior Publication Data

US 2007/0270383 A1 Nov. 22, 2007

Related U.S. Application Data

(60) Provisional application No. 60/585,710, filed on Jul. 6, 2004.

(51) Int. Cl.
C07F 9/09 (2006.01)
A61K 31/661 (2006.01)

(52) U.S. Cl. .............................. 514/86; 514/89; 514/92; 514/100; 544/243; 544/337; 546/22; 546/23; 548/119

(58) Field of Classification Search ................ 544/243, 544/337; 546/22, 23; 548/119; 514/86, 514/89, 92, 100
See application file for complete search history.

(56) References Cited

U.S. PATENT DOCUMENTS

| | | | |
|---|---|---|---|
| 6,204,257 B1 | 3/2001 | Stella et al. | 514/130 |
| 6,559,137 B1 | 5/2003 | Tung et al. | 514/99 |
| 2004/0024031 A1 | 2/2004 | Morissette et al. | |

FOREIGN PATENT DOCUMENTS

| | | |
|---|---|---|
| EP | 0604910 A1 | 7/1994 |
| WO | WO95/07269 | 3/1995 |
| WO | WO03/006506 A2 | 1/2003 |
| WO | WO03/006506 A3 | 1/2003 |

OTHER PUBLICATIONS

Miles, Medline Abstract (Community Pract, vol. 78, Issue 8, pp. 292-294) Aug. 2005.*
van Heeswijk et al., PubMed Abstract (Antivir Ther. 6(4):201-29) Dec. 2001.*
Marcus et al., PubMed Abstract (Intervirology 45(4-6):260-6) 2002.*
Berge, S.M., et al., "Pharmaceutical Salts", *Journ. of Pharm. Sciences*, 66(10):1-19 (1977).
Jacques, et al., "Enantiomers, Racemates, and Resolutions", *Krieger Publ. Co., FL.*, (1981).
Poste, G., et al., "Lipid Vesicles as Carriers for Introducing Biologically Active Materials into Cells", *Methods in Cell Biology*, XIV:33-71 (1976).
International Preliminary Report on Patentability from International Patent Application No. PCT/US2005/023047, (2007).
D. A. DeGoey et al., *Water-Soluble Prodrugs of Lopinavir, Ritonavir and New Investigational HIV PIs*, 234 ACS National Meeting, MEDI-98 (Boston, MA, Aug. 19-23, 2007).
E. S. Furfine et al., *Preclinical Pharmacology and Pharmacokinetics of GW433908, a Water-Soluble Prodrug of the Human Innnunodeficiency Virus Protease Inhibitor Amprenavir*, Antimicrobial Agents and Chemotherapy 48(3):791-8 (2004).
J. Golik et al., *Synthesis and Antitumor Evaluation of Paclitaxel Phosphonooxymethyl Ethers: A Novel Class of Water Soluble Paclitaxel Pro-Drugs*, Bioorganic & Medicinal Chemistry Letters 6(15):1837-42 (1996).
Search Report from European Patent Application No. 05762529.5 (Apr. 29, 2008).
D.A. DeGoey et al., Water-Soluble Prodrugs of the Human Immunodeficiency Virus Protease Inhibitors Lopinavir and Ritonavir, J. Med. Chem. 52 (9):296470 (2009).

* cited by examiner

*Primary Examiner*—Deepak Rao
(74) *Attorney, Agent, or Firm*—Michael J. Ward

(57) ABSTRACT

A compound of the formula

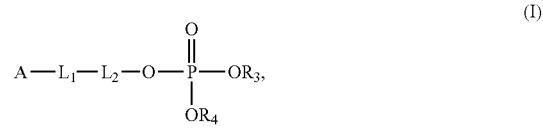

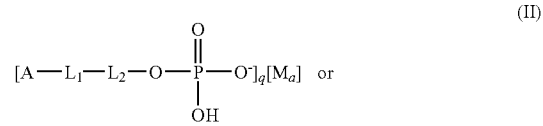

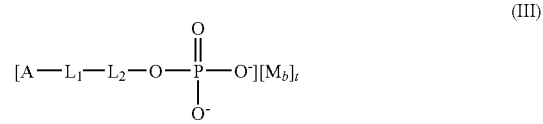

is disclosed as a prodrug of an HIV protease inhibitor. Methods and compositions for inhibiting HIV protease activity and treating HIV infection are also disclosed.

42 Claims, No Drawings

PRODRUGS OF HIV PROTEASE INHIBITORS

This application claims priority to the provisional application Ser. No. 60/585,710 filed on Jul. 6, 2004.

TECHNICAL FIELD

This invention relates to prodrugs of protease inhibitors, in particular, HIV (human immunodeficiency) protease inhibitors, and to the pharmaceutical compositions comprising these prodrugs. This invention also relates to the pharmaceutical compositions and methods of treating HIV (human immunodeficiency virus) infection in mammals with these prodrugs, the processes for making such compounds and synthetic intermediates employed in these processes.

BACKGROUND OF THE INVENTION

HIV protease inhibitors are highly potent agents that inhibit the replication of HIV (human immunodeficiency) viruses and prolong the lives of individuals infected with HIV. Because of the hydrophobic nature of the active site of HIV protease, most HIV protease inhibitors are relatively lipophilic and poorly soluble. Consequently, the delivery of adequate amounts of protease inhibitors to provide antiviral efficacy often requires multiple capsules or tablets. Some protease inhibitors such as ritonavir are not absorbed in the solid state, and often require formulations to solubilize the drug substance.

In addition to being an effective inhibitor of HIV protease, ritonavir is also effective in inhibiting cytochrome P450 monooxygenase. Co-administration of ritonavir with a HIV protease inhibitor that is metabolized by cytochrome P450 monooxygenase often results in improvement in pharmacokinetics (i.e. increased half-life and increased blood levels, particularly increased minimum or trough concentration) of such HIV protease inhibitor. The co-formulated mixture of lopinavir and ritonavir has been shown to be a potent HIV protease inhibitor regimen. Currently, lopinavir/ritonavir is dosed twice daily at 400/100 mg, respectively, co-formulated as a solution in three soft elastic capsules. The three capsules are required because of the limited solubility of lopinavir and ritonavir, and the need for dosing as a solution.

Such solution formulations often result in high pill burdens and poor patient compliance. There is therefore a need for technologies that can provide good oral absorption from formulations with higher drug load per unit dosage.

SUMMARY OF THE INVENTION

The present invention provides novel prodrugs of inhibitors of aspartyl protease, in particular, HIV aspartyl protease. These prodrugs are characterized by excellent aqueous solubility, increased bioavailability and are readily metabolized into the active inhibitors in vivo.

In its principal embodiment, the present invention provides a novel class of prodrugs of HIV aspartyl protease inhibitors having formula (I), (II) or (III)

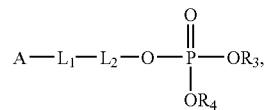
(I)

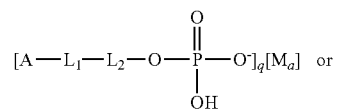
(II)

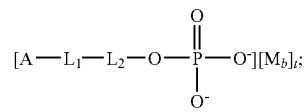
(III)

wherein
$L_1$ is a bond, —C(O)—, or —C(O)O—; wherein the carbonyl of the —C(O)O— moiety is attached to A of formula (I), (II) or (III);
$L_2$ is —(CR$_1$R$_2$)$_m$—,
m is 1, 2, 3, 4 or 5;
$R_1$ at each occurrence is independently selected from the group consisting of hydrogen and $C_1$-$C_{12}$ alkyl;
$R_2$ at each occurrence is independently selected from the group consisting of hydrogen and $C_1$-$C_{12}$ alkyl;
$R_3$ is hydrogen, $C_1$-$C_{12}$ alkyl or arylalkyl;
$R_4$ is hydrogen, $C_1$-$C_{12}$ alkyl or arylalkyl;
q is 1 or 2;
t is 1 or 2;
$M_a$ is $M_1$ or $M_2$;
$M_b$ is $M_1$ or $M_2$;
$M_1$ is Na$^+$, K$^+$ or $^+$N(R$_5$)(R$_6$)(R$_7$)(R$_8$);
$M_2$ is Ca$^{2+}$, Ba$^{2+}$, Mg$^{2+}$, Zn$^{2+}$ or $^+$N(R$_9$)(R$_{10}$)(R$_{11}$)(R$_{12}$),
$R_5$ is hydrogen, alkyl, hydroxyalkyl, arylalkyl or —C(=NH)NH$_2$;
$R_6$ is hydrogen, alkyl, hydroxyalkyl or arylalkyl;
$R_7$ is hydrogen or alkyl;
$R_8$ is hydrogen or alkyl;
alternatively, $R_5$ and $R_6$, together with the nitrogen atom to which they are attached, form a piperidine ring;
$R_9$ is -alkyl-N$^+$(Z$_1$)(Z$_2$)(Z$_3$);
$R_{10}$ is hydrogen, alkyl or arylalkyl;
$R_{11}$ is hydrogen or alkyl;
$R_{12}$ is hydrogen or alkyl;
alternatively, $R_9$ and $R_{11}$, together with the nitrogen atom to which they are attached, form a piperazine ring;
$Z_1$ is hydrogen or alkyl;
$Z_2$ is hydrogen or alkyl;
$Z_3$ is hydrogen, alkyl or arylalkyl; and
A is

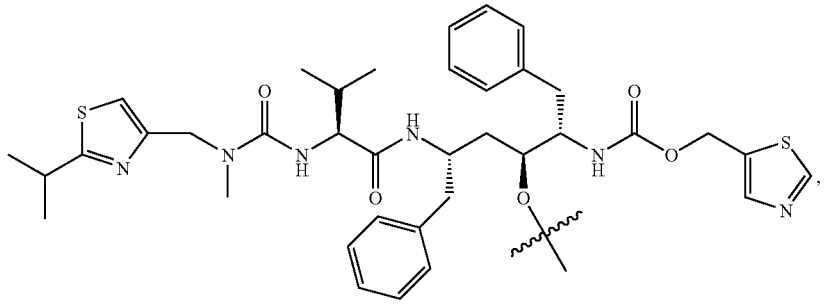
(i)

-continued
(ii)
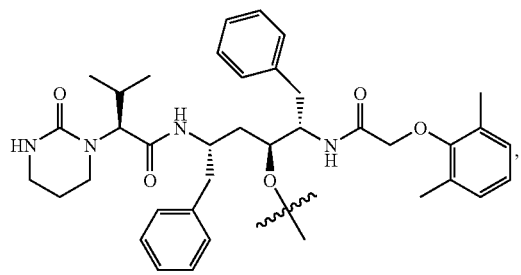
(iii)
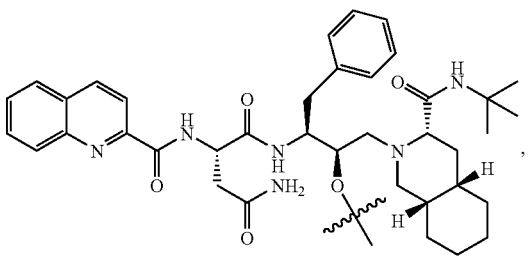
(iv)
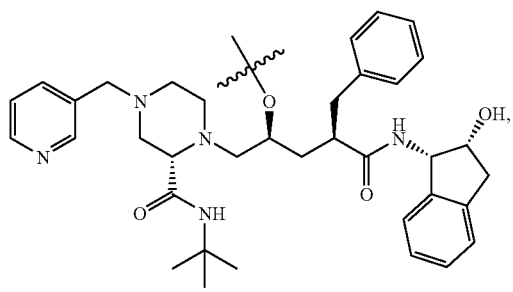
(v)
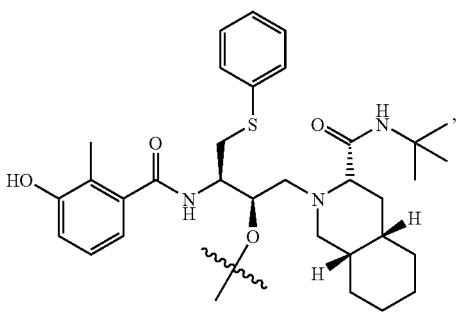
(vi)
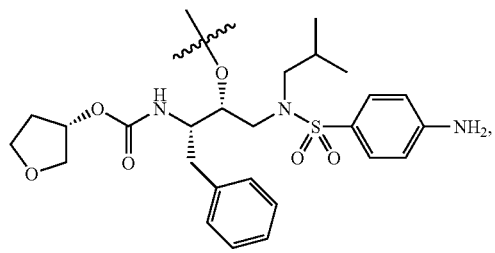
(vii)
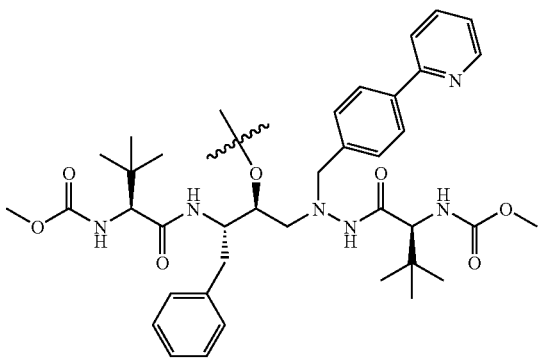
(viii)
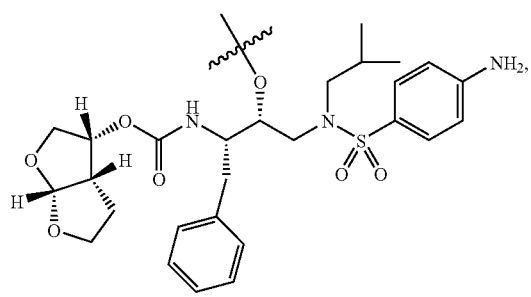
(ix)
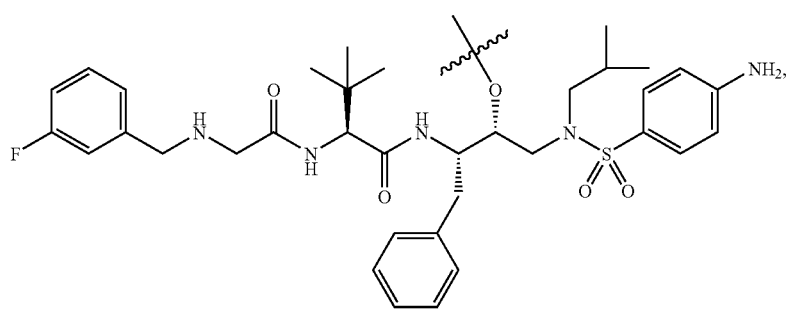

(x)
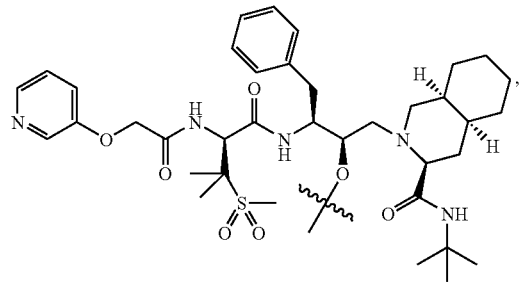
(xi)
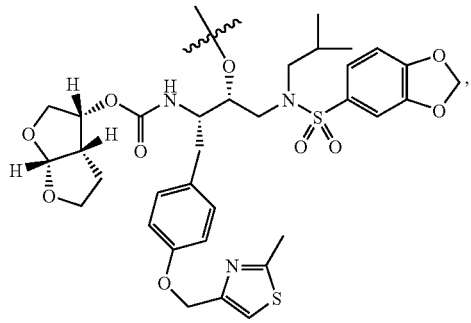
(xii)
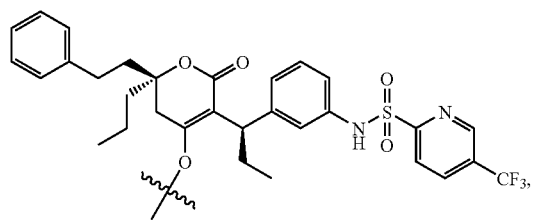
(xiii)
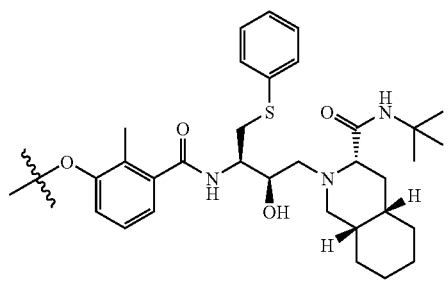
or
(xiv)
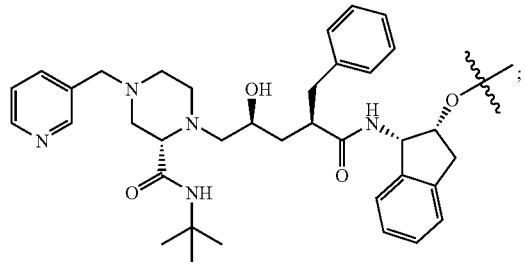
provided that
when q is 1, $M_a$ is $M_1$;
when q is 2, $M_a$ is $M_2$;
when t is 1, $M_b$ is $M_2$;
when t is 2, $M_b$ is $M_1$; and provided that
when A is
(i)
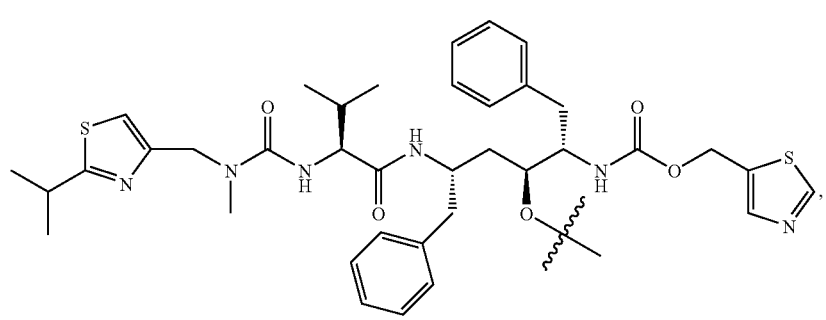

-continued
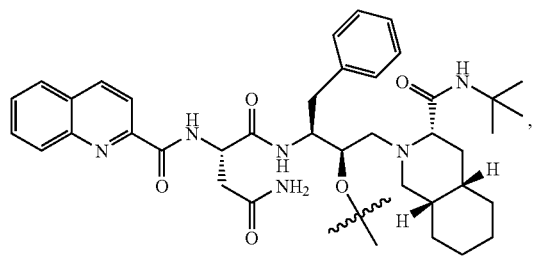
(iii)
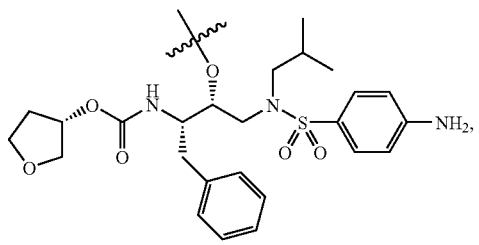
(vi)
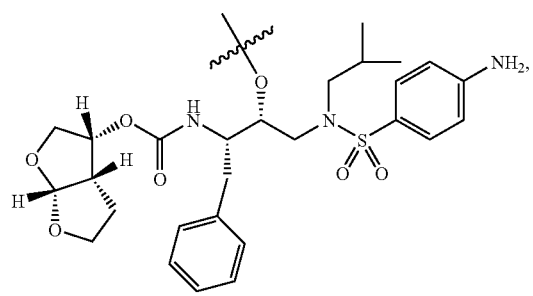
(viii)
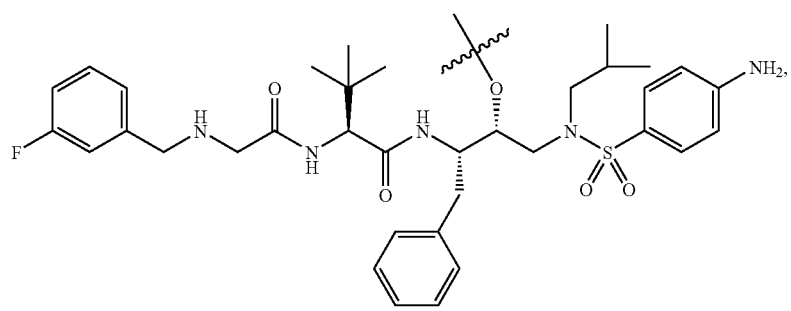
(ix)
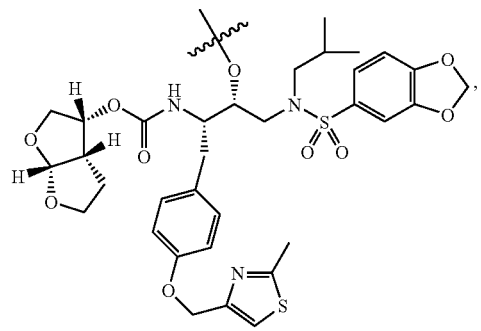
(xi)
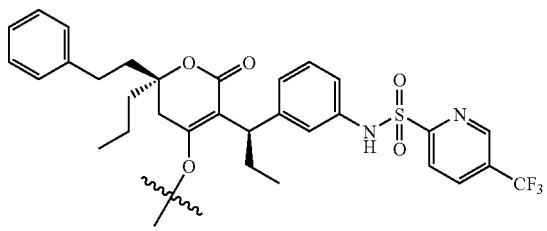
(xii)
or
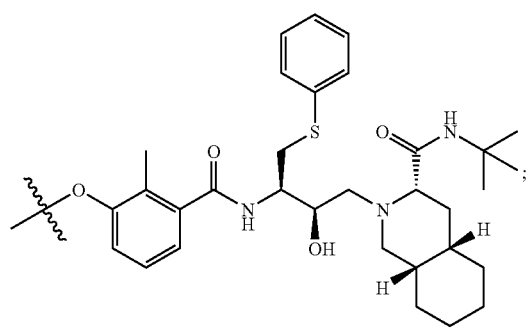
(xiii)
and L$_1$ is a bond, then L$_2$ is not —CH$_2$—.

The present invention also provides pharmaceutical compositions comprising therapeutically effective amount of a compound or combination of compounds of the present invention, and a pharmaceutically acceptable carrier, adjuvant or vehicle.

The compounds of the present invention can be used alone or in combination with other therapeutic agents. As such, the present invention also provides a pharmaceutical composition comprising a therapeutically effective amount of a compound or combination of compounds of the present invention, and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier, adjuvant or carrier.

It has been discovered that ritonavir is effective in inhibiting the metabolic enzyme, cytochrome P450 monooxygenase. Hence, the present invention also relates to a method for increasing blood level and improving pharmacokinetics of a drug that is metabolized by cytochrome P450 monooxygenase comprising administering to a human in need of such treatment a therapeutically effective amount of a combination of said drug or a pharmaceutically acceptable salt thereof and a prodrug of ritonavir.

The present invention still further provides a method of inhibiting the replication of HIV comprising contacting said virus with any one of the pharmaceutical compositions of the present invention.

The present invention also provides a method of treating or preventing an HIV infection comprising administering to a patient in need of such treatment any one of the pharmaceutical compositions of the present invention.

A further embodiment of the present invention provides the processes of making a compound of the present invention and intermediates employed in the processes.

DETAILED DESCRIPTION OF THE INVENTION

In the case of inconsistencies between the present disclosure and the references incorporated herein, the present disclosure, including definitions, will prevail.

As used in the present specification the following terms have the meanings indicated:

As used herein, the singular forms "a", "an", and "the" may include plural reference unless the context clearly dictates otherwise.

The term "alkyl," as used herein, refers to a group derived from a straight or branched chain saturated hydrocarbon containing 1, 2, 3, 4, 5, 6, 7, 8, 9, 10, 11 or 12 carbon atoms. Representative examples of alkyl groups include, but not limited to, propyl, butyl, methyl, ethyl, 1-methylpropyl, 2-methylbutyl, tert-butyl and 1-methylethyl (isopropyl).

The term "aryl" as used herein, refers to a phenyl group, or a bicyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Representative examples of aryl groups include, but not limited to, indanyl, indenyl, naphthyl, phenyl and tetrahydronaphthyl. The aryl groups of the present invention can be substituted with 0, 1, 2, 3 or 4 substituents selected from the group consisting of alkyl, halo, haloalkyl and hydroxyalkyl, and are connected to the parent molecular moiety through any substitutable carbon atom of the phenyl group.

The term "arylalkyl", as used herein, refers to an aryl group, as defined herein, attached to the parent molecular moiety through an alkyl group.

The term "cycloalkenyl," as used herein, refers to a non-aromatic, partially unsaturated, monocyclic hydrocarbon ring system, having five to six carbon atoms and zero heteroatom. The five- and six-membered rings have one or two double bonds. Representative examples of cycloalkenyl groups include, but not limited to, cyclopentenyl, cyclopenta-1,3-dienyl and cyclohexenyl.

The term "cycloalkyl," as used herein, refers to a saturated monocyclic hydrocarbon ring system having five or six carbon atoms, zero double bond and zero heteroatom. Representative examples of cycloalkyl groups include, but not limited to, cyclopentyl and cyclohexyl.

The terms "halo" and "halogen" as used herein, refer to F, Cl, Br, and I.

The term "haloalkyl" as used herein, refers to an alkyl group substituted by one, two, three, or four halogen atoms.

The term "hydroxy" or "hydroxyl" as used herein refers to —OH.

The term "hydroxyalkyl" as used herein, refers to an alkyl group substituted by 1, 2, 3, 4 or 5 hydroxy groups.

The term "ritonavir" refers to a pharmaceutically active agent represented by the chemical name $N^1$-((1S,3S,4S)-1-benzyl-3-hydroxy-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide (named by ACD/ChemSketch version 5.06 (developed by Advanced Chemistry Development, Inc., Toronto, ON, Canada)), which is shown structurally below

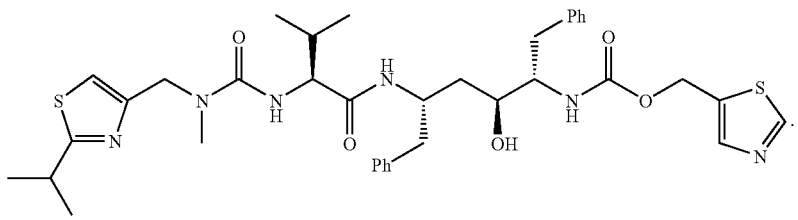

The term "lopinavir" refers to a pharmaceutically active agent represented by the chemical name (2S)—N-((1S,3S,4S)-1-benzyl-4-{[(2,6-dimethylphenoxy)acetyl]amino}-3-hydroxy-5-phenylpentyl)-3-methyl-2-(2-oxotetrahydropyrimidin-1(2H)-yl)butanamide (named by ACD/ChemSketch version 5.06 (developed by Advanced Chemistry Development, Inc., Toronto, ON, Canada)), which is show structurally below:

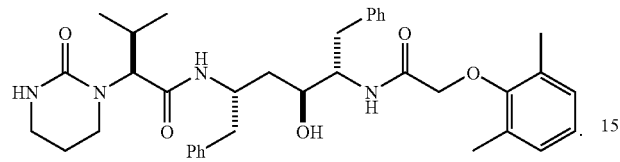

In a first embodiment, the present invention provides a compound having formula (I), (II) or (III)

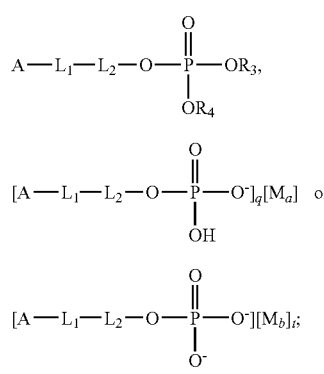

wherein $L_1$ is a bond, —C(O)—, or —C(O)O—; wherein the carbonyl of the —C(O)O— moiety is attached to A of formula (I), (II) or (III);

$L_2$ is —$CR_1R_2)_m$—, m is 1, 2, 3, 4 or 5;

$R_1$ at each occurrence is independently selected from the group consisting of hydrogen and $C_1$-$C_{12}$ alkyl;

$R_2$ at each occurrence is independently selected from the group consisting of hydrogen and $C_1$-$C_{12}$ alkyl;

$R_3$ is hydrogen, $C_1$-$C_{12}$ alkyl or arylalkyl;

$R_4$ is hydrogen, $C_1$-$C_{12}$ alkyl or arylalkyl;

q is 1 or 2;

t is 1 or 2;

$M_a$ is $M_1$ or $M_2$;

$M_b$ is $M_1$ or $M_2$;

$M_1$ is $Na^+$, $K^+$ or $^+N(R_5)(R_6)(R_7)(R_8)$;

$M_2$ is $Ca^{2+}$, $Ba^{2+}$, $Mg^{2+}$, $Zn^{2+}$ or $^+N(R_9)(R_{10})(R_{11})(R_{12})$, $R_5$ is hydrogen, alkyl, hydroxyalkyl, arylalkyl or —C(=NH)NH$_2$;

$R_6$ is hydrogen, alkyl, hydroxyalkyl or arylalkyl;

$R_7$ is hydrogen or alkyl;

$R_8$ is hydrogen or alkyl;

alternatively, $R_5$ and $R_6$, together with the nitrogen atom to which they are attached, form a piperidine ring;

$R_9$ is -alkyl-$N^+(Z_1)(Z_2)(Z_3)$;

$R_{10}$ is hydrogen, alkyl or arylalkyl;

$R_{11}$ is hydrogen or alkyl;

$R_{12}$ is hydrogen or alkyl;

alternatively, $R_9$ and $R_{11}$, together with the nitrogen atom to which they are attached, form a piperazine ring;

$Z_1$ is hydrogen or alkyl;

$Z_2$ is hydrogen or alkyl;

$Z_3$ is hydrogen, alkyl or arylalkyl; and

A is

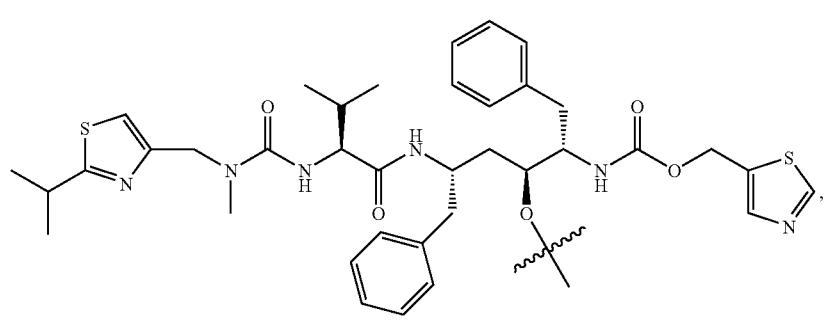

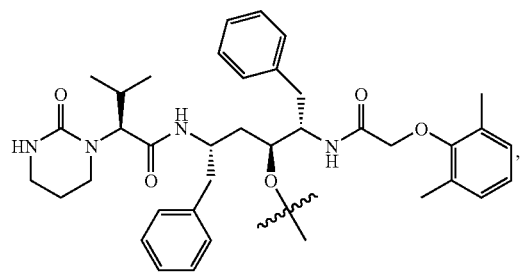

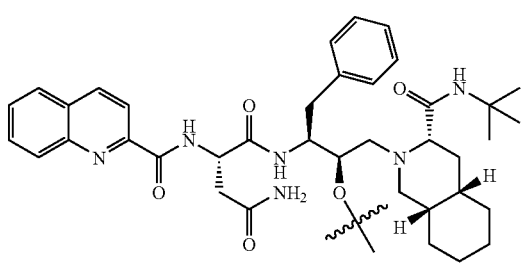

-continued
(iv)
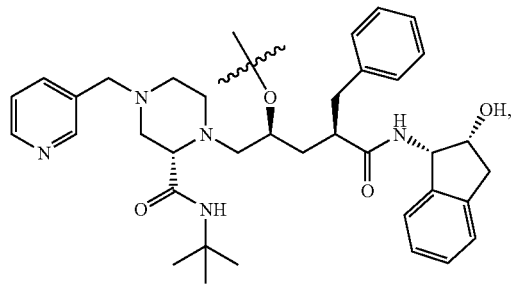
(v)
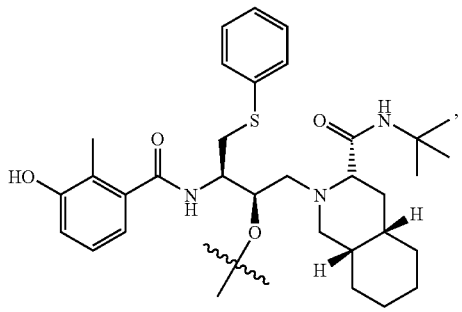
(vi)
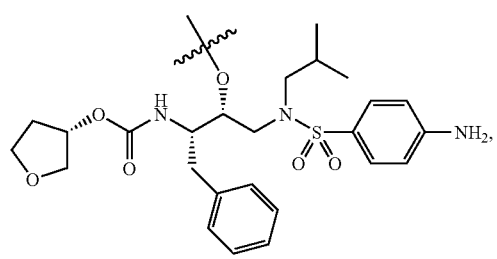
(vii)
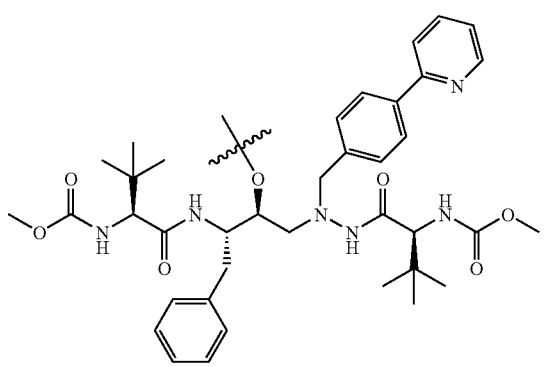
(viii)
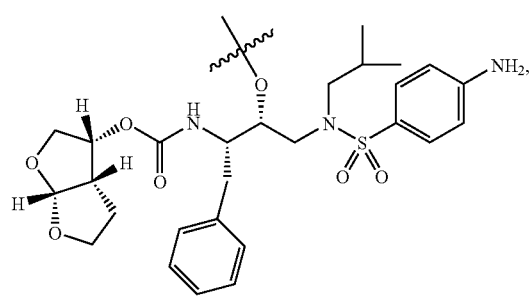
(ix)
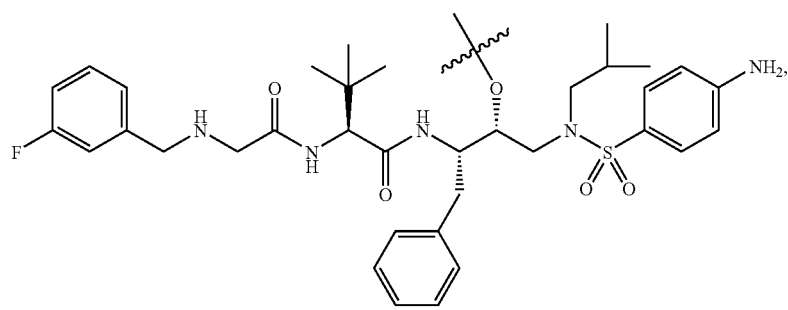
(x)
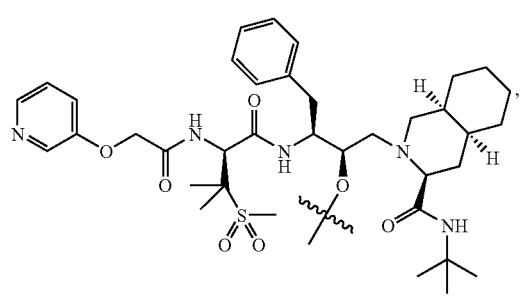
(xi)
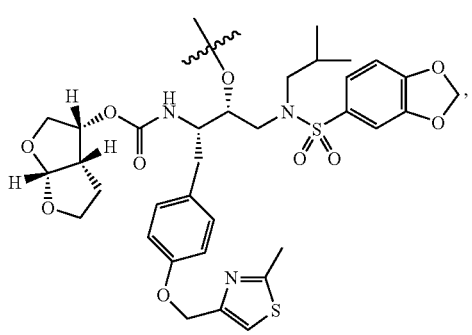

-continued
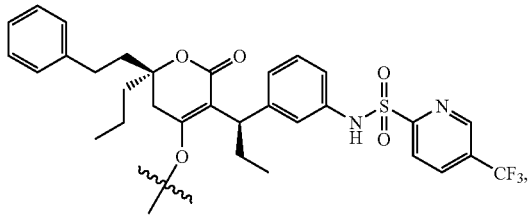
(xii)
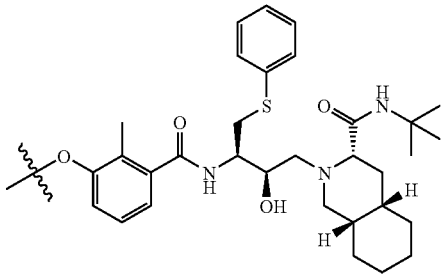
(xiii)
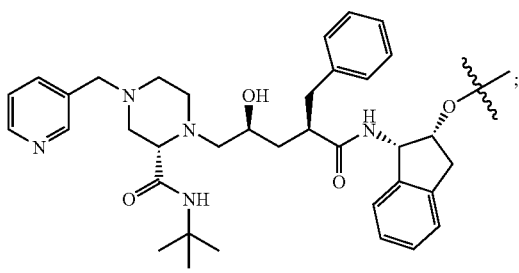
(xiv)
provided that
when q is 1, $M_a$ is $M_1$;
when q is 2, $M_a$ is $M_2$;
when t is 1, $M_b$ is $M_2$;
when t is 2, $M_b$ is $M_1$; and provided that
when A is
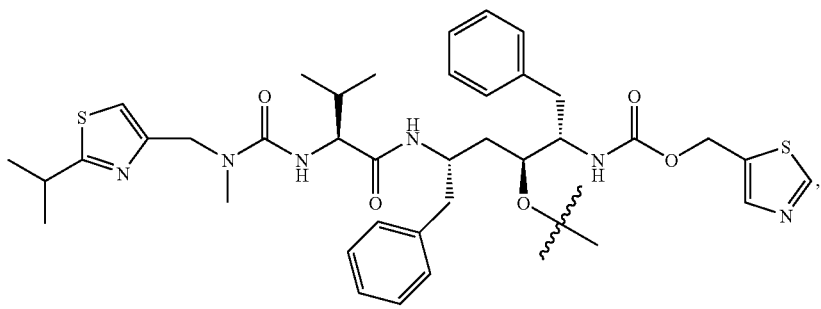
(i)
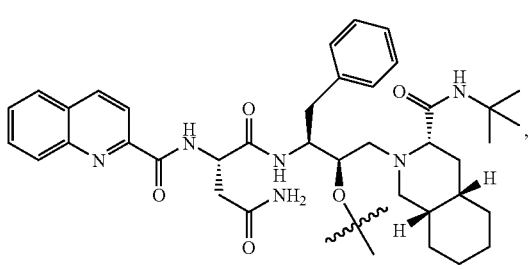
(iii)
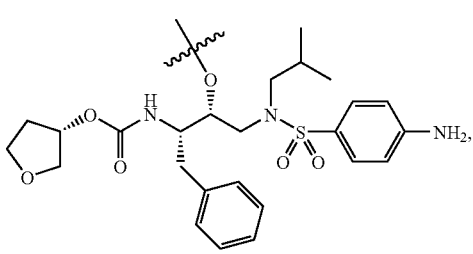
(vi)

-continued
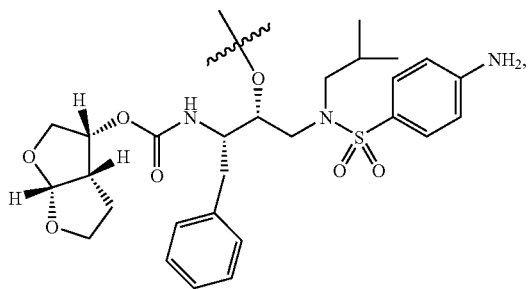
(viii)
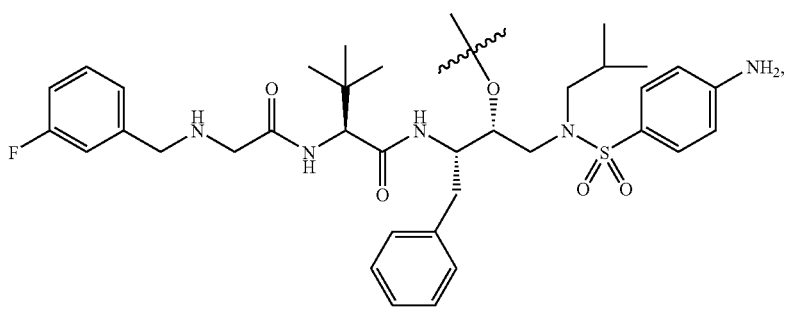
(ix)
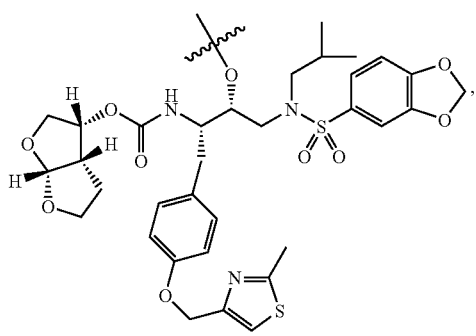
(xi)
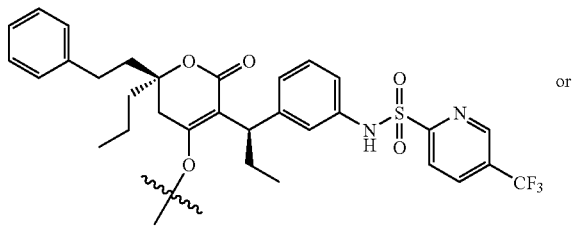
(xii)
or
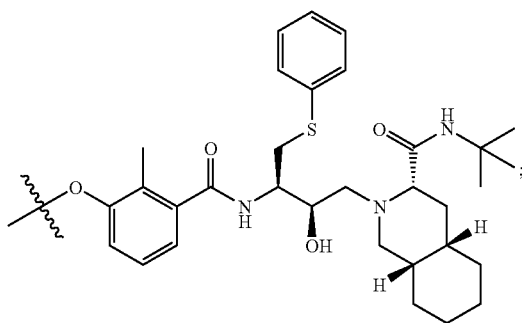
(xiii)
and $L_1$ is a bond, then $L_2$ is not —$CH_2$—.
For example, the first embodiment of the present invention provides a compound having formula (I), (II) or (III) wherein A is

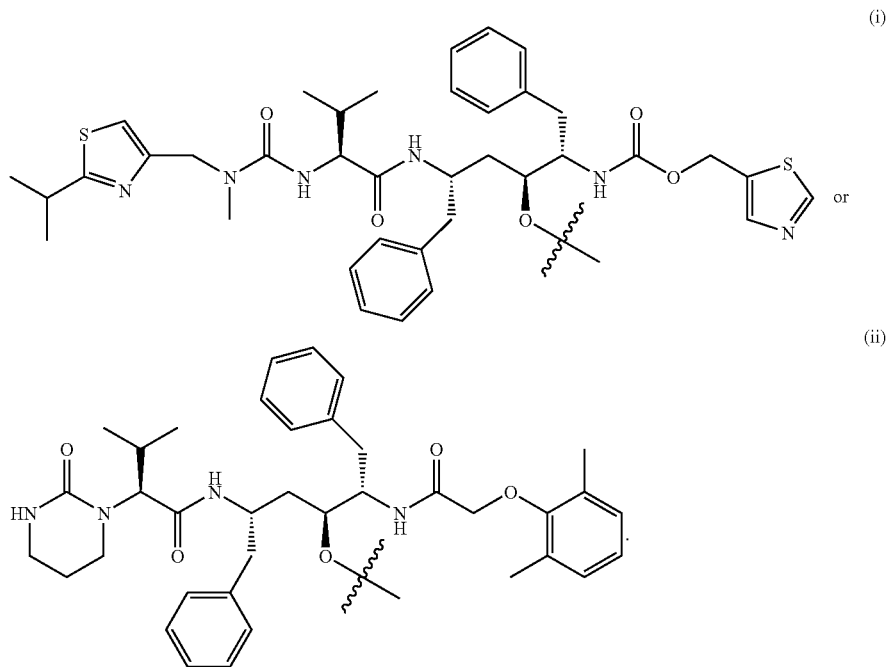

For example, the first embodiment of the present invention provides a compound having formula (I), (II) or (III) wherein q is 1, $M_a$ is $Na^+$, $K^+$ or $NH_4^+$, t is 2 and $M_b$ is $Na^+$, $K^+$ or $NH_4^+$.

For example, the first embodiment of the present invention provides a compound having formula (I), (II) or (III) wherein q is 2, $M_a$ is $Ca^{2+}$, $Ba^{2+}$, $Zn^{2+}$ or $Mg^{2+}$, t is 1 and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is a bond.

For example, the first embodiment of the present invention provides a compound having formula (I), (II) or (III) wherein $L_1$ is a bond and m is 1.

For example, the first embodiment of the present invention provides a compound having formula (I), (II) or (III) wherein $L_1$ is a bond, m is 1, $R_1$ is hydrogen and $R_2$ is hydrogen.

For example, the first embodiment of the present invention provides a compound having formula (I), (II) or (III) wherein $L_1$ is a bond, m is 1, $R_1$ is $C_1$-$C_{12}$ alkyl and $R_2$ is $C_1$-$C_{12}$ alkyl.

For example, the first embodiment of the present invention provides a compound having formula (I), (II) or (III) wherein $L_1$ is a bond, m is 1, $R_1$ is hydrogen and $R_2$ is $C_1$-$C_{12}$ alkyl.

For example, the first embodiment of the present invention provides a compound having formula (I), (II) or (III) wherein $L_1$ is a bond, m is 1, $R_1$ is hydrogen and $R_2$ is $C_1$-alkyl, $C_2$-alkyl or $C_3$-alkyl.

For example, the first embodiment of the present invention provides a compound having formula (I), (II) or (III) wherein $L_1$ is a bond, m is 1, $R_1$ is hydrogen and $R_2$ is methyl, n-propyl or 1-methylethyl.

For example, the first embodiment of the present invention provides a compound having formula (I), (II) or (III) wherein $L_1$ is a bond, m is 1, $R_1$ is hydrogen, $R_2$ is hydrogen, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is a bond, m is 1, $R_1$ is $C_1$-$C_{12}$ alkyl, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is a bond, m is 1, $R_1$ is hydrogen, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is a bond, m is 1, $R_1$ is hydrogen, $R_2$ is $C_1$-alkyl, $C_2$-alkyl or $C_3$-alkyl, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is a bond, m is 1, $R_1$ is hydrogen, $R_2$ is methyl, n-propyl or 1-methylethyl, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is a bond, m is 1, $R_1$ is hydrogen, $R_2$ is hydrogen, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is a bond, m is 1, $R_1$ is $C_1$-$C_{12}$ alkyl, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is a bond, m is 1, $R_1$ is hydrogen, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is a bond, m is 1, $R_1$ is hydrogen, $R_2$ is $C_1$-alkyl, $C_2$-alkyl or $C_3$-alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is a bond, m is 1, $R_1$ is hydrogen, $R_2$ is methyl, n-propyl or 1-methylethyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is —C(O)—.

For example, the first embodiment of the present invention provides a compound having formula (I), (II) or (III) wherein $L_1$ is —C(O)—, $L_2$ is —$(CR_1R_2)_m$— and m is 3.

For example, the first embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—.

For example, the first embodiment of the present invention provides a compound having formula (I), (II) or (III) wherein $L_1$ is —C(O)—, $L_2$ is —$(CR_1R_2)_m$—, m is 3, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—, q is 1, $M_a$ is $Na^+$, $K^+$, or $NH_4^+$, t is 2, and $M_b$ is $Na^+$, $K^+$, or $NH_4^+$.

For example, the first embodiment of the present invention provides a compound having formula (I), (II) or (III) wherein $L_1$ is —C(O)—, $L_2$ is —$(CR_1R_2)_m$—, m is 3, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the first embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

In a second embodiment, the present invention provides a compound having formula (I), (II) or (III)

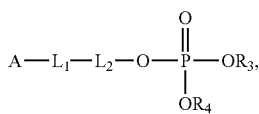

(I)

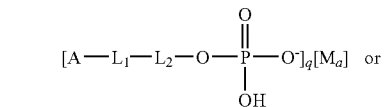

(II)

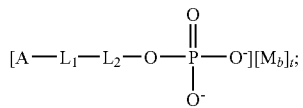

(III)

wherein
$L_1$ is a bond, —C(O)—, or —C(O)O—; wherein the carbonyl of the —C(O)O— moiety is attached to A of formula (I), (II) or (III);
$L_2$ is —$(CR_1R_2)_m$—,
m is 1, 2, 3, 4 or 5;
$R_1$ at each occurrence is independently selected from the group consisting of hydrogen and $C_1$-$C_{12}$ alkyl;
$R_2$ at each occurrence is independently selected from the group consisting of hydrogen and $C_1$-$C_{12}$ alkyl;
$R_3$ is hydrogen, $C_1$-$C_{12}$ alkyl or arylalkyl;
$R_4$ is hydrogen, $C_1$-$C_{12}$ alkyl or arylalkyl;
q is 1 or 2;
t is 1 or 2;
$M_a$ is $M_1$ or $M_2$;
$M_b$ is $M_1$ or $M_2$;
$M_1$ is $Na^+$, $K^+$ or $^+N(R_5)(R_6)(R_7)(R_8)$;
$M_2$ is $Ca^{2+}$, $Ba^{2+}$, $Mg^{2+}$, $Zn^{2+}$ or $^+N(R_9)(R_{10})(R_{11})(R_{12})$;
$R_5$ is hydrogen, alkyl, hydroxyalkyl, arylalkyl or —C(=NH)$NH_2$;
$R_6$ is hydrogen, alkyl, hydroxyalkyl or arylalkyl;
$R_7$ is hydrogen or alkyl;
$R_8$ is hydrogen or alkyl;
alternatively, $R_5$ and $R_6$, together with the nitrogen atom to which they are attached, form a piperidine ring;
$R_9$ is -alkyl-$N^+(Z_1)(Z_2)(Z_3)$;
$R_{10}$ is hydrogen, alkyl or arylalkyl;
$R_{11}$ is hydrogen or alkyl;
$R_{12}$ is hydrogen or alkyl;
alternatively, $R_9$ and $R_{11}$, together with the nitrogen atom to which they are attached, form a piperazine ring;
$Z_1$ is hydrogen or alkyl;
$Z_2$ is hydrogen or alkyl;
$Z_3$ is hydrogen, alkyl or arylalkyl; and
A is

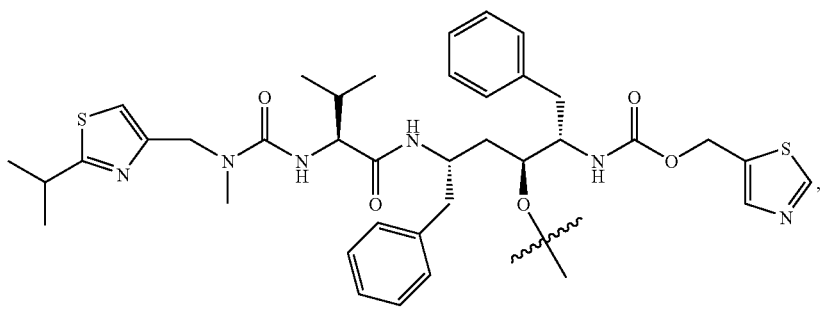

(i)

-continued
(ii)
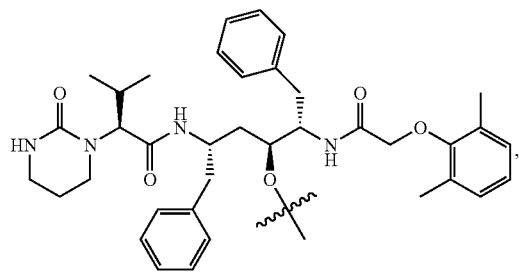
(iii)
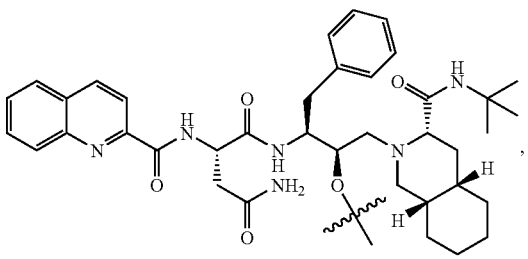
(iv)
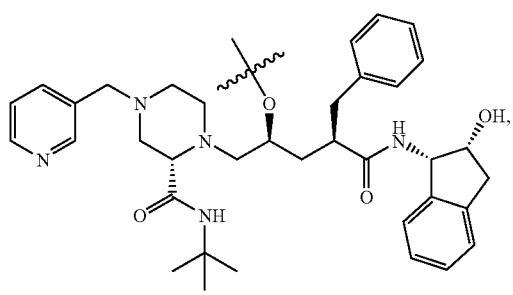
(v)
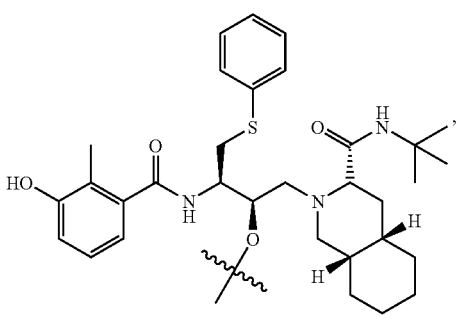
(vi)
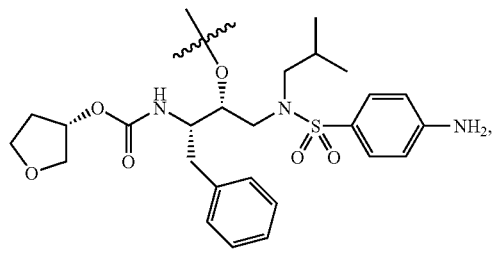
(viii)
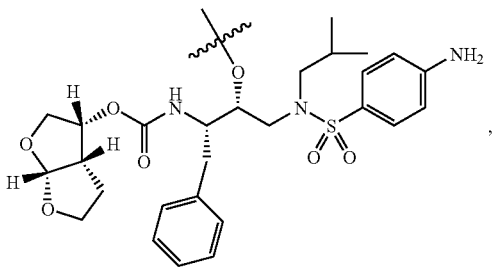
(ix)
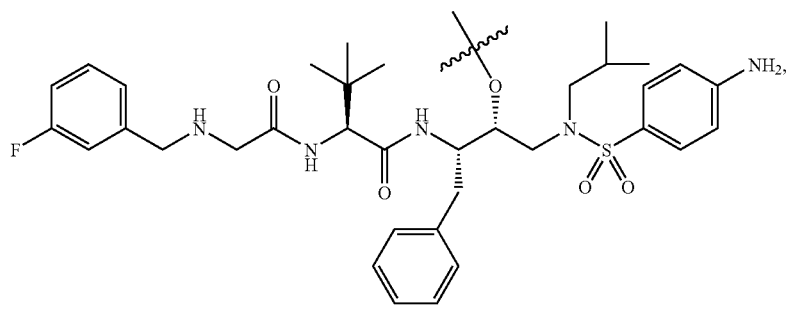
(x)
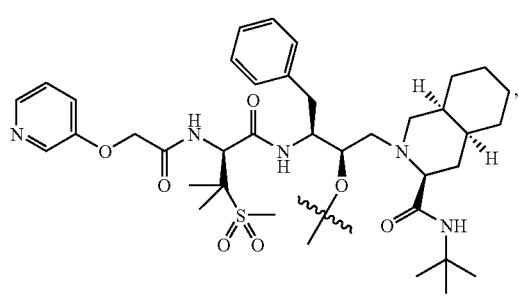
(xi)
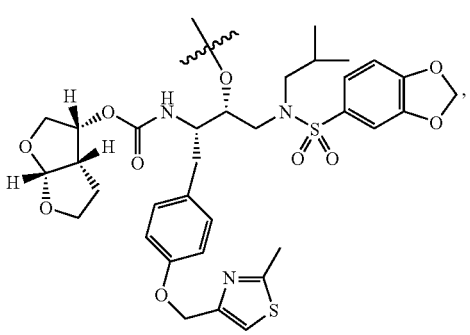

-continued
(xii)
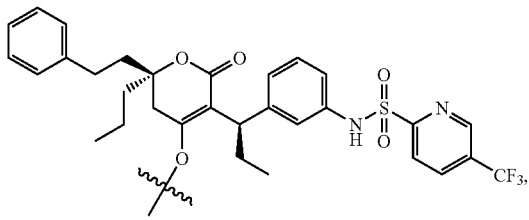
(xiii)
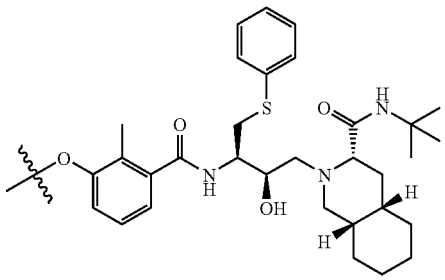
or
(xiv)
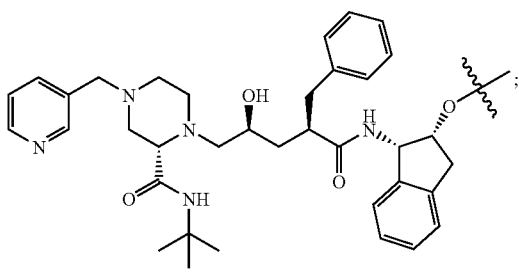
provided that
when q is 1, $M_a$ is $M_1$;
when q is 2, $M_a$ is $M_2$;
when t is 1, $M_b$ is $M_2$;
when t is 2, $M_b$ is $M_1$; and provided that
when A is
(i)
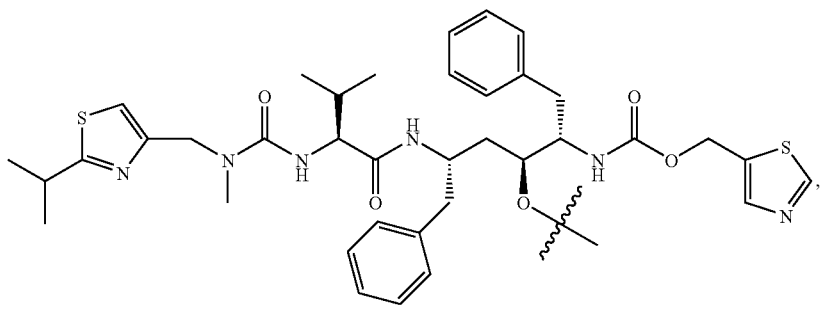
(iii)
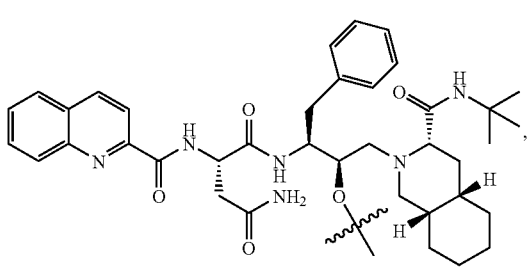
(vi)
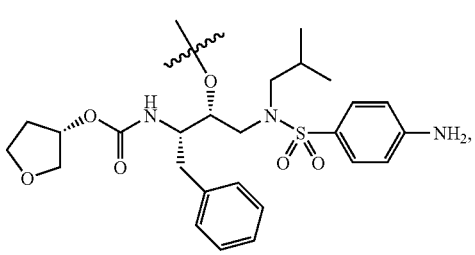

-continued
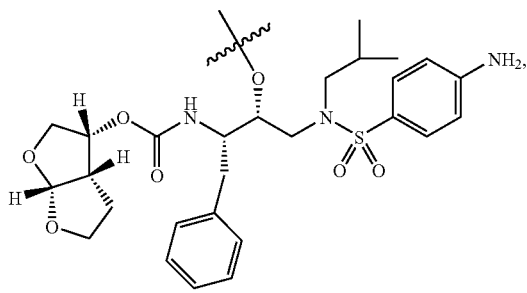
(viii)
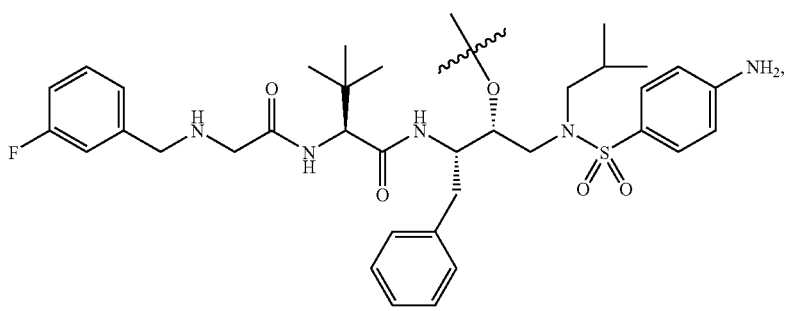
(ix)
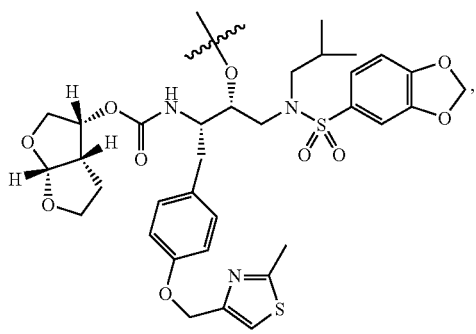
(xi)
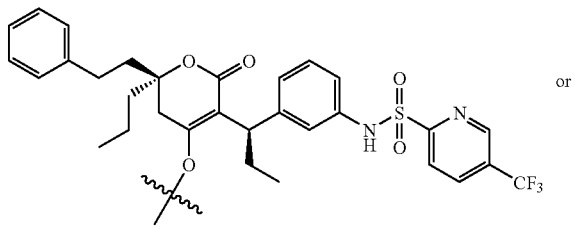
(xii)
or
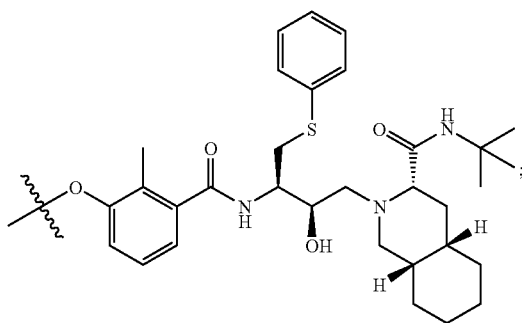
(xiii)
and $L_1$ is a bond, then $L_2$ is not —$CH_2$—.
For example, the second embodiment of the present invention provides a compound having formula (I), (II) or (III) wherein A is

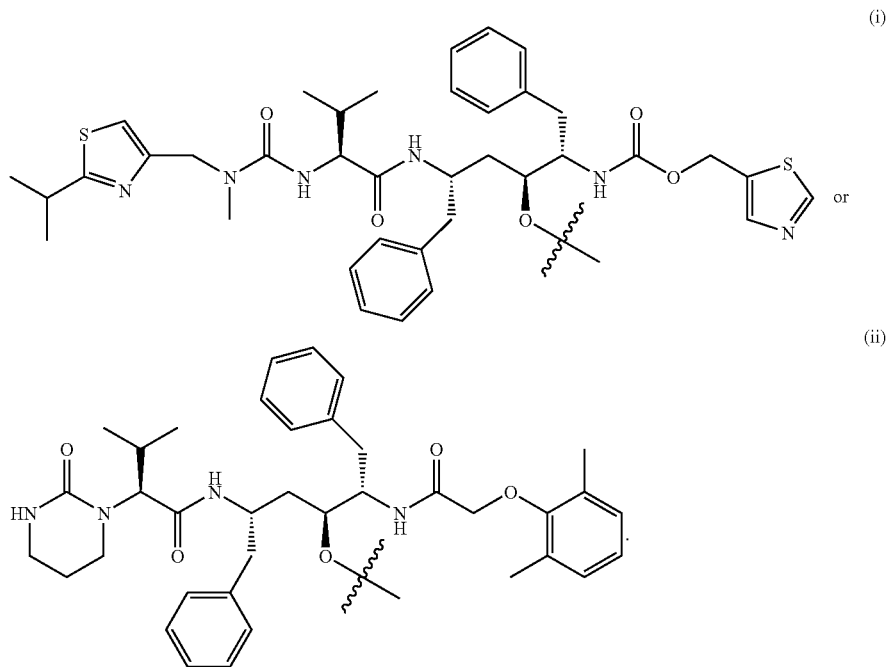

For example, the second embodiment of the present invention provides a compound having formula (I), (II) or (III) wherein q is 1, $M_a$ is $Na^+$, $K^+$ or $NH_4^+$, t is 2 and $M_b$ is $Na^+$, $K^+$ or $NH_4^+$.

For example, the second embodiment of the present invention provides a compound having formula (I), (II) or (III) wherein q is 2, $M_a$ is $Ca^{2+}$, $Ba^{2+}$, $Zn^{2+}$ or $Mg^{2+}$, t is 1 and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is a bond.

For example, the second embodiment of the present invention provides a compound having formula (I), (II) or (III) wherein $L_1$ is a bond and m is 1.

For example, the second embodiment of the present invention provides a compound having formula (I), (II) or (III) wherein $L_1$ is a bond, m is 1, $R_1$ is hydrogen and $R_2$ is hydrogen.

For example, the second embodiment of the present invention provides a compound having formula (I), (II) or (III) wherein $L_1$ is a bond, m is 1, $R_1$ is $C_1$-$C_{12}$ alkyl and $R_2$ is $C_1$-$C_{12}$ alkyl.

For example, the second embodiment of the present invention provides a compound having formula (I), (II) or (III) wherein $L_1$ is a bond, m is 1, $R_1$ is hydrogen and $R_2$ is $C_1$-$C_{12}$ alkyl.

For example, the second embodiment of the present invention provides a compound having formula (I), (II) or (III) wherein $L_1$ is a bond, m is 1, $R_1$ is hydrogen and $R_2$ is $C_1$-alkyl, $C_2$-alkyl or $C_3$-alkyl.

For example, the second embodiment of the present invention provides a compound having formula (I), (II) or (III) wherein $L_1$ is a bond, m is 1, $R_1$ is hydrogen and $R_2$ is methyl, n-propyl or 1-methylethyl.

For example, the second embodiment of the present invention provides a compound having formula (I), (II) or (III) wherein $L_1$ is a bond, m is 1, $R_1$ is hydrogen, $R_2$ is hydrogen, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is a bond, m is 1, $R_1$ is $C_1$-$C_{12}$ alkyl, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is a bond, m is 1, $R_1$ is hydrogen, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is a bond, m is 1, $R_1$ is hydrogen, $R_2$ is $C_1$-alkyl, $C_2$-alkyl or $C_3$-alkyl, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is a bond, m is 1, $R_1$ is hydrogen, $R_2$ is methyl, n-propyl or 1-methylethyl, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is a bond, m is 1, $R_1$ is hydrogen, $R_2$ is hydrogen, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is a bond, m is 1, $R_1$ is $C_1$-$C_{12}$ alkyl, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III)

wherein $L_1$ is a bond, m is 1, $R_1$ is hydrogen, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is a bond, m is 1, $R_1$ is hydrogen, $R_2$ is $C_1$-alkyl, $C_2$-alkyl or $C_3$-alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is a bond, m is 1, $R_1$ is hydrogen, $R_2$ is methyl, n-propyl or 1-methylethyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is —C(O)—.

For example, the second embodiment of the present invention provides a compound having formula (I), (II) or (III) wherein $L_1$ is —C(O)—, $L_2$ is —$(CR_1R_2)_m$— and m is 3.

For example, the second embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—.

For example, the second embodiment of the present invention provides a compound having formula (I), (II) or (III) wherein $L_1$ is —C(O)—, $L_2$ is —$(CR_1R_2)_m$—, m is 3, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—, q is 1, $M_a$ is $Na^+$, $K^+$, or $NH_4^+$, t is 2, and $M_b$ is $Na^+$, $K^+$, or $NH_4^+$.

For example, the second embodiment of the present invention provides a compound having formula (I), (II) or (III) wherein $L_1$ is —C(O)—, $L_2$ is —$(CR_1R_2)_m$—, m is 3, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the second embodiment of the present invention provides a compound having formula (I), (II) or (III) wherein $L_1$ is —C(O)—, $L_2$ is —$CH_2$—$C(CH_3)_2$—$CH_2$—, —$C(CH_3)_2$—$CH_2$—$CH_2$— or —$CH_2$—$CH_2$—$C(CH_3)_2$—, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

In a third embodiment, the present invention provides a compound having formula (I), (II) or (III),

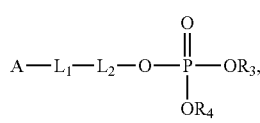
(I)

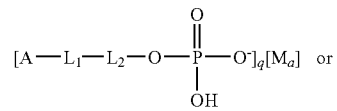
(II)

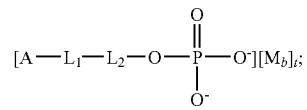
(III)

wherein $L_1$ is a bond, —C(O)—, or —C(O)O—; wherein the carbonyl of the —C(O)O— moiety is attached to A of formula (I), (II) or (III);

$L_2$ is —$(CR_1R_2)_m$—, m is 1, 2, 3, 4 or 5;

$R_1$ at each occurrence is independently selected from the group consisting of hydrogen and $C_1$-$C_{12}$ alkyl;

$R_2$ at each occurrence is independently selected from the group consisting of hydrogen and $C_1$-$C_{12}$ alkyl;

$R_3$ is hydrogen, $C_1$-$C_{12}$ alkyl or arylalkyl;

$R_4$ is hydrogen, $C_1$-$C_{12}$ alkyl or arylalkyl;

q is 1 or 2;

t is 1 or 2;

$M_a$ is $M_1$ or $M_2$;

$M_b$ is $M_1$ or $M_2$;

$M_1$ is $Na^+$, $K^+$ or $^+N(R_5)(R_6)(R_7)(R_8)$;

$M_2$ is $Ca^{2+}$, $Ba^{2+}$, $Mg^{2+}$, $Zn^{2+}$ or $^+N(R_9)(R_{10})(R_{11})(R_{12})$, $R_5$ is hydrogen, alkyl, hydroxyalkyl, arylalkyl or —C(=NH)$NH_2$;

$R_6$ is hydrogen, alkyl, hydroxyalkyl or arylalkyl;

$R_7$ is hydrogen or alkyl;

$R_8$ is hydrogen or alkyl;

alternatively, $R_5$ and $R_6$, together with the nitrogen atom to which they are attached, form a piperidine ring;

$R_9$ is -alkyl-$N^+(Z_1)(Z_2)(Z_3)$;

$R_{10}$ is hydrogen, alkyl or arylalkyl;

$R_{11}$ is hydrogen or alkyl;

$R_{12}$ is hydrogen or alkyl;

alternatively, $R_9$ and $R_{11}$, together with the nitrogen atom to which they are attached, form a piperazine ring;

$Z_1$ is hydrogen or alkyl;

$Z_2$ is hydrogen or alkyl;

$Z_3$ is hydrogen, alkyl or arylalkyl; and

A is

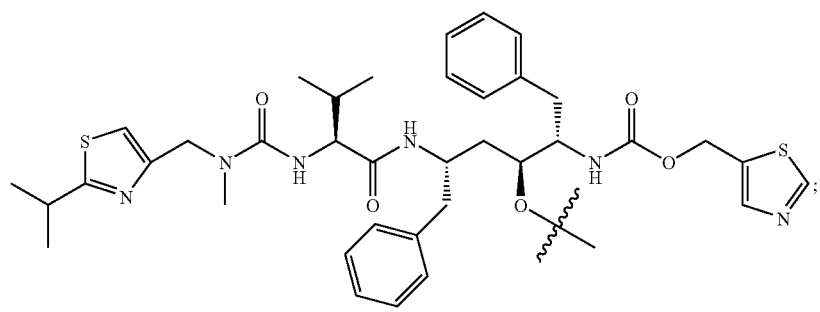
(i)

provided that
when q is 1, $M_a$ is $M_1$;
when q is 2, $M_a$ is $M_2$;
when t is 1, $M_b$ is $M_2$;
when t is 2, $M_b$ is $M_1$; and
when $L_1$ is a bond, $L_2$ is not —$(CH_2)$—.

For example, the third embodiment of the present invention provides a compound having formula (I), (II) or (III) wherein $L_1$ is a bond.

For example, the third embodiment of the present invention provides a compound having formula (I), (II) or (III) wherein q is 1, $M_a$ is $Na^+$, $K^+$ or $NH_4^+$, t is 2 and $M_b$ is $Na^+$, $K^+$ or $NH_4^+$.

For example, the third embodiment of the present invention provides a compound having formula (I), (II) or (III) wherein $L_1$ is a bond, $L_2$ is —$(CR_1R_2)_m$—, m is 1, $R_1$ is hydrogen and $R_2$ is $C_1$-$C_{12}$ alkyl.

For example, the third embodiment of the present invention provides a compound having formula (I), (II) or (III) wherein $L_1$ is a bond, $L_2$ is —$(CR_1R_2)_m$—, m is 1, $R_1$ is $C_1$-$C_{12}$ alkyl and $R_2$ is $C_1$-$C_{12}$ alkyl.

For example, the third embodiment of the present invention provides a compound having formula (I), (II) or (III) wherein $L_1$ is a bond, $L_2$ is —$(CR_1R_2)_m$—, m is 1, $R_1$ is hydrogen and $R_2$ is $C_1$-alkyl, $C_2$-alkyl or $C_3$-alkyl.

For example, the third embodiment of the present invention provides a compound having formula (I), (II) or (III) wherein $L_1$ is a bond, $L_2$ is —$(CR_1R_2)_m$—, m is 1, $R_1$ is hydrogen and $R_2$ is methyl, n-propyl or 1-methylethyl.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the third embodiment of the present invention provides a compound having formula (I), (II) or (III) wherein $L_1$ is a bond, $L_2$ is —$(CR_1R_2)_m$—, m is 1, $R_1$ is $C_1$-$C_{12}$ alkyl, $R_2$ is $C_1$-$C_{12}$ alkyl, q is 1, $M_a$ is $Na^+$, $K^+$, or $NH_4^+$, t is 2, and $M_b$ is $Na^+$, $K^+$, or $NH_4^+$.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is $C_1$-alkyl, $C_2$-alkyl or $C_3$-alkyl, q is 1, $M_a$ is $Na^+$, $K^+$, or $NH_4^+$, t is 2, and $M_b$ is $Na^+$, $K^+$, or $NH_4^+$.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is methyl, n-propyl or 1-methylethyl, q is 1, $M_a$ is $Na^+$, $K^+$, or $NH_4^+$, t is 2, and $M_b$ is $Na^+$, $K^+$, or $NH_4^+$.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the third embodiment of the present invention provides a compound having formula (I), (II) or (III) wherein $L_1$ is a bond, $L_2$ is —$(CR_1R_2)_m$—, m is 1, $R_1$ is $C_1$-$C_{12}$ alkyl, $R_2$ is $C_1$-$C_{12}$ alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is $C_1$-alkyl, $C_2$-alkyl or $C_3$-alkyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the third embodiment of the present invention provides a compound having formula (I), (II) or (III) wherein $L_1$ is a bond, $L_2$ is —$(CR_1R_2)_m$—, m is 1, $R_1$ is hydrogen, $R_2$ is methyl, n-propyl or 1-methylethyl, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

For example, the third embodiment of the present invention provides a compound having formula (I), (II) or (III) wherein $L_1$ is —$C(O)$—, $L_2$ is —$(CR_1R_2)_m$—, and m is 3.

For example, the third embodiment of the present invention provides a compound having formula (I), (II) or (III) wherein $L_1$ is —$C(O)$—, $L_2$ is —$(CR_1R_2)_m$—, m is 3, q is 1, $M_a$ is $Na^+$, $K^+$, or $NH_4^+$, t is 2 and $M_b$ is $Na^+$, $K^+$, or $NH_4^+$.

For example, the third embodiment of the present invention provides a compound having formula (I), (II) or (III) wherein $L_1$ is —$C(O)$—, $L_2$ is —$(CR_1R_2)_m$—, m is 3, q is 2, $M_a$ is $Ca^{2+}$, $Ba^{2+}$, $Zn^{2+}$ or $Mg^{2+}$, t is 1, and $M_b$ is $Ca^{2+}$, $Ba^{2+}$, $Zn^{2+}$ or $Mg^{2+}$.

In a fourth embodiment, the present invention provides a compound having formula (I), (II) or (III),

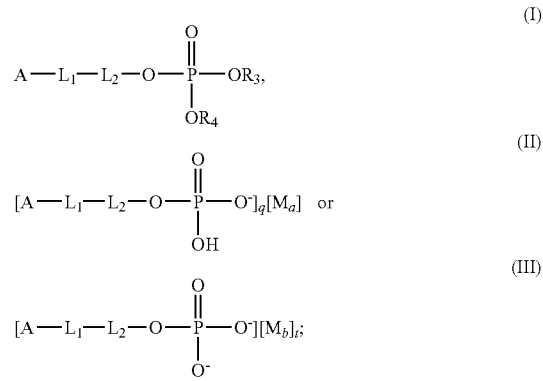

wherein
$L_1$ is a bond, —$C(O)$—, or —$C(O)O$—; wherein the carbonyl of the —$C(O)O$— moiety is attached to A of formula (I), (II) or (III);
$L_2$ is —$CR_1R_2)_m$—,
m is 1, 2, 3, 4 or 5;
$R_1$ at each occurrence is independently selected from the group consisting of hydrogen and $C_1$-$C_{12}$ alkyl;
$R_2$ at each occurrence is independently selected from the group consisting of hydrogen and $C_1$-$C_{12}$ alkyl;
$R_3$ is hydrogen, $C_1$-$C_{12}$ alkyl or arylalkyl;
$R_4$ is hydrogen, $C_1$-$C_{12}$ alkyl or arylalkyl;
q is 1 or 2;
t is 1 or 2;
$M_a$ is $M_1$ or $M_2$;
$M_b$ is $M_1$ or $M_2$;
$M_1$ is $Na^+$, $K^+$ or $^+N(R_5)(R_6)(R_7)(R_8)$;
$M_2$ is $Ca^{2+}$, $Ba^{2+}$, $Mg^{2+}$, $Zn^{2+}$ or $^+N(R_9)(R_{10})(R_{11})(R_{12})$,
$R_5$ is hydrogen, alkyl, hydroxyalkyl, arylalkyl or —$C(=NH)NH_2$;
$R_6$ is hydrogen, alkyl, hydroxyalkyl or arylalkyl;
$R_7$ is hydrogen or alkyl;
$R_8$ is hydrogen or alkyl;
alternatively, $R_5$ and $R_6$, together with the nitrogen atom to which they are attached, form a piperidine ring;
$R_9$ is -alkyl-$N^+(Z_1)(Z_2)(Z_3)$;
$R_{10}$ is hydrogen, alkyl or arylalkyl;
$R_{11}$ is hydrogen or alkyl;
$R_{12}$ is hydrogen or alkyl;
alternatively, $R_9$ and $R_{11}$, together with the nitrogen atom to which they are attached, form a piperazine ring;
$Z_1$ is hydrogen or alkyl;

$Z_2$ is hydrogen or alkyl;
$Z_3$ is hydrogen, alkyl or arylalkyl; and
A is (ii)

provided that
when q is 1, $M_a$ is $M_1$;
when q is 2, $M_a$ is $M_2$;
when t is 1, $M_b$ is $M_2$; and
when t is 2, $M_b$ is $M_1$.

For example, the fourth embodiment of the present invention provides a compound having formula (I), (II) or (III) wherein $L_1$ is a bond.

For example, the fourth embodiment of the present invention provides a compound having formula (I), (II) or (III) wherein q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, and $R_2$ is hydrogen.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, and $R_2$ is $C_1$-$C_{12}$ alkyl.

For example, the fourth embodiment of the present invention provides a compound having formula (I), (II) or (III) wherein $L_1$ is a bond, $L_2$ is $—(CR_1R_2)_m—$, m is 1, $R_1$ is $C_1$-$C_{12}$ alkyl, and $R_2$ is $C_1$-$C_{12}$ alkyl.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, and $R_2$ is $C_1$-alkyl, $C_2$-alkyl or $C_3$-alkyl.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, and $R_2$ is methyl, ethyl, n-propyl or 1-methylethyl.

For example, the fourth embodiment of the present invention provides a compound having formula (I), (II) or (III) wherein $L_1$ is a bond, $L_2$ is $—(CR_1R_2)_m—$, m is 1, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is $C_1$-$C_{12}$ alkyl, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is hydrogen, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, $R_1$ is $C_1$-$C_{12}$ alkyl, $R_2$ is $C_1$-$C_{12}$ alkyl, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is hydrogen, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1, $R_1$ is $C_1$-$C_{12}$ alkyl, $R_2$ is $C_1$-$C_{12}$ alkyl, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is $C_1$-$C_{12}$ alkyl, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is $C_1$-alkyl, $C_2$-alkyl or $C_3$-alkyl, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is $C_1$-alkyl, $C_2$-alkyl or $C_3$-alkyl, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is hydrogen methyl, ethyl, n-propyl or 1-methylethyl, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is a bond, $L_2$ is $—(CR_1R_2)_m—$, m is 1, $R_1$ is hydrogen, $R_2$ is methyl, ethyl, n-propyl or 1-methylethyl, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

For example, the fourth embodiment of the present invention provides a compound having formula (I), (II) or (III) wherein $L_1$ is $—C(O)—$.

For example, the fourth embodiment of the present invention provides a compound having formula (I), (II) or (III) wherein $L_1$ is $—C(O)—$, $L_2$ is $—(CR_1R_2)_m—$, and m is 3.

For example, the fourth embodiment of the present invention provides a compound having formula (I), (II) or (III) wherein $L_1$ is $—C(O)—$, $L_2$ is $—(CR_1R_2)_m—$, m is 3, q is 1, $M_a$ is $Na^+$, $K^+$ or $NH_4^+$, t is 2 and $M_b$ is $Na^+$, $K^+$ or $NH_4^+$.

For example, the fourth embodiment of the present invention provides a compound having formula (I), (II) or (III) wherein $L_1$ is —C(O)—, $L_2$ is —$(CR_1R_2)_m$—, m is 3, q is 2, $M_a$ is $Ca^{2+}$, $Ba^{2+}$, $Mg^{2+}$ or $Zn^{2+}$, t is 1 and $M_b$ is $Ca^{2+}$, $Ba^{2+}$, $Mg^{2+}$ or $Zn^{2+}$.

Exemplary compounds of the present invention include, but are not limited to, disodium
$N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
calcium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
disodium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
calcium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
disodium $N^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
calcium $N^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
disodium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
calcium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
disodium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
calcium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;
disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate;
calcium disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate;
disodium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate;
calcium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate;
disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate;
calcium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate;
disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate; and
calcium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate.

In a fifth embodiment, the present invention provides a process for the preparation of a compound of formula (I)

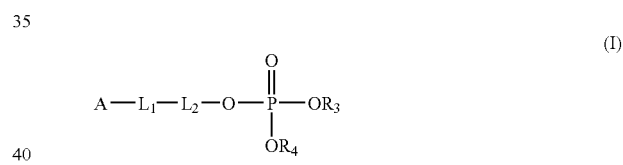

wherein
$L_1$ is a bond,
$L_2$ is —$(CR_1R_2)_m$—,
m is 1;
$R_1$ is selected from the group consisting of hydrogen and $C_1$-$C_{12}$ alkyl;
$R_2$ is selected from the group consisting of hydrogen and $C_1$-$C_{12}$ alkyl;
$R_3$ is hydrogen
$R_4$ is hydrogen and
A is

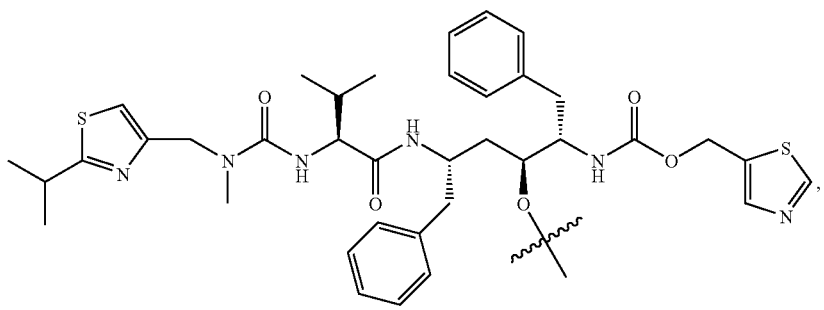

(ii)
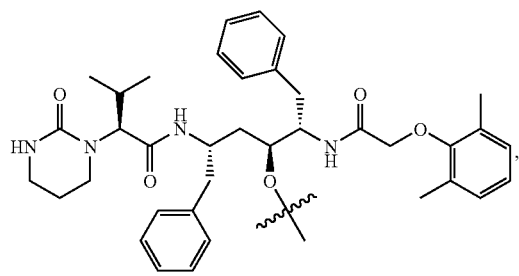
(iii)
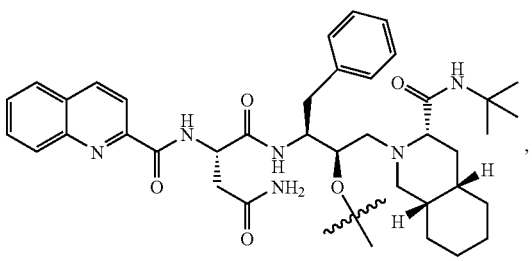
(iv)
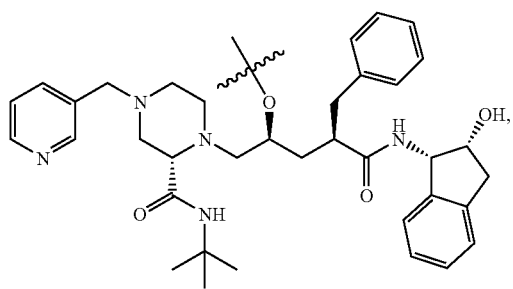
(v)
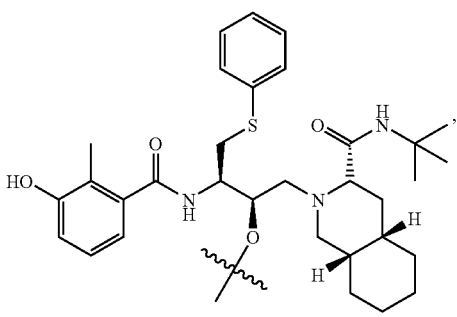
(vi)
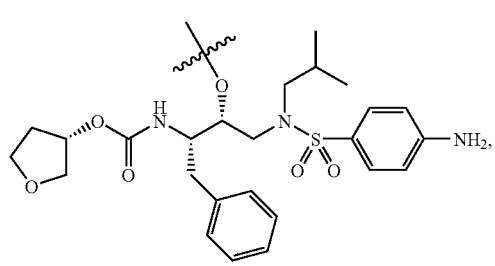
(viii)
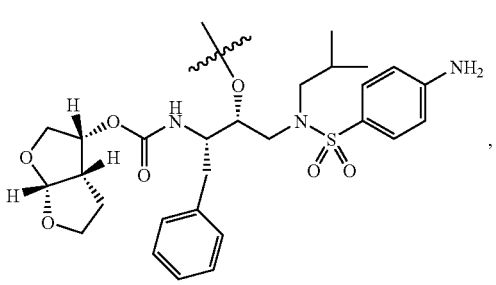
(ix)
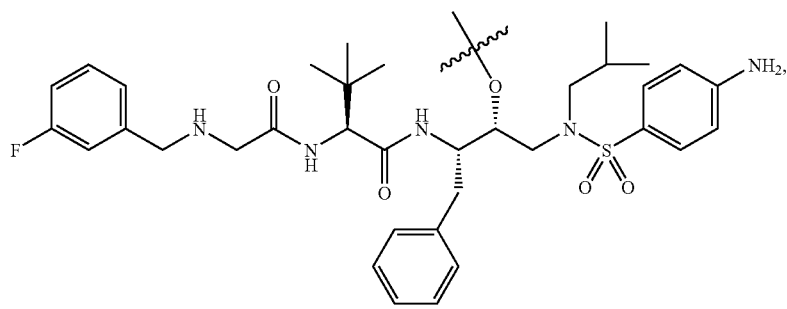
(x)
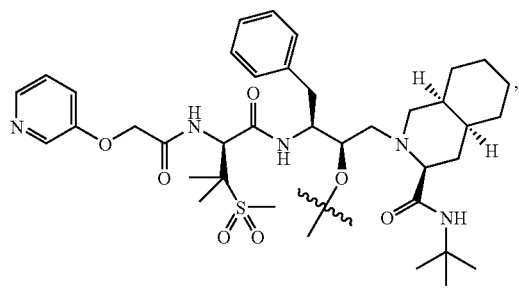
(xi)
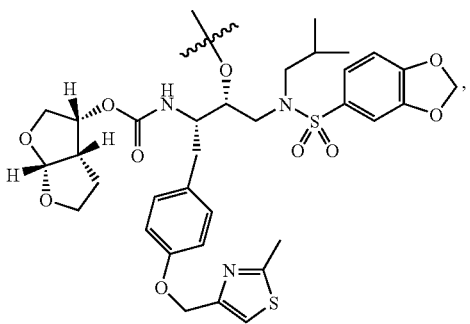

-continued

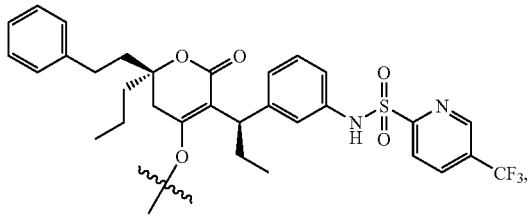
(xii)

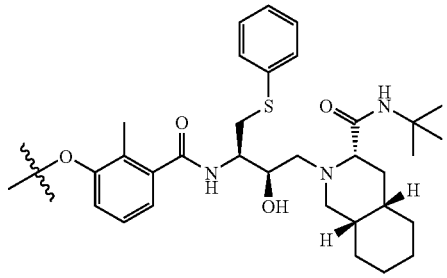
(xiii)

or

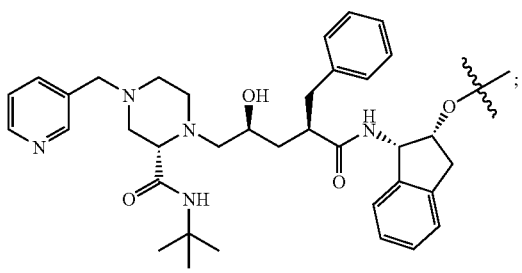
(xiv)

comprising (a) contacting a compound of formula A-H, alkyl sulfide having formula $H-L_2-SR_{90}$ wherein $R_{90}$ is alkyl, an oxidizing agent, and with or without a base, in a solvent, to provide a compound of formula (2)

$$A-L_2-SR_{90} \quad (2)$$

and (b) contacting the compound of formula (2), phosphoric acid, reagent 1, in a solvent, and with or without a dehydrating reagent.

Examples of the alkyl sulfide in step (a) include, but are not limited to, methyl sulfide, ethyl sulfide, butyl sulfide and diisobutyl sulfide.

Examples of the oxidizing agents in step (a) include, but are not limited to, benzoyl peroxide, N-chlorosuccinimide and N-chloro-N-methylacetamide.

Examples of the base in step (a) include, but are not limited to, triethylamine, diisopropylethylamine, tributylamine, morpholine and 1-methylimidazole.

The solvent used in step (a) refers to any organic solvent that will allow the reaction in step (a) to proceed to completion or substantially completion. Examples of the solvents for the reaction in step (a) include, but are not limited to, acetonitrile and tetrahydrofuran.

The reaction of step (a) can be performed at a temperature from about −20° C. to about 50° C., preferably at a temperature from about −10° C. to about 25° C.

Examples of reagents 1 include, in step (b) but are not limited to, N-iodosuccinimide, N-chlorosuccinimide, N-bromosuccinimide, iodonium dicollidine triflate, methyl iodide, $AgNO_3$ and trimethylsilyl chloride. Preferred reagent 1 is N-iodosuccinimide.

Examples of the dehydrating agents in step (b) include, but are not limited to, molecular sieves, magnesium sulfate, $Na_2SO_4$, and $K_2CO_3$.

The solvent used in step (b) refers to any organic solvent that will allow the reaction in step (b) to proceed to completion or substantially completion. Examples of the solvents for the reaction in step (b) include, but are not limited to, tetrahydrofuran, N,N-dimethylformamide, ethyl acetate, acetonitrile, dichloromethane and dichloroethane.

The reaction of step (b) can be performed at a temperature from about −40° C. to about room temperature, preferably at about −20° C. to about room temperature, more preferably at about −10° C. to about 25° C., and most preferably at about −10° C. to about 10° C.

For example, the fifth embodiment of the present invention provides a process for the preparation of a compound of formula (I), comprising (a) contacting a compound of formula A-H, alkyl sulfide having formula $H-L_2-SR_{90}$, wherein $R_{90}$ is methyl, ethyl, and butyl, N-chlorosuccinimide, and a base, in a solvent, to provide a compound of formula $A-L_2-SR_{90}$, and (b) contacting the compound of formula $A-L_2-SR_{90}$, phosphoric acid, N-iodosuccinimide, and with or without a dehydrating agent, in a solvent.

For example, the fifth embodiment of the present invention provides a process for the preparation of a compound of formula (I), comprising (a) contacting a compound of formula A-H, alkyl sulfide having formula $H-L_2-SR_{90}$, wherein $R_{90}$ is methyl, ethyl, and butyl, N-chlorosuccinimide, and a base, in a solvent, at a temperature from about −20° C. to about 10° C., to provide a compound of formula $A-L_2-SR_{90}$, and (b) contacting the compound of formula $A-L_2-SR_{90}$, phosphoric acid, N-iodosuccinimide, and with or without a dehydrating agent, in a solvent, at a temperature from about −20° C. to about 25° C.

For example, the fifth embodiment of the present invention provides a process for the preparation of a compound of formula (I), comprising (a) contacting a compound of formula A-H, alkyl sulfide having formula $H-L_2-SR_{90}$, wherein $R_{90}$ is methyl, ethyl, and butyl, N-chlorosuccinimide, and a base, in a solvent, at a temperature from about −10° C. to about 5° C., to provide a compound of formula $A-L_2-SR_{90}$, and (b) contacting the compound of formula $A-L_2-SR_{90}$, phosphoric acid, N-iodosuccinimide, and with or without a dehydrating agent, in a solvent, at a temperature from about −10° C. to about 10° C.

For example, the fifth embodiment of the present invention provides a process for the preparation of a compound of formula (I), comprising (a) contacting a compound of formula A-H, alkyl sulfide having formula H-L$_2$-SR$_{90}$, wherein R$_{90}$ is methyl, ethyl, and butyl, N-chlorosuccinimide, triethylamine, in a solvent such as acetonitrile or tetrahydrofuran, at a temperature from about −10° C. to about 5° C., to provide a compound of formula A-L$_2$-SR$_{90}$, and (b) contacting the compound of formula A-L$_2$-SR$_{90}$, phosphoric acid, N-iodosuccinimide, and with or without a dehydrating agent, in a solvent such as tetrahydrofuran or N,N-dimethylformamide, at a temperature from about −10° C. to about 10° C.

In a sixth embodiment, the present invention also provides a process for the preparation of a compound of formula (I)

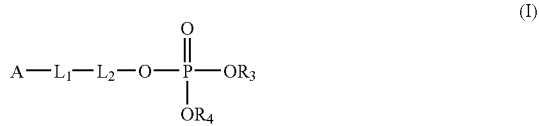
(I)

wherein

L$_1$ is a bond,

L$_2$ is —(CR$_1$R$_2$)$_m$—, m is 1;

R$_1$ is selected from the group consisting of hydrogen and C$_1$-C$_{12}$ alkyl;

R$_2$ is selected from the group consisting of hydrogen and C$_1$-C$_{12}$ alkyl;

R$_3$ is hydrogen

R$_4$ is hydrogen and

A is

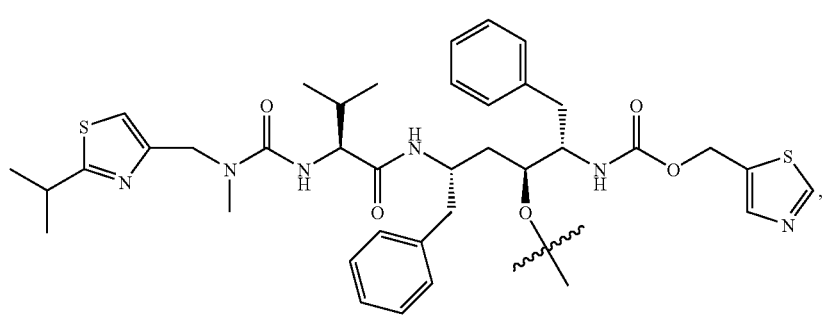
(i)

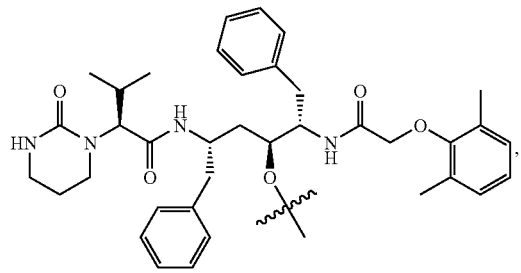
(ii)

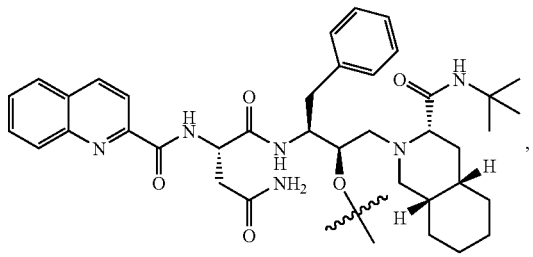
(iii)

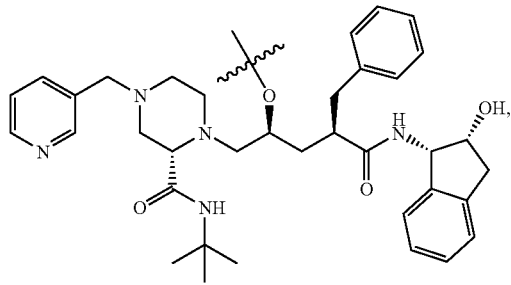
(iv)

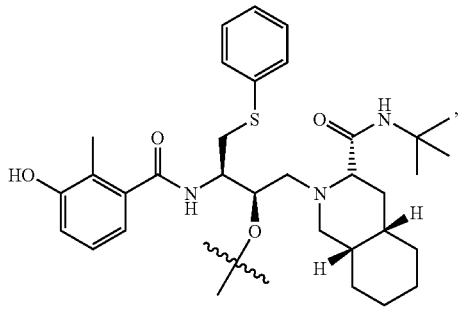
(v)

-continued
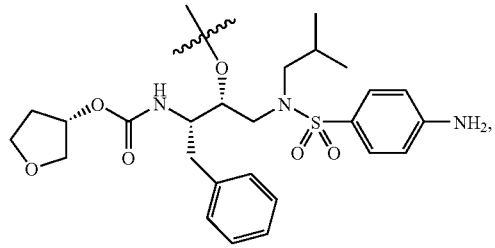
(vi)
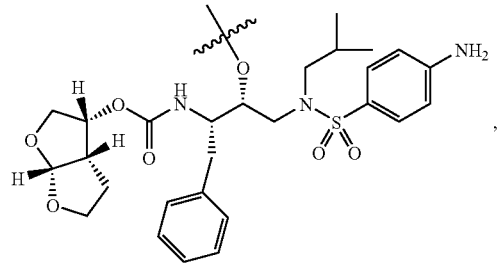
(viii)
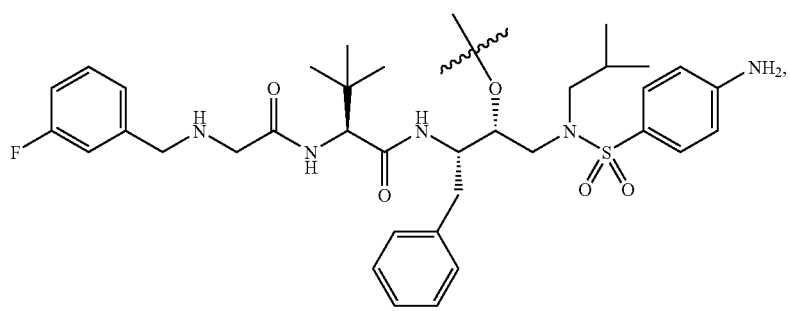
(ix)
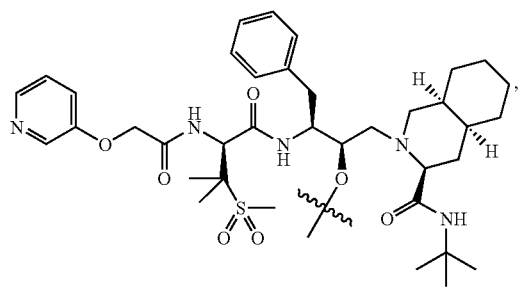
(x)
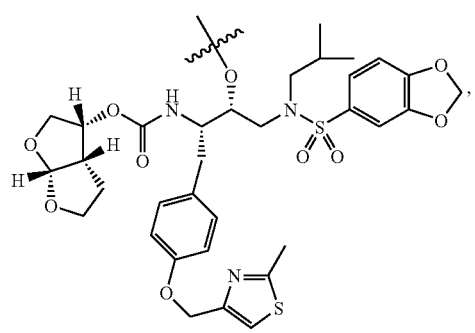
(xi)
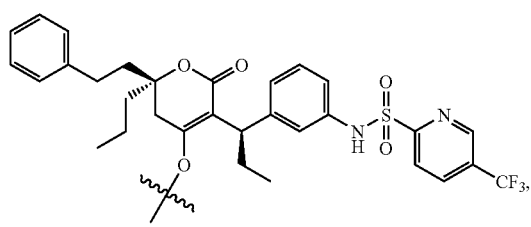
(xii)
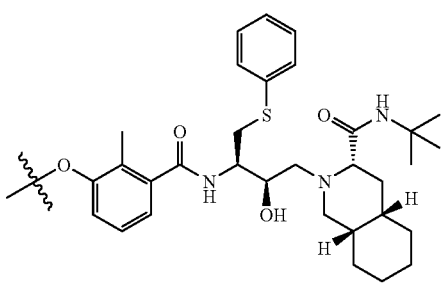
(xiii)
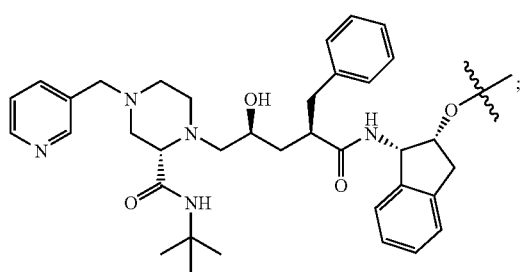
(xiv)
comprising
(a) contacting a compound of formula A-H, dialkyl sulfoxide having formula $(R_{91})_2SO$ wherein $R_{91}$ is alkyl, an acid, and an acid anhydride, to provide a compound of formula (2A),

A-L$_2$-SR$_{91}$ (2A)

and (b) contacting a compound of formula (2A), phosphoric acid, a reagent 1, and with or without a dehydrating reagent, in a solvent.

Examples of the dialkyl sulfoxide in step (a) include, but are not limited to, dimethyl sulfoxide, diethyl sulfoxide and dibutyl sulfide.

Examples of the acid anhydride in step (a) include, but are not limited to, acetic anhydride, propionic anhydride and benzoic anhydride.

Examples of the acid in step (a) include acetic acid, propionic acid, and benzoic acid.

The reaction of step (a) can be performed at a temperature from about 20° C. to about 50° C., preferably at about 20° C. to about 30° C.

The reaction of step (a) can be performed by contacting about one mole of a compound of formula A-H, about 30 moles of acid, about 10-15 moles of dialkyl sulfoxide, and about 10 moles of acid anhydride, to provide a compound of formula A-L$_2$-SR$_{91}$, wherein A, L$_2$ and R$_{91}$ are defined as in hereinabove. In another embodiment, the reaction of step (a) can be performed by contacting about one mole of a compound of formula A-H, about 20 moles of acid, about 26 moles of dialkyl sulfoxide, and about 5-10 moles of acid anhydride, to provide a compound of formula A-L$_2$-SR$_{91}$, wherein A, L$_2$ and R$_{91}$ are defined as hereinabove.

For example, the sixth embodiment provides a process for the preparation of a compound of formula (I), comprising contacting about one mole of a compound of formula A-H, about 30 moles of acetic acid, about 10-15 moles of dialkyl sulfoxide, and about 10 moles of acetic anhydride, to provide a compound of formula A-L$_2$-SR$_{91}$, wherein A, L$_2$ and R$_{91}$ are as defined, to provide a compound of formula A-L$_2$-SR$_{91}$, and (b) contacting the compound of formula A-L$_2$-SR$_{91}$, phosphoric acid, a reagent 1, and with or without a dehydrating agent, in a solvent.

For example, the sixth embodiment provides a process for the preparation of a compound of formula (I), comprising contacting about one mole of a compound of formula A-H, about 20 moles of acetic acid, about 26 moles of dialkyl sulfoxide, and about 5-10 moles of acetic anhydride, to provide a compound of formula A-L$_2$-SR$_{91}$, wherein A, L$_2$ and R$_{91}$ are as defined, to provide a compound of formula A-L$_2$-SR$_{91}$, and (b) contacting the compound of formula A-L$_2$-SR$_{91}$, phosphoric acid, a reagent 1, and with or without a dehydrating agent, in a solvent.

Examples of reagents 1 include, in step (b) but are not limited to, N-iodosuccinimide, N-chlorosuccinimide, N-bromosuccinimide, iodonium dicollidine triflate, methyl iodide, AgNO$_3$ and trimethylsilyl chloride. Preferred reagent 1 is N-iodosuccinimide.

Examples of the dehydrating agents in step (b) include, but are not limited to, molecular sieves, magnesium sulfate, Na$_2$SO$_4$, and K$_2$CO$_3$.

The solvent used in step (b) refers to any organic solvent that will allow the reaction in step (b) to proceed to completion or substantially completion. Examples of the solvents for the reaction in step (b) include, but are not limited to, tetrahydrofuran, N,N-dimethylformamide, ethyl acetate, acetonitrile, dichloromethane and dichloroethane.

The reaction of step (b) can be performed at a temperature from about −40° C. to about room temperature, preferably at about −20° C. to about room temperature, more preferably at about −10° C. to about 25° C., and most preferably at about −10° C. to about 10° C.

For example, the sixth embodiment provides a process for the preparation of a compound of formula (I), wherein in step (a) the acid is acetic acid, and the acid anhydride is acetic anhydride; and in step (b) the reagent 1 is N-iodosuccinimide.

For example, the sixth embodiment provides a process for the preparation of a compound of formula (I), wherein in step (a) the acid is acetic acid, the acid anhydride is acetic anhydride, and the dialkyl sulfoxide is dimethylsulfoxide; and in step (b) the reagent 1 is N-iodosuccinimide.

For example, the sixth embodiment provides a process for the preparation of a compound of formula (I), comprising (a) contacting about 1 mole of a compound of formula A-H, about 30 moles of acetic acid, about 10-15 moles of dialkyl sulfoxide, and about 10 moles of acetic anhydride at a temperature of about 20° C. to about 50° C., to provide a compound of formula A-L$_2$-SR$_{91}$, wherein R$_{91}$ is alkyl, and (b) contacting a compound of formula A-L$_2$-SR$_{91}$, phosphoric acid, N-iodosuccinimide, and with or without a dehydrating agent, in a solvent such as tetrahydrofuran or N,N-dimethylformamide, at a temperature of about −20° C. to about 25° C.

For example, the sixth embodiment provides a process for the preparation of a compound of formula (I), comprising (a) contacting about 1 mole of a compound of formula A-H, about 20 moles of acetic acid, about 26 moles of dialkyl sulfoxide, and about 5-15 moles of acetic anhydride at a temperature of about 20° C. to about 50° C., to provide a compound of formula A-L$_2$-SR$_{91}$, wherein R$_{91}$ is alkyl, and (b) contacting a compound of formula A-L$_2$-SR$_{91}$, phosphoric acid, N-iodosuccinimide, and with or without a dehydrating agent, in a solvent such as tetrahydrofuran or N,N-dimethylformamide, at a temperature of about −20° C. to about 25° C.

For example, the sixth embodiment provides a process for the preparation of a compound of formula (I), comprising (a) contacting about 1 mole of a compound of formula A-H, about 20 moles of acetic acid, about 26 moles of dialkyl sulfoxide, and about 5-15 moles of acetic anhydride at a temperature of about 20° C. to about 30° C., to provide a compound of formula A-L$_2$-SR$_{91}$, wherein R$_{91}$ is alkyl, and (b) contacting a compound of formula A-L$_2$-SR$_{91}$, phosphoric acid, N-iodosuccinimide, and with or without a dehydrating agent, in a solvent such as tetrahydrofuran or N,N-dimethylformamide, at a temperature of about −20° C. to about 25° C.

For example, the sixth embodiment provides a process for the preparation of a compound of formula (I), comprising (a) contacting about 1 mole of a compound of formula A-H, about 20 moles of acetic acid, about 26 moles of dimethyl sulfoxide, and about 5-15 moles of acetic anhydride at a temperature of about 20° C. to about 30° C., to provide a compound of formula A-L$_2$-SR$_{91}$, wherein R$_{91}$ is alkyl, and (b) contacting a compound of formula A-L$_2$-SR$_{91}$, phosphoric acid, N-iodosuccinimide, and with or without a dehydrating agent, in a solvent such as tetrahydrofuran or N,N-dimethylformamide, at a temperature of about −20° C. to about 25° C.

In a seventh embodiment, the present invention also relates to intermediates having formula A-L$_2$-SR$_{90}$ or A-L$_2$-SR$_9$, wherein A is

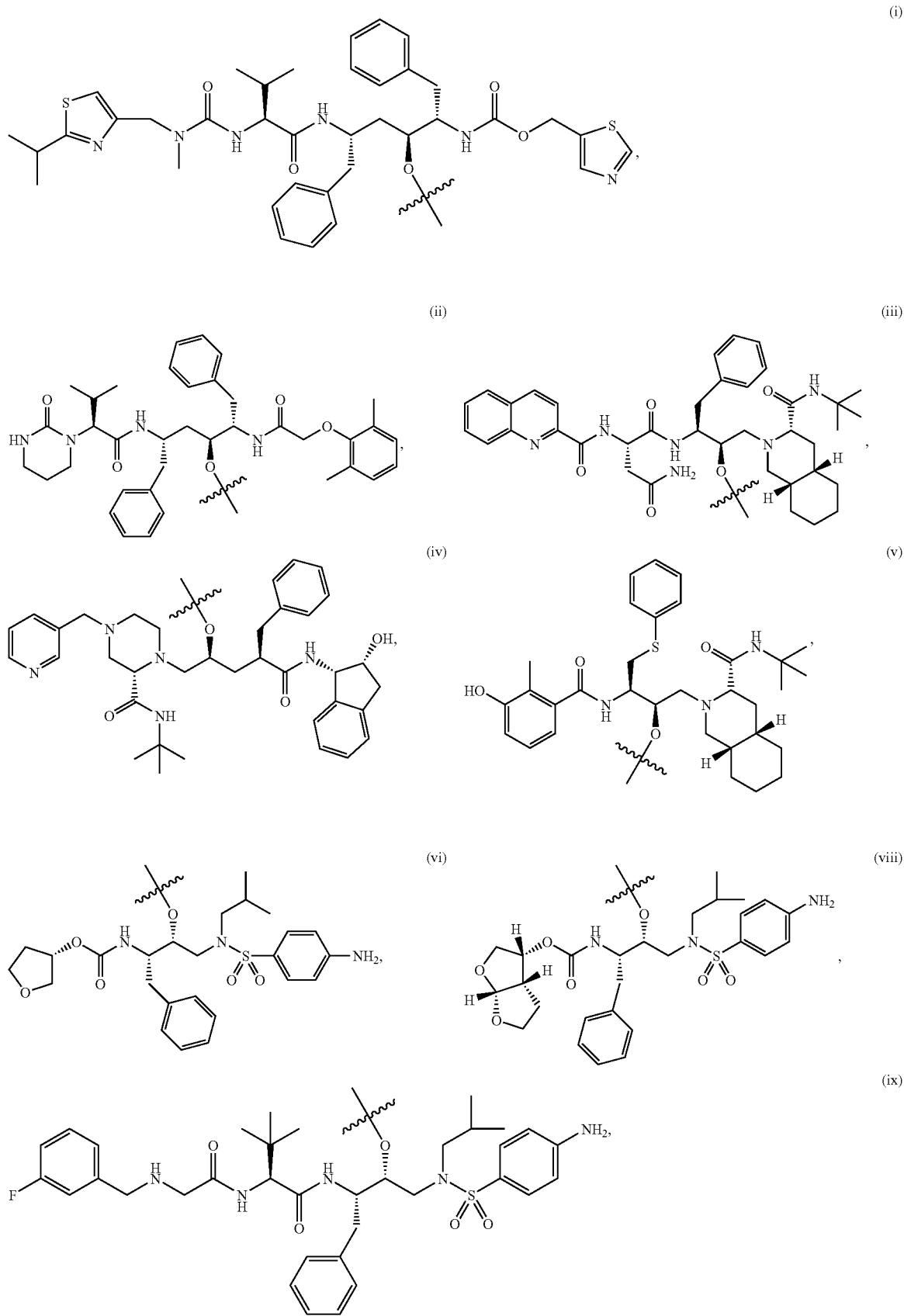

-continued

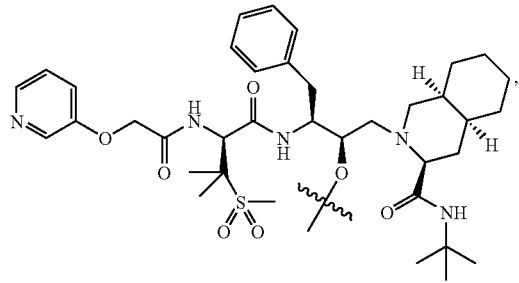
(x)

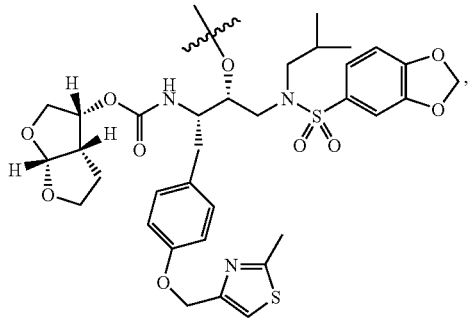
(xi)

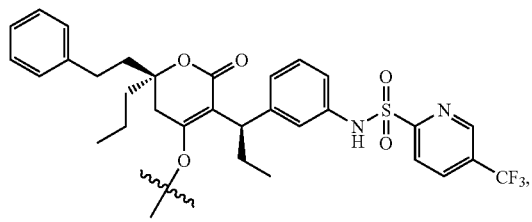
(xii)

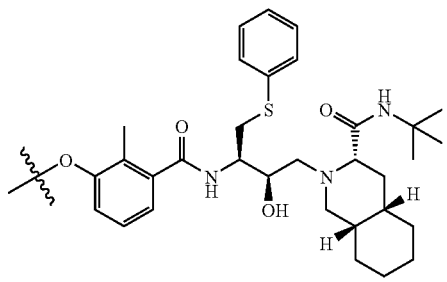
(xiii)

or

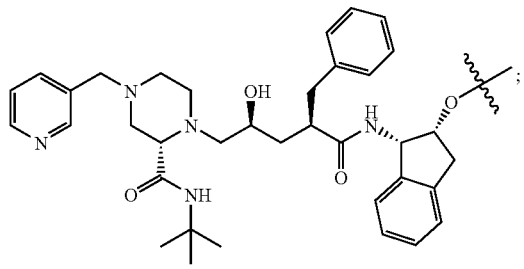
(xiv)

$L_2$ is —$(CR_1R_2)_m$—,
m is 1;
$R_1$ is selected from the group consisting of hydrogen and $C_1$-$C_{12}$ alkyl;
$R_2$ is selected from the group consisting of hydrogen and $C_1$-$C_{12}$ alkyl;
$R_{90}$ is alkyl; and
$R_{91}$ is alkyl.

Examples of $R_{90}$ and $R_{91}$ include, but are not limited to, methyl, ethyl, n-butyl and isobutyl (2-methylpropyl).

For example, the seventh embodiment provides an intermediate having formula A-$L_2$-$SR_{90}$ or A-$L_2$-$SR_{91}$, wherein $R_1$ and $R_2$ are hydrogen, and $R_{90}$ and $R_{91}$ are methyl.

For example, the sixth embodiment provides an intermediate having formula A-$L_2$-$SR_{90}$ or A-$L_2$-$SR_{91}$, wherein $R_1$ is hydrogen, $R_2$ is $C_1$-$C_{12}$ alkyl, $R_{90}$ is $C_1$-$C_{12}$ alkyl, and $R_{91}$ is $C_1$-$C_{12}$ alkyl.

For example, the seventh embodiment provides an intermediate having formula A-$L_2$-$SR_{90}$ or A-$L_2$-$SR_{91}$, wherein $R_1$ is hydrogen, $R_2$ is methyl, n-propyl or 1-methylethyl, $R_{90}$ is ethyl, n-butyl or isobutyl (2-methylpropyl), and $R_{91}$ is ethyl, n-butyl or isobutyl (2-methylpropyl).

Exemplary compounds of formula A-$L_2$-$SR_{90}$ or A-$L_2$-$SR_{91}$ include, but are not limited to, $N^1$-((1S,3S,4S)-1-benzyl-3-[(methylthio)methoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, (2S)—N-{(1S,3S,4S)-1-benzyl-4-{[(2,6-dimethylphenoxy)acetyl]amino}-3-[(methylthio)methoxy]-5-phenylpentyl}-3-methyl-2-(2-oxotetrahydropyrimidin-1(2H)-yl)butanamide, $N^1$-((1S,3S,4S)-1-benzyl-3-[1-(ethylthio)ethoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, (2S)—N-{(1S,3S,4S)-1-benzyl-4-{[(2,6-dimethylphenoxy)acetyl]amino}-3-[1-(ethylthio)ethoxy]-5-phenylpentyl}-3-methyl-2-(2-oxotetrahydropyrimidin-1(2H)-yl)butanamide, $N^1$-((1S,3S,4S)-1-benzyl-3-[1-(butylthio)butoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, and $N^1$-((1S,3S,4S)-1-benzyl-3-[1-(isobutylthio)-2-methylpropoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide.

The compounds of the invention can comprise of asymmetrically substituted carbon atoms known as chiral centers. These chiral centers are designated as "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The compounds of this invention may exist as single stereoisomers (e.g., single enantiomers or single diastereomer), mixtures of stereoisomers (e.g. any mixture of enantiomers or diastereomers) or racemic mixtures. All such single stereoisomers, mixtures and racemates are intended to be encompassed within the scope of the invention. Compounds identified herein as single stereoisomers are meant to describe compounds that are present in a form that are substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral carbons present in the chemical structures illustrated herein is not specified, the chemical structure is intended to encompass compounds containing either stereoisomer of each chiral center present in the compound.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate optically pure (enantiomerically pure) or substantial optically pure materials and synthetic reactions which do not cause racemization or inversion of stereochemistry at the chiral centers. Mixtures of stereoisomers of compounds, including racemic mixtures, resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography or crystallization/re-crystallization. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

Alternatively, salts of the enantiomers in the mixture can be prepared by any suitable method known in the art, including treatment of the carboxylic acid with a suitable optically pure base such as, but are not limited to, alkaloids and phenethylamine, followed by precipitation or crystallization/re-crystallization of the enantiomerically pure salts. Methods mentioned herein above and other useful methods for the resolution/separation of a mixture of stereoisomers, including racemic mixtures, may be found in "*Enantiomers, Racemates, and Resolutions,*" J. Jacques et al., 1981, John Wiley and Sons, New York, N.Y., the disclosure of which is incorporated herein by reference.

The compounds of this invention may possess one or more unsaturated carbon-carbon double bonds. All double bond isomers, both the cis (Z) and trans (E) isomers, and mixtures thereof are intended to be encompassed within the scoped of the present invention. Where a compound exists in various tautomeric forms, a recited compound is not limited to any one specific tautomer, but rather is intended to encompass all tautomeric forms.

The term "therapeutically acceptable salt" or "pharmaceutically acceptable salt" is intended to describe a zwitterions or a salt derived from pharmaceutically acceptable inorganic and organic acids and bases, and retains the biological effectiveness of the free acid or base of the specified compound without undue toxicity, irritation, and allergic response, commensurate with a reasonable benefit/risk ratio, effective for their intended use and is not biologically or otherwise undesirable; and as used herein, the term "therapeutically acceptable salt" or "pharmaceutically acceptable salt" refers to salts that are well known in the art. For example, S. M Berge et al. describe pharmaceutically acceptable salts in detail in *J. Pharmaceutical Sciences,* 66:p 1-19, 1977).

Accordingly, it is understood that the invention encompasses acid addition salts of Formula (I), (II) or (III) if an inventive compound contains a basic moiety. The desired salt may be prepared by any suitable method known in the art, including treatment of the free base with an inorganic acid such as, but are not limited to, hydrochloric acid, hydrobromic acid, sulfuric acid, nitric acid, and phosphoric acid, or with an organic acid such as, but are not limited to, acetic acid, trichloroacetic acid, trifluoroacetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid, alpha-hydroxy acid such as citric acid or tartaric acid, amino acid such as aspartic acid or glutamic acid, aromatic acid such as benzoic acid or cinnamic acid, sulfonic acid such as p-toluenesulfonic acid, methanesulfonic acid, ethanesulfonic acid or the like. Examples of therapeutically acceptable acid addition salts include acetates, acrylates, adipates, alginates, aspartates, benzenesulfonates, benzoates, bisulfates, bisulfites, bromides, butyne-1,4-dioates, butyrates, camphorates, camphorsulfonates, caproates, caprylates, chlorides, chlorobenzoates, citrate, decanoates, digluconate, dinitrobenzoates, formates, fumarates, glutamates, glycerophosphate, glycollates, hemisulfate, heptanoates, hexanoates, hexyne-1,6-dioates, hydroxybenzoates, γ-hydroxybutyrates, iodides, isethionate, isobutyrates, lactates, mandelates, malonates, maleates, methanesulfonates, methoxybenzoates, methylbenzoates, naphthylenesulfonate, nicotinates, oxalates, pamoates, pectinates, persulfates, phenylacetates, phenylbutrates, phenylpropionates, phthalates, phosphates, picrates, pivalates, propanesulfonates, propionates, propiolates, p-toluenesulfonates, pyrosulfates, sebacates, suberates, succinates, sulfates, sulfites, tartrates, trichloroacetates, trifluoroacetates, undecanoates, and the like. Also, the basic nitrogen-containing groups can be quaternized with such agents as acids (for example, hydrochloric acid, hydrobromic acid, trifluoroacetic acid or acetic acid), loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Compounds of the present invention may contain an acid moiety such as a carboxyl group, it is understood that the invention also encompasses the base addition salts. Such a desired salt may be prepared by any suitable method known to the art, including treatment of the free acid with an inorganic or organic base, such as amine (primary, secondary, or tertiary), an alkali metal or alkaline earth metal hydroxide, carbonates, bicarbonates or the like. Illustrative examples of suitable base addition salts include organic salts derived from amino acids such as glycine and arginice, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Representative examples of the prodrugs of the present invention have high aqueous solubility and metabolized in vivo to release the active parent drug. Such characteristics result in an approximately equal or greater bioavailability of the drug and in turn, reduce the pill burden on a patient.

Accordingly, in an eighth embodiment, the present invention provides the use of a compound or combination of compounds of having formula (I), (II) or (III), or a therapeutically acceptable salt, or combination thereof, to prepare a medicament for the treatment of HIV infection in a patient.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, BCH-189, AzdU, carbovir, ddA, d4C, d4T (stavudine), 3TC (lamivudine) DP-AZT, FLT (fluorothymidine), BCH-189, 5-halo-3'-thia-dideoxycytidine, PMEA, bis-POMPMEA, zidovudine (AZT), MSA-300, trovirdine, R82193, L-697, 661, BI-RG-587 (nevirapine), abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125 and the like), retroviral protease inhibitors (for example, HIV protease inhibitors such as ritonavir, lopinavir, saquinavir, amprenavir (VX-478), fosamprenavir, nelfinavir (AG1343), tipranavir, indinavir, atazanavir, TMC-126, TMC-114, mozenavir (DMP-450), JE-2147 (AG1776), L-756423, RO0334649, KNI-272, DPC-681, DPC-684, GW640385X, SC-52151, BMS 186,318, SC-55389a, BILA 1096 BS, DMP-323, KNI-227, and the like), HEPT compounds, L,697, 639, R82150, U-87201E and the like), HIV integrase inhibitors (S-1360, zintevir (AR-177), L-870812 L-870810 and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclor, castanosperminem rCD4/CD4-IgG, CD4-PE40, butyl-DNJ, hypericin, oxamyristic acid, dextran sulfate and pentosan polysulfate. Other agents that can be administered in combination with the compound of the present invention include HIV entry/fusion inhibitor (for example, enfuvirtide (T-20), T-1249, PRO2000, PRO542, PRO140, AMD-3100, BMS-806, FP21399, GW873140, Schering C(SCH-C), Schering D (SCH-D), TNX-355, UK-427857, and the like) and HIV budding/maturation inhibitor such as PA-457. Immunomodulators that can be administered in combination with the compound of the present invention include bropirimine, Ampligen, anti-human alpha interferon antibody, colony stimulating factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, cyclosporin, rapamycin, FK-565, FK-506, G-CSF, GM-CSF, hyperthermia, isopinosine, IVIG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24)) can be used in combination with the compound of the present invention.

Other agents that can be used in combination with the compound of this invention are ansamycin LM 427, apurinic acid, ABPP, Al-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenyloin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflomithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Other agents that can be used in combination with the compound of this invention are drugs for treating erectile dysfunction such as sildenafil, vardenafil and tadalafil.

In a ninth embodiment, the present invention provides a pharmaceutical composition comprising a therapeutically effective amount of a compound or combination of compounds of formula (I), (II) or (III), or a pharmaceutical salt thereof, and a pharmaceutically acceptable carrier.

For example, the present invention provides a pharmaceutical composition comprising a therapeutically effective amount of disodium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, and a pharmaceutically acceptable carrier.

For example, the present invention provides a pharmaceutical composition comprising a therapeutically acceptable amount of disodium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, and a pharmaceutically acceptable carrier.

For example, the present invention provides a pharmaceutical composition comprising a therapeutically acceptable amount of disodium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate, and a pharmaceutically acceptable carrier.

For example, the present invention provides a pharmaceutical composition comprising a therapeutically acceptable amount of disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate, and a pharmaceutically acceptable carrier.

In a tenth embodiment, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier.

For example, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier, wherein the second HIV protease inhibitor is selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X.

For example, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier, wherein the HIV reverse transcriptase inhibitor is selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125.

For example, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier wherein the HIV entry/fusion inhibitor is selected from the group consisting of enfuvirtide (T-20), T-1249, PRO2000, PRO542, PRO140, AMD-3100, BMS-806, FP21399, GW873140, Schering C(SCH-C), Schering D (SCH-D), TNX-355 and UK-427857.

For example, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier wherein the HIV integrase inhibitor is selected from the group consisting of S-1360, zintevir (AR-177), L-870812 and L-870810.

For example, the present invention provides a pharmaceutical composition comprising a therapeutically effective amount of a compound or combination of compounds having formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier wherein the HIV budding/maturation inhibitor is PA-457.

For example, a compound of this invention can be administered in combination with ritonavir. Such a combination is especially useful for inhibiting HIV protease in a human. Such a combination is also especially useful for inhibiting or treating an HIV infection in a human. When used in such a combination the compound of this invention and ritonavir can be administered as separate agents at the same or different times or they can be formulated as a single composition comprising both compounds.

One examples of such combination can comprise of a compound, or combination of compounds of the present invention with ritonavir and one or more reverse transcriptase inhibitors (for example, lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150 TMC-120, TMC-125 and the like). Yet another combination can comprise of a compound, or combination of compounds of the present invention with ritonavir and one or more HIV entry/fusion inhibitors. Such combinations are useful for inhibiting or treating an HIV infection in a human. When used in such a combination, the compound or combination of compounds of the present invention, ritonavir, and one or more agents selected from the group consisting of reverse transcriptase inhibitors and HIV entry/fusion inhibitors, can be administered as separate agents at the same or different times or they can be formulated as compositions comprising two or more of the compounds.

Examples of compounds of the present invention that can be used in any one of the pharmaceutical compositions or combination drug therapies as described hereinbefore include, but are not limited to, disodium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

calcium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

disodium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

calcium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

disodium $N^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

calcium $N^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

disodium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

calcium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

disodium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

calcium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide;

disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate;

calcium disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate;

disodium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate;

calcium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate;

disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate;

calcium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate;

disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate; and calcium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate.

It has been discovered that ritonavir is an inhibitor of the metabolic enzyme cytochrome P450 monooxygenase. Some drugs and, in particular, some HIV protease inhibitors are metabolized by cytochrome P450 monooxygenase, leading to unfavorable pharmacokinetics. It has been discovered that coadministration of ritonavir with a drug which is metabolized by cytochrome P450 monooxygenase causes an improvement in the pharmacokinetics (i.e., increases half-life, increases the time to peak plasma concentration, increases blood levels) of the drug.

Examples of drugs which are metabolized by cytochrome P450 monooxygenase and which benefit from coadministration with ritonavir or compounds of formula (I) (II) or (III) wherein A is ritonavir, include the immunosuppressants cyclosporine, FK-506, FK-565, and rapamycin, the chemotherapeutic agents (e.g. taxol and taxotere), the antibiotic clarithromycin, the HIV protease inhibitors such as lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, SC-52151, BMS 186,318, SC-55389a, BILA 1096 BS, DMP-323, KNI-227, and the like, and other therapeutic agents such as capravirine, calanolide, sildenafil, vardenafil and tadalafil.

It is also envisioned that prodrugs of ritonavir, such as the compounds of formula (I), (II) or (III) wherein A is ritonavir, with improved bioavailability and solubility, can be used in combination with a drug that is metabolized by cytochrome P450 monooxygenase (such as those that are listed hereinabove), thereby increasing the blood levels or improving the pharmacokinetics of such drug, when such a combination is administered to a patient in need of such treatment.

In an eleventh embodiment, the present invention provides a method for inhibiting cytochrome P450 monooxygenase comprising administering to a human in need thereof an amount of a compound of formula (I), (II) or (III), wherein A is ritonavir, to inhibit cytochrome P450 monooxygenase.

Accordingly, in a twelfth embodiment, the present invention provides a method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and a compound of formula (I), (II) or (III), or a pharmaceutically acceptable salt thereof, wherein A is ritonavir. Specifically, the invention provides a method for improving the pharmacokinetics of an HIV protease inhibitor (or a pharmaceutically acceptable salt thereof) which is metabolized by cytochrome P450 monooxygenase comprising administering to a human in need of such treatment a therapeutically effective amount of a combination of said HIV protease inhibitor or a pharmaceutically acceptable salt thereof and a compound of formula (I), (II) or (III), or a pharmaceutically acceptable salt thereof, wherein A is ritonavir. Such a combination of ritonavir prodrug or a pharmaceutically acceptable salt thereof and an HIV protease inhibitor or a pharmaceutically acceptable salt thereof which is metabolized by cytochrome P450 monooxygenase is useful for inhibiting HIV protease activity in mammals and is useful for inhibition, treatment or prophylaxis of an HIV infection or AIDS (acquired immune deficiency syndrome) in mammals.

In a thirteenth embodiment, the present invention provides a method for increasing human blood levels of a drug which is metabolized by cytochrome P450 monooxygenase comprising administering to a human in need of such treatment a therapeutically effective amount of a combination of said drug or a pharmaceutically acceptable salt thereof and a compound of formula (I), (II) or (III), or a pharmaceutically acceptable salt thereof, wherein A is ritonavir.

Examples of ritonavir prodrugs that can be used to inhibit cytochrome P450 monooxygenase, and therefore is useful in increasing the human blood levels or improving the pharmacokinetics of a drug that is metabolized by cytochrome P450 monooxygenase when such a drug and the ritonavir prodrug is administered to a human, include, but are not limited to, disodium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, calcium $N^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, disodium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, calcium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, disodium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, calcium $N^1$-((1S,3S,4S)-1-benzyl-5-phenyl-3-[1-(phosphonatooxy)butoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, disodium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide, and calcium $N^1$-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The present invention further provides methods for inhibiting HIV protease activity and methods for treating conditions responsive to HIV protease inhibition, in particular, HIV infection in a patient by administering to a patient in need of such treatment a therapeutically effective amount of a compound, or combination of compounds of formula (I), (II) or (III).

The term "treating" as used herein, refers to reversing, alleviating, inhibiting the progress of, or preventing the disorder or condition, or one or more symptoms of such disorder or condition to which such term applies. The term "treatment", as used herein, refers to the act of treating, as "treating" is defined immediately above.

The term "patient" refers to any individual treated with a compound of the present invention, or a therapeutically acceptable salt as defined herein. Patients include humans, as well as other animals such as companion animals (e.g. dogs and cats) and livestock. Patients may be experiencing one or more symptoms of a condition responsive to HIV protease inhibition (e.g., decline in CD4 cell levels or AIDS-associated opportunistic infections) or may be free of such symptom(s) (i.e. treatment may be prophylactic).

In a further aspect, the present invention also provides methods for inhibiting HIV protease activity and methods for treating conditions responsive to HIV protease inhibition, in particular, HIV infection in a patient by administering to a patient in need of such treatment a therapeutically effective amount of a compound, or combination of compounds of formula (I), (II) or (III), and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor. In yet another aspect, the invention provides methods for inhibiting HIV protease activity and methods for treating conditions responsive to HIV protease inhibition, in particular, HIV infection in a patient by administering to a mammal in need of such treatment any one of the pharmaceutical compositions described hereinabove.

In accordance with methods of treatment and pharmaceutical compositions of the invention, the compounds of formula (I), (II) or (III), or pharmaceutically acceptable salt thereof, can be administered alone or be administered in the form of a pharmaceutical composition in which the compound of Formula (I), (II) or (III), or a pharmaceutically acceptable salt, or combination thereof, in combination with a pharmaceutically acceptable carriers, adjuvants, diluents, vehicles, or combinations thereof.

The term "pharmaceutically acceptable carrier, adjuvants, diluents or vehicles" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be formulated in a conventional manner using one or more of the aforementioned pharmaceutically acceptable carriers. Thus the compounds of the present invention or its therapeutically acceptable salt, may be administered to humans and other mammals in solid or liquid form, orally, rectally, parenterally, intracisternally, intravaginally, topically (as by powders, ointments, drops, inhalants, spray, transdermal patch, and the like), or bucally. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions that can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin); f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Alternatively, the compounds or the pharmaceutically acceptable salt of this invention may be used in vaccines for protecting individuals against viral infection. The compounds or its pharmaceutically acceptable salt may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against HIV infection.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated; the treatment desired; the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds having Formula (I), or a therapeutically acceptable salt thereof, administered to a human or other mammal may range from about 0.003 to about 50 mg/kg/day. For purposes of oral administration, more preferable doses can be in the range of from about 0.1 to about 30 mg/kg/day. If desired, the effective daily dose can be divided into multiple doses for purposes of administration;

consequently, single dose compositions may contain such amounts or submultiples thereof to make up the daily dose.

Pharmacokinetics and Solubility Analysis

The improved pharmacokinetics and solubility of representative compounds of the present invention can be demonstrated by the test methods described below:

Solubility: Approximately 5 mg of each compound was weighed into 2 mL glass vials. Triplicate samples were prepared. One milliliter of distilled, deionized water purified by a Milli Q filtration system was added, and the samples were vortex mixed and sonicated. Vials were wrapped in aluminum foil to protect from light and equilibrated by tumbling in a water bath maintained at 25° C. for 1 day. The pH of each sample was measured after equilibration. Samples were centrifuged, filtered and prepared for HPLC assay by dilution. Samples were assayed by HPLC using an Agilent 1100 series HPLC. Separation was achieved using a gradient method (35% to 90% acetonitrile against 25 mM potassium phosphate buffer, pH 8) through a Zorbax Eclipse XDB C18 column, 250×4.6 mm, 5 μm. The compounds were detected using a UV detector set at 215 nm. Solubility was calculated as determined by HPLC assay by comparison against a standard curve. Representative compounds of the present invention exhibit solubility in the range of >3.4 mg/mL to >5.6 mg/mL.

Calf Intestine Alkaline Phosphatase (CIAP) Assay: The phosphate prodrug (30 μM) and CIAP (0.000125 Units/μL) (GibcoBRI, Cat #18009-019 lot #107342, 25 Units/μL) in Tris buffer at pH=8.0 (400 μL, 10 mM) were incubated at 37 degrees for up to 30 minutes. An aliquot of the above dephosphorylation reaction mixture (80 μL) was quenched with a mixture of 50% acetonitrile in methanol (160 μL) at 0, 10, 20 and 30 minutes. The amount of parent present in these samples was determined either by HPLC or by LC-MS/MS, and the half life for conversion of the phosphate prodrug to the parent was obtained by fitting the percent of parent at various time points to the first order decay. Representative compounds of the present invention showed rapid conversion of the prodrugs to the parent compounds. Typical half lives of the representative prodrugs were in the range from about 7 minutes to about 34 minutes.

Pharmacokinetic Analysis: All prodrugs were formulated as 5 mg/mL solutions in 5% dextrose in water, and ritonavir for co-dosing was formulated as a 5 mg/mL solution in 5% dextrose containing 20% ethanol, 30% propylene glycol, and 2 equivalents of methanesulfonic acid. Sprague-Dawley-derived rats (male; 0.25 to 0.35 kg; n=3) and beagle dogs (male and female; 8 to 12 kg; n=3) received prodrug doses equivalent to 5 mg/kg of body weight doses of the parent (5 mg eq/kg) by oral gavage, with or without a prior 5 mg/kg dose of ritonavir by oral gavage. Alternatively, solid prodrugs or mixtures of solid prodrugs were added to capsules and dosed orally. Plasma samples, obtained as a function of time after dosing (rat, 10 time points over 8 h; dog, 12 time points over 12 h), were extracted into mixtures of ethyl acetate and hexane, concentrated and analyzed by reversed-phase HPLC with an internal standard. The plasma drug concentration of each sample was calculated by a least-squares linear regression analysis (unweighted) of the peak area ratio (parent/internal standard) of the spiked plasma standards versus concentration. $C_{max}$ was read directly from the observed plasma concentration versus time data, and the area under the plasma versus time curve was calculated by using the linear trapezoidal rule over a single-hour dosing interval. Representative compounds of the present invention showed approximately equal or greater area under the curve (AUC) when compared with the parent compound. Co-dosing representative prodrugs of lopinavir with ritonavir in rats and dogs showed approximately equal or higher plasma levels than those produced by dosing lopinavir/ritonavir both as parent compounds.

Representative prodrugs of lopinavir were also dosed with representative prodrugs of ritonavir. All combinations were dosed at 5 mg equivalents/kg of each prodrug. The prodrugs were combined as solids into a single capsule for dosing in dogs. Such combinations provided approximately equal or greater lopinavir AUC than those produced by dosing lopinavir/ritonavir both as parent compounds.

Synthetic Methods

Abbreviations which have been used in the descriptions of the schemes and the examples that follow are: DMF is N,N-dimethylformamide, DMSO is dimethylsulfoxide, THF is tetrahydrofuran, NMMO is 4-methylmorpholine N-oxide, HOBT is 1-hydroxybenzotriazole hydrate, DCC is 1,3-dicyclohexylcarbodiimide, EDAC is 1-(3-dimethylaminopropyl)-3-ethylcarbodiimide hydrochloride, DMAP is 4-(dimethylamino)pyridine and EtOAc is ethyl acetate.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, $L_1$, $L_2$, $R_1$, $R_2$, $R_3$, $R_4$, $M_a$, $M_b$, q and t are as defined above unless otherwise noted below.

This invention is intended to encompass compounds having formula (I), (II) or (III), when prepared by synthetic processes or by metabolic processes. Preparation of the compounds of the invention by metabolic processes includes those occurring in the human or animal body (in vivo) or processes occurring in vitro.

Compounds of the invention can be prepared according to the methods described in Schemes 1-4 as shown below.

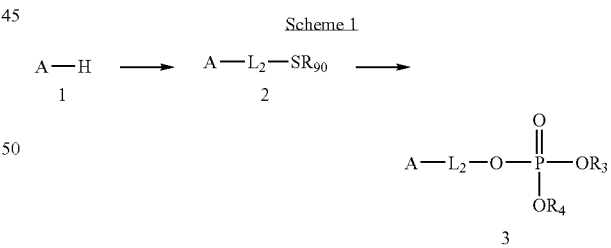

Lopinavir or ritonavir of formula (I) can be converted to alkylthioalkyl ethers of formula (2) wherein $R_{90}$ is alkyl, by reaction with an alkyl sulfide having formula $H-L_2-SR_{90}$, wherein $L_2$ is $CR_1R_2$, an oxidizing agent, and with or without a base. The reaction can be performed in a solvent such as, but is not limited to, acetonitrile or tetrahydrofuran, at a temperature from about −10° C. to about 50° C. Examples of alkyl sulfides include, but are not limited to, methyl sulfide, ethyl sulfide, butylsulfide and t-butyl methyl sulfide. Examples of suitable oxidizing agents include, but are not limited to, benzoyl peroxide, N-chlorosuccinimide and N-chloro-N-methylacetamide. Examples of bases include, but are not limited to, triethylamine, diisopropylethyl amine, tributylamine, morpholine and 1-methylimidazole. Alternatively, the thioethers of formula (2) can be prepared from an alkyl sulfoxide, such as dimethyl sulfoxide, and an acid anhydride such as acetic anhydride in a solvent such as acetonitrile, acetic acid or dimethyl sulfoxide at a temperature from about 20° C. to about 50° C. Compound (2) can also be prepared by treatment of lopinavir or ritonavir with a haloalkyl alkyl sulfide having formula $XL_2SR_{90}$, wherein X is Cl, Br, F or I, and $L_2$ is $(CR_1R_2)_m$, in the presence of a base in a solvent or in the presence of a silver salt such as $AgNO_3$. An example of a suitable haloalkyl alkyl sulfide includes, but is not limited to, chloromethyl methyl sulfide. Examples of suitable bases include, but are not limited to metal hydrides (for example sodium hydride and the like), lithium bis(trimethylsilyl)amide, sodium bis(trimethylsilyl)amide, and potassium bis(trimethylsilyl)amide. The reaction can be performed in a solvent such as, but not limited to, tetrahydrofuran, N,N-dimethylformamide or diethyl ether at a temperature from about −78° C. to about the reflux temperature of the solvent employed. Compounds having formula (2) can be reacted with phosphoric acid to provide compounds of formula (3) wherein $R_3$ and $R_4$ are hydrogen, or with the corresponding diester or monoester of the phosphoric acid to provide a compound of formula (3) wherein one or both of $R_3$ and $R_4$ are alkyl or benzyl and wherein $R_3$ and $R_4$ can be the same or different. The reaction is generally performed by contacting compounds of formula (2), reagent 1, and with or without a dehydrating reagent, in a solvent. Examples of reagents 1 include, but are not limited to, N-iodosuccinimide, N-chlorosuccinimide, N-bromosuccinimide, iodonium dicollidine triflate, methyl iodide, $AgNO_3$ and trimethylsilyl chloride. Examples of dehydrating agents include, but are not limited to, molecular sieves, magnesium sulfate, $Na_2SO_4$, and $K_2CO_3$. The reaction can be performed in a solvent such as, but not limited to, ethyl acetate, tetrahydrofuran, N,N-dimethylformamide or acetonitrile at a temperature from about −40° C. to about room temperature.

Scheme 2

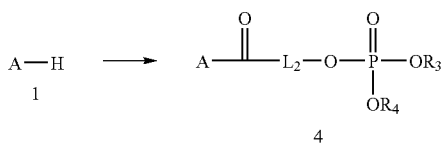

Lopinavir or ritonavir of formula A-H can be reacted with a carboxylic acid having formula (6) in the presence of a coupling reagent, in the absence or presence of a base, to provide compounds of formula (4) wherein $L_2$ is $(CR_1R_2)_m$. The reaction can be performed in a solvent such as tetrahydrofuran, N,N-dimethylformamide, or acetonitrile at a temperature from about 0° C. to about the reflux temperature of the solvent employed. Examples of coupling reagents include, but are not limited to, 1-ethyl-3-[3-(dimethylamino) propyl]-carbodiimide hydrochloride (EDAC), benzotriazol-1-yloxytripyrrolidinophosphonium hexafluorophosphate (PyBOP), 3-(diethoxyphosphoryloxy)-1,2,3-benzotriazin-4 (3H)-one (DEPBT), and 1,3-dicyclohexylcarbodiimide (DCC), with or without the addition of 1-hydroxybenzotriazole hydrate (HOBT) or N-hydroxysuccinimide. Examples of suitable bases include, but are not limited to 4-(dimethylamino)pyridine, triethylamine, diisopropylethylamine or pyridine. Alternatively, the compounds of formula (4) can be obtained by (a) treatment of the carboxylic acids with oxalyl chloride in the presence of a catalytic amount of N,N-dimethylformamide or with thionyl chloride and (b) reacting the product of step (a) with lopinavir or ritonavir in the presence of a base in a solvent such as tetrahydrofuran, N,N-dimethylformamide, or acetonitrile at a temperature of about 0° C. to about the reflux temperature of the solvent employed. Examples of suitable bases for step (b) include, but are not limited to, 4-(dimethylamino)pyridine, triethylamine, diisopropylethylamine or pyridine. Compounds of formula (4) wherein $R_3$ and $R_4$ are benzyl can be converted to compounds of formula (4) wherein $R_3$ and $R_4$ are H by reaction with hydrogen gas using catalysts such as palladium on carbon (Pd/C), palladium hydroxide on carbon, or platinum on carbon, in a solvent such as methanol, ethanol, tetrahydrofuran, dioxane or ethyl acetate, at a pressure from about 1 to about 5 atmospheres and a temperature from about 10° C. to about 60° C. Another alternative procedure employing the use of reagents such as ammonium formate and Pd/C in methanol at reflux temperature under an inert atmosphere (e.g., nitrogen or argon gas) is also effective. Compounds of formula (4) wherein $R_3$ and $R_4$ are tert-butyl can be converted to compounds of formula (4) wherein $R_3$ and $R_4$ are H by reaction with a suitable acid such as hydrochloric acid or trifluoroacetic acid. Compounds of formula (4) wherein $R_3$ and $R_4$ are methyl can be transformed to compounds of formula (4) wherein $R_3$ and $R_4$ are H by treatment with $BBr_3$, trimethylsiliyl bromide or trimethylsilyl iodide.

Scheme 3

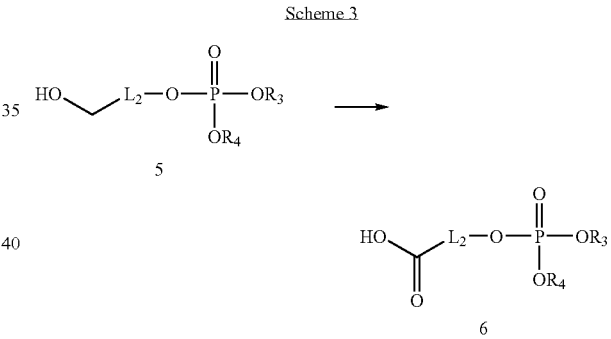

The carboxylic acids of formula (6) can be prepared from diols of formula $OH-CH_2(CR_1R_2)_m-OH$. The diols can be obtained from the corresponding diacids by reaction of the diacid with a reducing agent, in a suitable solvent such as, but not limited to, diethyl ether or tetrahydrofuran, at a temperature from about 0° C. to about 60° C. Examples of the reducing agents include, but are not limited to, lithium aluminum hydride or borane. Diols having formula $OH-CH_2(CR_1R_2)_m-OH$ can be converted to phosphate triesters of formula (5) wherein $L_2$, $R_3$ and $R_4$ are as defined in formula (I), by (a) reacting the diol with a phosphoramidite, such as dibenzyl diethylphosphoramidite or di-t-butyl diethylphosphoramidite, in the presence of 1H-tetrazole, in a solvent such as, but not limited to, tetrahydrofuran, dichloroethane, or dichloromethane, at a temperature from about 0° C. to about 25° C., and (b) reacting the product from step (a) with an oxidizing agent such as m-chloroperbenzoic acid, in a solvent such as tetrahydrofuran, dichloroethane, or dichloromethane, at a temperature from about −45° C. to about room temperature. Alternatively, diols having formula $OH-CH_2(CR_1R_2)_m-OH$ can be converted to phosphate triesters of formula (5) by reacting with a dialkyl chloridophosphate, such as dibenzyl chloridophosphate or di-t-butyl chloridophosphate, in the presence of a base, in a solvent such as, but not limited to, tetrahydrofuran or N,N-dimethylformamide. Examples of suitable bases include, but are not limited to, 4-(dimethylamino)pyridine, triethylamine, diisopropylethylamine, pyridine, metal hydrides (for example sodium hydride and the like), lithium bis(trimethylsilyl)amide, sodium bis(trimethylsilyl)amide, and potassium bis(trimethylsilyl)amide. Acids (6) can be obtained from (5) by reaction with an oxidizing agent in a suitable solvent such as N,N-dimethylformamide, tetrahydrofuran, or acetonitrile. Examples of oxidizing agents include, but are not limited to, pyridinium dichromate, $K_2MnO_4$, or $RuO_2/NaIO_4$. Alternatively a two-step oxidation can be employed by oxidation of (5) first to the corresponding aldehyde using Swern oxidation condition, pyridinium chlorochromate, tetrapropylammonium perruthenate (TPAP), or Dess-Marin periodinane, followed by oxidation of the corresponding aldehydes to the acids using $NaClO_2$.

Acids of formula (6) can also be prepared by (a) monosilylating diols of formula $OH-CH_2(CR_1R_2)_m-OH$ by reacting the diol with a silylating reagent in the presence of a base such as imidazole or triethyamine in a solvent such as tetrahydrofuran or N,N-dimethylformamide at a temperature from about 0° C. to about room temperature, (b) reacting products of step (a) with a phosphoramidite such as, but not limited to, dibenzyl diethylphosphoramidite or di-t-butyl diethylphosphoramidite, in the presence of 1H-tetrazole, followed by oxidation with an oxidizing agent such as m-chloroperbenzoic acid, or alternatively by reaction of the products of step (a) with a dialkyl chloridophosphate, such as dibenzyl chloridophosphate or di-t-butyl chloridophosphate, in the presence of a base, as described in the preceding paragraph, and (c) desilylation of the product of step (b) with a desilylating agent in a solvent such as tetrahydrofuran at a temperature from about 0° C. to about room temperature. Examples of the silylating agents include, but are not limited to, tert-butyldimethylsilyl chloride (TBSCl), tert-butyldiphenylsilyl chloride (TBDPSCl), or triethylsilyl chloride (TESCl). Examples of the desilylating agents include, but are not limited to, tetrabutylammonium fluoride (TBAF), and HF. Step (b) can be performed using the conditions for the transformation of the diols to compounds of formula (5) as described in the preceding paragraph.

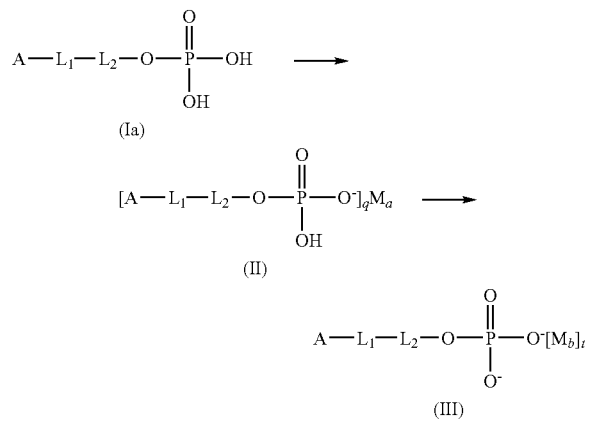

Compounds of formula (Ia) can be converted to salts of formula (II) or (III) by reacting with about one or two equivalents of a variety of inorganic and organic bases, either in situ or after isolation of the compound of formula (Ia) from reaction mixtures of scheme 1 or 2. The compounds of formula (III) can be obtained via a one step reaction or stepwise from compounds of formula (Ia). The reaction can be performed in aqueous solvent medium or in a suitable organic solvent such as methanol or ethanol. Typically the reaction is carried out at a temperature from about −10° C. to about 70° C. for about 5 minutes to about 48 hours. Upon evaporation of the solvent, the desired solid salt is obtained.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

Example 1

$N^1$-((1S,3S,4S)-1-benzyl-3-hydroxy-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide The synthesis of the title compound is described in Example 1U of U.S. Pat. No. 5,541,206.

Example 2 disodium $N^1$-((1S,3S,4S)-1-benzyl-5-phenyl-3-[(phosphonatooxy)methoxy]-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide Example 2A $N^1$-((1S,3S,4S)-1-benzyl-3-[(methylthio)methoxy]-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide To a solution of the compound of Example 1 (5.0 g, 6.9 mmol) and methyl sulfide (4.1 mL) in acetonitrile (35 mL) at 0° C. was added benzoyl peroxide (6.7 g) in four portions over 20 minutes, and the mixture was stirred at 0° C. for 1 hour and then at room temperature for 1 hour. The reaction was diluted with ethyl acetate and washed with 10% $Na_2CO_3$ and brine. The organic was dried over $MgSO_4$, filtered and evaporated. The residue was chromatographed on silica gel eluting with a gradient of 33-100% ethyl acetate in chloroform to give the title compound (4.56 g, 84% yield).

Example 2B disodium N¹-((1S,3S,4S)-1-benzyl-5-phenyl-3-[(phosphonatooxy)methoxy]-4-{[(1,3-thiazol-5-yl-methoxy)carbonyl]amino}pentyl)-N²-{[[(2-isopropyl-1,3-thiazol-4-yl)methyl](methyl)amino]carbonyl}-L-valinamide To a solution containing the product from Example 2A (4.56 g, 5.8 mmol), phosphoric acid (4.0 g), and molecular sieves (4 Å, 18 g) in THF (60 mL) at 0° C. was added N-iodosuccinimide (2.0 g), and the mixture was stirred at room temperature for 1 hour. The reaction mixture was filtered through celite, and washed with methanol. The filtrate was treated with 1 M $Na_2S_2O_3$ until it was clear, adjusted to pH 10 by addition of $Na_2CO_3$, and the precipitate was removed by filtration. The filtrate was concentrated under reduced pressure, and the residue was purified by HPLC using a C18 column, eluting with a gradient of 0-100% methanol in water to give the title compound (2.64 g, 52% yield). ¹H NMR (300 MHz, MeOH-$d_4$), δ ppm 0.81 (d, J=7.0 Hz, 3H), 0.86 (d, J=7.0 Hz, 3H), 1.35 (d, J=7.0 Hz, 6H), 1.64-1.73 (m, 1H), 1.89-2.03 (m, 2H), 2.60-2.90 (m, 4H), 2.98 (s, 3H), 3.24-3.28 (m, 1H), 3.63-3.67 (m, 1H), 4.02-4.09 (m, 2H), 4.20-4.30 (m, 1H), 4.46-4.64 (m, 2H), 4.95 (dd, J=5.3, 10.5 Hz, 1H), 5.10 (q, J=12.5 Hz, 2H), 5.10-5.15 (m, 1H), 7.07-7.21 (m, 11H), 7.77 (s, 1H), 8.93 (s, 1H).

Example 3

(2S)—N-((1S,3S,4S)-1-benzyl-4-{[(2,6-dimethylphenoxy)acetyl]amino}-3-hydroxy-5-phenylpentyl)-3-methyl-2-(2-oxotetrahydropyrimidin-1(2H)-yl)butanamide The synthesis of the title compound is described in Example 2 of U.S. Pat. No. 5,914,332.

Example 4

Disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate

Example 4A (2S)—N-{(1S,3S,4S)-1-benzyl-4-{[(2,6-dimethylphenoxy)acetyl]amino}-3-[(methylthio)methoxy]-5-phenylpentyl}-3-methyl-2-(2-oxotetrahydropyrimidin-1(2H)-yl)butanamide Method A To a solution of the compound of Example 3 (3.0 g, 4.8 mmol), DMSO (18 mL), and acetic acid (3.6 mL) at room temperature was added acetic anhydride (23 mL), and the reaction was stirred for 48 hours at room temperature. The reaction was quenched with ice and 10% $Na_2CO_3$ was added to adjust the pH to 7. The mixture was extracted with ethyl acetate and washed with 10% $Na_2CO_3$ and brine. The organic was dried over $Na_2SO_4$, filtered and evaporated to give the crude product, which was chromatographed on silica gel eluting first with 25-100% ethyl acetate in dichloromethane to give the title compound (2.1 g, 64% yield).

Method B

Example 3 (50.4 g, 0.080 mol), 85 mL DMSO (15 equivalents), 75 mL acetic anhydride (10 equivalents), 135 ml acetic acid (30 equivalents) were mixed at ambient temperature under nitrogen for 3 days. The reaction was quenched with 1500 mL aqueous 17% $Na_2CO_3$ pre-chilled to 0° C. The mixture was extracted with 1400 mL ethyl acetate and then with 500 mL ethyl acetate twice. The organic layers were combined and washed with 700 mL 10% $Na_2CO_3$, water 600 mL×3, and 500 ml saturated brine, sequentially. The organic layer was dried over $MgSO_4$, concentrated and chased with heptanes to give 56.4 g of title compound as white foam.

Example 4B

Disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate Method A To a solution containing the product from Example 4A (1.73 g, 2.5 mmol), phosphoric acid (1.23 g), and molecular sieves (4 Å, 8.6 g) in THF (25 mL) at room temperature was N-iodosuccinimide (1.13 g), and the mixture was stirred at room temperature for 2 hours. The reaction was diluted with methanol and filtered through celite. The filtrate was treated with 1 M $Na_2S_2O_3$ until it was clear, and adjusted to pH 9 by addition of 10% $Na_2CO_3$. The solids were removed by filtration through celite and the solvent was evaporated. The crude product was purified by HPLC using a C18 column, eluting with 0-100% methanol in water to give the title compound (1.19 g, 60% yield).

¹H NMR (300 MHz, MeOH-$d_4$), δ ppm 0.84 (d, J=6.6 Hz, 3H), 0.90 (d, J=6.6 Hz, 3H), 1.54-1.77 (m, 3H), 1.98-2.19 (m, 2H), 2.12 (s, 6H), 2.64-2.78 (m, 2H), 2.87-2.95 (m, 2H), 3.04-3.23 (m, 4H), 3.80 (dd, J=3.4, 10.3 Hz, 1H), 3.96-4.07 (m, 2H), 4.33 (d, J=11.0 Hz, 1H), 4.41-4.50 (m, 1H), 4.71 (dd, J=4.0, 10.6 Hz, 1H), 5.09 (dd, J=5.5, 8.1 Hz, 1H), 5.15 (dd, J=5.5, 8.8 Hz, 1H), 6.87-6.98 (m, 3H), 7.08-7.25 (m, 8H), 7.31-7.33 (m, 2H).

Method B 30.7 g crude Example 4A (89% purity, 0.0396 mol) was dissolved in 275 mL of anhydrous tetrahydrofuran under nitrogen. Phosphoric acid crystal (37 g, 0.378 mol) was added to the solution. The mixture was stirred at ambient temperature for 15 minutes and then cooled to 5° C. N-iodosuccinimide (14 g, 0.0622 mol) was added and the mixture was stirred at 5° C. for 1 hour. The reaction was quenched with 20 mL methanol. The mixture was treated with aqueous saturated $Na_2CO_3$ to pH 4-5. 13 ml of aqueous saturated $Na_2S_2O_5$ was added to remove the reddish-brown color. Water (95 mL) was added and the mixture was extracted with 1 liter of ethyl acetate then back extracted with 100 mL of ethyl acetate. The organic layers were combined and washed with saturated brine (250 g×3). To the organic layer was added 290 g of aqueous saturated $Na_2CO_3$, 1200 mL of heptanes, and 120 mL water with mixing. The aqueous layer was separated. 50 mL of water was added to the aqueous layer and the solution was washed with 360 mL of ethyl acetate/heptanes (1:1) to remove impurities. The aqueous layer was treated with 110 g of NaCl and extracted with 1100 mL of ethyl acetate. The organic layer was washed with 250 g of saturated brine and then extracted with 300 mL of water. The aqueous layer was treated with 0.5 g of $Na_2CO_3$, 55 g of NaCl and then extracted with 1500 mL of ethyl acetate. The organic layer was dried over Na$_2$SO$_4$, filtered and concentrated. The residue was dissolved in 400 mL of ethyl acetate at 70° C., filtered, concentrated and chased with heptanes to give white solid. The solid product was dried under vacuum at ambient temperature to give the title compound.

Example 5 disodium N$^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide

Example 5A

N$^1$-((1S,3S,4S)-1-benzyl-3-[1-(ethylthio)ethoxy]-5-phenyl-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide To a solution of the compound of Example 1 (0.50 g, 0.69 mmol) and ethyl sulfide (1.9 mL) in acetonitrile (5 mL) at 0° C. was added benzoyl peroxide (0.84 g) in three portions over 3 hours. The reaction was diluted with ethyl acetate and washed with 10% Na$_2$CO$_3$ and brine. The organic was dried over MgSO$_4$, filtered and evaporated. The residue was chromatographed on silica gel, eluting with a gradient of 50-100% ethyl acetate in chloroform to give the title compound (0.42 g, 75% yield).

Example 5B

Disodium N$^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide To a solution containing the product from Example 5A (0.15 g, 0.19 mmol), molecular sieves (4 Å, 0.60 g), and phosphoric acid (0.090 g) in DMF (4.5 mL) at 0° C. was added N-iodosuccinimide (0.084 g), and the mixture was stirred at 0° C. for 2 hours. The reaction was filtered through celite, washing with methanol. The filtrate was adjusted to pH 9 by addition of 10% Na$_2$CO$_3$ and treated with 1 M Na$_2$S$_2$O$_3$ until it was clear. The solvent was evaporated and the crude product was purified by HPLC using a C18 column, eluting with C18, eluting with a gradient of 0-100% methanol in water to give the title compound (0.080 g, 48% yield). $^1$H NMR (300 MHz, MeOH-d$_4$) δ ppm 0.84-0.99 (m, 6H), 1.33-1.39 (m, 9H), 1.44-1.71 (m, 1H), 1.95-2.11 (m, 1.5H), 2.20-2.35 (m, 0.5H), 2.55-2.97 (m, 4H), 3.01 (s, 3H), 3.22-3.27 (m, 1H), 3.74-3.84 (m, 0.5H), 3.90-4.02 (m, 1.5H), 4.07-4.16 (m, 1.5H), 4.21-4.31 (m, 0.5H), 4.42-4.63 (m, 2H), 4.91-4.96 (m, 1H), 5.07-5.12 (m, 1H), 5.31-5.38 (m, 0.5H), 5.42-5.48 (m, 0.5H), 6.94-7.25 (m, 11H), 7.65-7.73 (m, 1H), 8.90-8.92 (m, 1H).

Example 6

Disodium 1-[(((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate

Example 6A (2S)—N-{(1S,3S,4S)-1-benzyl-4-{[(2,6-dimethylphenoxy)acetyl]amino}-3-[1-(ethylthio)ethoxy]-5-phenylpentyl}-3-methyl-2-(2-oxotetrahydropyrimidin-1(2H)-yl)butanamide Method A To a solution of the compound of Example 3 (0.50 g, 0.80 mmol) and ethyl sulfide (2.1 mL) in acetonitrile (6 mL) at 0° C. was added benzoyl peroxide (1.16 g) in three portions over 3 hours. The reaction was diluted with ethyl acetate and washed with 10% Na$_2$CO$_3$ and brine. The organic was dried over MgSO$_4$, filtered and evaporated. The residue was chromatographed on silica gel eluting with a gradient of 50-100% ethyl acetate in chloroform to give the title compound (0.36 g, 61% yield).

Method B

A slurry of N-chlorosuccinimide (6.5 g, 48.7 mmol) in tetrahydrofuran (50 mL) was cooled to −10° C., followed by addition of diethyl sulfide (7.0 mL) and then by addition of a solution of Example 3 (5.0 g) in tetrahydrofuran (20 mL). A solution of triethylamine (9.0 mL) in tetrahydrofuran (15 mL) was then added dropwise and the mixture was stirred at −10° C. for 1.5 h. The reaction was quenched with 10% Na$_2$CO$_3$ and extracted twice with ethyl acetate. The combined organic was washed with water and brine and dried over MgSO$_4$, filtered and evaporated to give the crude product (7.5 g).

Example 6B

Disodium 1-[(((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate To a solution containing the product from Example 6A (0.15 g, 0.21 mmol), molecular sieves (4 Å, 0.60 g), and phosphoric acid (0.082 g) in DMF (4.5 mL) at 0° C. was added N-iodosuccinimide (0.094 g), and the mixture was stirred at 0° C. for 2 hours. The reaction was filtered through celite, washing with methanol. The filtrate was treated with 1 M Na$_2$S$_2$O$_3$ until it was clear, adjusted to pH 9 by addition of 10% Na$_2$CO$_3$. The solvent was evaporated, and the crude product was purified by HPLC using a C18 column, eluting with a gradient of 0-100% methanol in water to give the title compound (0.066 g, 39% yield). $^1$H NMR (300 MHz, MeOH-d$_4$) δ ppm 0.85 (d, J=6.6 Hz, 1.5H), 0.86 (d, J=6.6 Hz, 1.5H), 0.94 (d, J=6.6 Hz, 1.5H), 0.96 (d, J=6.6 Hz, 1.5H), 1.45 (d, J=5.1 Hz, 1.5H), 1.46 (d, J=5.1 Hz, 1.5H), 1.50-1.74 (m, 3H), 1.88-1.98 (m, 0.5H), 2.09-2.25 (m, 1.5H), 2.09 (s, 3H), 2.13 (s, 3H), 2.74-2.77 (m, 2H), 2.85-3.19 (m, 6H), 3.92-4.03 (m, 2.5H), 4.16-4.21 (m, 0.5H), 4.23 (d, J=11.0 Hz, 0.5H), 4.35 (d, J=11.0 Hz, 0.5H), 4.40-4.54 (m, 1H), 4.63-4.70 (m, 1H), 5.39-5.50 (m, 1H), 6.88-6.99 (m, 3H), 7.07-7.30 (m, 10H).

Example 7

Disodium(1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl phosphate

Example 7A dibenzyl(1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl phosphate A solution of the compound of Example 3 (0.250 g, 0.40 mmol), dibenzyl diethylphosphoramidite (0.28 mL), and 1H-tetrazole (0.14 g) in THF (4.0 mL) was stirred at room temperature for 68 hours. Dichloromethane (4.0 mL) was added and the mixture was cooled to −45° C., followed by addition of m-chloroperbenzoic acid (0.089 g). After stirring for 30 minutes at −45° C., the reaction was diluted with ethyl acetate and washed twice with 10% $Na_2CO_3$ and then with brine. The organic phase was dried over $MgSO_4$, filtered and evaporated. The residue was chromatography on silica gel, eluting with a gradient starting with 33% ethyl acetate in chloroform and ending with 5% methanol in ethyl acetate, to give the title compound (0.324 g, 90% yield).

Example 7B

Disodium(1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl phosphate To a solution of the product from Example 7A (0.320 g, 0.36 mmol) in a mixture of ethyl acetate (1.8 mL) and methanol (1.8 mL) was added Pd(OH)$_2$ on carbon (0.100 g, 20% by wt. Pd), and the mixture was stirred under an atmosphere of hydrogen (balloon pressure) for 16 hours. The reaction was filtered through celite and the solvent was evaporated. Methanol and water were added and the pH was adjusted to 9 by addition of 10% $Na_2CO_3$ solution, and purified by chromatography using a C18 column, eluting with a gradient starting with water and ending with methanol, to give the title compound (0.215 g, 79% yield). $^1$H NMR (300 MHz, MeOH-d$_4$), δ ppm 0.86 (d, J=6.6 Hz, 3H), 0.99 (d, J=6.6 Hz, 3H), 1.55-1.77 (m, 3H), 2.03-2.23 (m, 2H), 2.10 (s, 6H), 2.71 (d, J=7.4 Hz, 2H), 2.90-3.00 (m, 2H), 3.06-3.19 (m, 4H), 3.94 (q, J=14.3 Hz, 2H), 4.36-4.45 (m, 1H), 4.46 (d, J=11.0 Hz, 1H), 4.48-4.57 (m, 1H), 4.67-4.70 (m, 1H), 6.87-6.97 (m, 3H), 7.08-7.24 (m, 8H), 7.30-7.32 (m, 2H).

Example 8 disodium $N^1$-((1S,3S,4S)-1-benzyl-5-phenyl-3-(phosphonatooxy)-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide

Example 8A $N^1$-((1S,3S,4S)-1-benzyl-3-{[bis(benzyloxy)phosphoryl]oxy}-5-phenyl-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide A solution of the compound of Example 1 (6.0 g, 8.32 mmol), dibenzyl diethylphosphoramidite (3.96 g), and 1H-tetrazole (2.63 g) in THF (100 mL) was stirred at room temperature for 4 hours. The mixture was cooled to −45° C., followed by dropwise addition of a solution of m-chloroperbenzoic acid (7.2 g) in dichloromethane (100 mL). The mixture was warmed to room temperature and stirred for 1 hour. A 10% solution of $Na_2S_2O_3$ (100 mL) was added and the mixture was stirred for 30 minutes. The reaction mixture was extracted with ethyl acetate and washed with 10% $Na_2S_2O_3$ and saturated $NaHCO_3$. The organic phase was dried over $MgSO_4$, filtered and evaporated. The residue was chromatographed on silica gel, eluting with 2% methanol in dichloromethane containing 0.05% $NH_4OH$, to give the title compound (6.2 g, 76% yield).

Example 8B disodium $N^1$-((1S,3S,4S)-1-benzyl-5-phenyl-3-(phosphonatooxy)-4-{[(1,3-thiazol-5-ylmethoxy)carbonyl]amino}pentyl)-$N^2$-{[[(2-isopropyl-1,3-thiazol-4-yl)methyl](methyl)amino]carbonyl}-L-valinamide To a solution of the product from Example 8A (6.2 g, 6.32 mmol) in dichloromethane (200 mL) at 0° C. was added trimethylsilyl bromide (3.87 g) via syringe, and the mixture was stirred at 0° C. for 1 hour. The solvent was evaporated and the residue was triturated with water (50 mL), followed by evaporation under reduced pressure. The residue was purified by chromatography (C18), eluting with 20% acetonitrile in water (0.1% trifluoroacetic acid) and then with 40% acetonitrile in water (0.1% trifluoroacetic acid), to give 1.21 g of the pure acid. The disodium salt was formed by treating 1.21 g of the purified acid in acetonitrile (75 mL) with a solution of $NaHCO_3$ (0.254 g) in water (50 mL). After stirring for 15 minutes the solvent was evaporated to give the title compound. $^1$H NMR (300 MHz, DMSO-d$_6$), δ ppm 0.66 (d, J=6.1 Hz, 3H), 0.75 (d, J=6.1 Hz, 3H), 1.26 (d, J=6.8 Hz, 6H), 1.45-1.61 (m, 2H), 1.80-1.93 (m, 1H), 2.59-2.65 (m, 1H), 2.86 (s, 3H), 3.14-3.23 (m, 2H), 3.82 (t, J=9.0 Hz, 1H), 3.94-4.07 (m, 2H), 4.35-4.52 (m, 2H), 5.07 (d, J=12.9 Hz, 2H), 5.23 (d, J=12.9 Hz, 1H), 6.99-7.19 (m, 10H), 7.25 (s, 1H), 7.83 (s, 1H), 9.03 (s, 1H).

Example 9

Disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate

Example 9A 2,2-dimethylbutane-1,4-diol

To a solution of 2,2-dimethylsuccinic acid (2.0 g, 13.7 mmol) in THF (30 mL) at 0° C. was added dropwise a solution of lithium aluminum hydride in THF (41 mL, 1 M). After the addition was complete the mixture was refluxed for 1 hour. After cooling to room temperature, water (2 mL) was added, followed by 3 M NaOH (3 mL), and then water (4 mL). The solids were filtered and washed with ether. The filtrate was partitioned and the organic phase was dried with $MgSO_4$, filtered and evaporated. The residue was dissolved in chloroform, dried with $MgSO_4$, filtered and evaporated to give the title compound (1.58 g).

Example 9B dibenzyl 4-hydroxy-2,2-dimethylbutyl phosphate

To a solution of the product from Example 9A (0.80 g, 6.8 mmol) and 1H-tetrazole (0.190 g) in THF (7.0 mL) at 0° C. was added dibenzyl diethylphosphoramidite (0.96 mL), and the solution was allowed to warm to room temperature and was stirred for 68 hours. To this solution was added dichloromethane (7.0 mL) and the mixture was cooled to −45° C., followed by addition of m-chloroperbenzoic acid (1.3 g). The mixture was stirred at −45° C. for 1 hour and at room temperature for 1 hour. 10% $Na_2CO_3$ was added and the reaction was extracted twice with chloroform. The combined organic layer was dried over $MgSO_4$, filtered and evaporated. The residue was purified by chromatography on silica gel, eluting with a gradient of 50-100% ethyl acetate in chloroform, to give the title compound (0.396 g, 17%).

Example 9C

4-{[bis(benzyloxy)phosphoryl]oxy}-3,3-dimethylbutanoic acid

To a solution of the product from Example 9B (0.396 g, 1.0 mmol) in DMF (10 mL) at room temperature was added pyridinium dichromate (2.3 g), and the mixture was stirred for 48 hours. 10% citric acid was added and the reaction was extracted twice with ethyl acetate. The combined organic layer was washed with brine, dried over $MgSO_4$, filtered and evaporated. The residue was purified by chromatography on silica gel, eluting with a gradient of 0-5% methanol in chloroform, to give the title compound (0.334 g, 81%).

Example 9D

(1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl 4-{[bis(benzyloxy)phosphoryl]oxy}-3,3-dimethylbutanoate To a solution containing the compound of Example 3 (0.075 g, 0.12 mmol), the product from Example 9C (0.056 g), and DMAP (0.017 g) in DMF (1.2 mL) was added EDAC (0.027 g) and the mixture was stirred at room temperature for 16 hours. Additional product from Example 9C (0.056 g) and EDAC (0.027 g) were added and the reaction was stirred at room temperature for 3 hours. The solvent was evaporated and the reaction mixture was partitioned between ethyl acetate and aqueous $NaHCO_3$. The organic layer was washed with brine, dried over $MgSO_4$, filtered and evaporated. The residue was purified by chromatography on silica gel, eluting with a gradient starting with 33% ethyl acetate in chloroform and ending with 5% methanol in chloroform, to give the title compound (0.101 g, 84%).

Example 9E

Disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-2,2-dimethylpropyl phosphate To a solution of the product from Example 9D (0.095 g, 0.095 mmol) in a mixture of ethyl acetate (0.7 mL) and methanol (0.7 mL) was added $Pd(OH)_2$ on carbon (0.050 g, 20% by wt. Pd), and the mixture was stirred under an atmosphere of hydrogen (balloon pressure) for 68 hours. The reaction was filtered through celite and the solvent was evaporated. Methanol and water were added and the pH was adjusted to 9 by addition of 10% $Na_2CO_3$ solution, purified by HPLC using a C18 column, eluting with a gradient of 0-100% of methanol in water, to give the title compound (0.063 g, 77% yield). $^1$H NMR (300 MHz, MeOH-d$_4$), δ ppm 0.83 (d, J=6.6 Hz, 3H), 0.88 (d, J=6.6 Hz, 3H), 1.09 (s, 3H), 1.10 (s, 3H), 1.27-1.32 (m, 1H), 1.44-1.55 (m, 1H), 1.62-1.88 (m, 3H), 2.16 (s, 6H), 2.46-2.56 (m, 2H), 2.59 (dd, J=9.9, 13.6 Hz, 1H), 2.73-2.85 (m, 4H), 2.98-3.09 (m, 1H), 3.11-3.16 (m, 2H), 3.57 (d, J=4.0 Hz, 2H), 4.09-4.19 (m, 2H), 4.26 (d, J=11.0 Hz, 1H), 4.43-4.52 (m, 1H), 4.93-4.98 (m, 1H), 5.03-5.08 (m, 1H), 6.88-7.00 (m, 3H), 7.10-7.32 (m, 10H).

Example 10 disodium N$^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide

Example 10A

4-{[tert-butyl(dimethyl)silyl]oxy}2,2-dimethylbutan-1-ol

To a solution of the product from Example 9A (0.80 g, 6.8 mmol) and imidazole (0.462 g) in THF (8.0 mL) at room temperature was added tert-butyldimethylsilyl chloride (1.02 g), and the solution was stirred for 16 hours. The reaction mixture was partitioned between ethyl acetate and water, and the organic was washed with brine, dried over $MgSO_4$, filtered and evaporated. The residue was purified by chromatography on silica gel, eluting with a gradient starting with 33% hexanes in chloroform and ending with 25% ethyl acetate in chloroform, to give the title compound (1.153 g, 73%).

Example 10B di-tert-butyl 4-{[tert-butyl(dimethyl)silyl]oxy}-2,2-dimethylbutyl phosphate To a solution of the product from Example 10A (0.630 g, 2.7 mmol) and 1H-tetrazole (0.568 g) in dichloromethane (11.0 mL) at room temperature was added di-t-butyl diethylphosphoramidite (1.02 g), and the solution was allowed to stir for 1 hour. The solution was cooled to −45° C., followed by addition of m-chloroperbenzoic acid (1.33 g). After 1 hour at −45° C., additional m-chloroperbenzoic acid (1.33 g) was added and the mixture was allowed to warm to room temperature and was stirred for 16 hours. The reaction mixture was diluted with chloroform and washed with 10% $Na_2CO_3$ and brine, and was dried over $MgSO_4$, filtered and evaporated. The residue was purified by chromatography on silica gel, eluting with 20% ethyl acetate in hexane, to give the title compound (0.441 g, 38%).

Example 10C di-tert-butyl 4-hydroxy-2,2-dimethylbutyl phosphate

To a solution of the product from Example 10B (0.435 g, 1.03 mmol) in THF (3.8 mL) was added a solution of tetrabutylammonium fluoride in THF (1 M, 1.2 mL), and the reaction was stirred at room temperature for 1 hour. The reaction mixture was diluted with ethyl acetate and washed with water and brine, dried over MgSO$_4$, filtered and evaporated. The residue was purified by chromatography on silica gel, eluting with 33% ethyl acetate in hexane, to give the title compound (0.239 g, 75%).

Example 10D

4-[(di-tert-butoxyphosphoryl)oxy]-3,3-dimethylbutanoic acid

To a solution of the product from Example 10C (0.235 g, 0.76 mmol) in DMF (7.6 mL) at room temperature was added pyridinium dichromate (1.71 g), and the mixture was stirred for 16 hours. 10% citric acid was added and the reaction mixture was extracted twice with ethyl acetate. The combined organic layer was washed with brine, dried over MgSO$_4$, filtered and evaporated. The residue was purified by chromatography on silica gel, eluting with a gradient starting with chloroform and ending with 5% methanol in chloroform, to give the title compound (0.144 g, 60%).

Example 10E (1S,3S)-3-[(N-{[[(2-isopropyl-1,3-thiazol-4-yl)methyl](methyl)amino]carbonyl}-L-valyl)amino]-4-phenyl-1-((1S)-2-phenyl-1-{[(1,3-thiazol-5-ylmethoxy)carbonyl]amino}ethyl)butyl 4-[(di-tert-butoxyphosphoryl)oxy]-3,3-dimethylbutanoate To a solution containing the compound of Example 1 (0.10 g, 0.14 mmol), the product from Example 10D (0.045 g), and 4-(dimethylamino)pyridine (0.017 g) in DMF (1.4 mL) was added EDAC (0.027 g), and the mixture was stirred at room temperature for 68 hours. Additional product from Example 10D (0.045 g) and EDAC (0.027 g) were added and the reaction mixture was stirred at room temperature for 18 hours. The solvent was evaporated and the concentrate was partitioned between ethyl acetate and aqueous NaHCO$_3$. The organic layer was washed with brine, dried over MgSO$_4$, filtered and evaporated. The residue was purified by chromatography on silica gel, eluting with a gradient starting with ethyl acetate and ending with 5% methanol in ethyl acetate, to give the title compound (0.115 g, 81% yield).

Example 10F disodium N$^1$-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide A solution of the product from Example 10E (0.112 g, 0.11 mmol) in a mixture of dichloromethane (1.0 mL) and trifluoroacetic acid (1.0 mL) was stirred at room temperature for 20 minutes. The solvent was evaporated, and methanol and water were added. The pH was adjusted to 10 by addition of 10% Na$_2$CO$_3$ solution, followed by purification by chromatography using a C18 column, eluting with a gradient starting with water and ending with methanol, to give the title compound (0.068 g, 64% yield). $^1$H NMR (300 MHz, MeOH-d$_4$) δ ppm 0.82 (d, J=6.6 Hz, 3H), 0.85 (d, J=6.6 Hz, 3H), 1.06 (s, 3H), 1.07 (s, 3H), 1.36 (d, J=7.0 Hz, 6H), 1.57-1.80 (m, 2H), 1.89-2.01 (m, 1H), 2.41-2.53 (m, 2H), 2.59-2.74 (m, 4H), 2.96 (s, 3H), 3.57 (d, J=4.0 Hz, 2H), 3.98 (d, J=7.7 Hz, 1H), 4.32-4.43 (m, 2H), 4.50 (q, J=16.2 Hz, 2H), 4.85-5.01 (m, 2H), 5.17 (s, 2H), 7.01-7.21 (m, 11H), 7.79 (s, 1H), 8.93 (s, 1H).

Example 11

Disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate

Example 11A dibenzyl 4-hydroxy-3,3-dimethylbutyl phosphate

To a solution of the product from Example 9A (0.80 g, 6.8 mmol) and 1H-tetrazole (0.190 g) in THF (7.0 mL) at 0° C. was added dibenzyl diethylphosphoramidite (0.96 mL), and the solution was allowed to warm to room temperature and was stirred for 68 hours. To this solution was added dichloromethane (7.0 mL) and the mixture was cooled to −45° C., followed by addition of m-chloroperbenzoic acid (1.3 g). The mixture was stirred at −45° C. for 1 hour and at room temperature for 1 hour. 10% Na$_2$CO$_3$ was added and the reaction was extracted twice with chloroform. The combined organic layer was dried over MgSO$_4$, filtered and evaporated. The residue was purified by chromatography on silica gel, eluting with a gradient starting with 50% ethyl acetate in chloroform and ending with ethyl acetate, to give the title compound (0.922 g, 45%).

Example 11B

4-{[bis(benzyloxy)phosphoryl]oxy}-2,2-dimethylbutanoic acid

To a solution of the product from Example 11A (0.922 g, 2.4 mmol) in DMF (20 mL) at room temperature was added pyridinium dichromate (5.5 g), and the mixture was stirred for 16 hours. 10% citric acid was added and the reaction was extracted twice with ethyl acetate. The combined organic layer was washed with brine, dried over MgSO$_4$, filtered and evaporated. The residue was purified by chromatography on silica gel, eluting with a gradient starting with chloroform and ending with 5% methanol in chloroform, to give the title compound (0.839 g, 88%).

Example 11C dibenzyl 4-chloro-3,3-dimethyl-4-oxobutyl phosphate

To a solution of the product from Example 11B (0.211 g, 0.538 mmol) in dichloromethane (1.35 mL) at 0° C. were added DMF (4 µL) and a solution of oxalyl chloride in dichloromethane (2M, 0.538 mL) and the mixture was stirred for 45 minutes at 0° C. The solvent was evaporated under reduced pressure and the residue was used without further purification.

Example 11D (1S,3S)-1-((1S)-1-{[(2,6-dimethylphenoxy)acetyl]
amino}-2-phenylethyl)-3-{[(2S)-3-methyl-2-(2-ox-
otetrahydropyrimidin-1(2H)-yl)butanoyl]amino}-4-
phenylbutyl 4-{[bis(benzyloxy)phosphoryl]oxy}-2,
2-dimethylbutanoate To a solution containing the product from Example 11C (0.538 mmol) dissolved in dichloromethane (1.0 mL) at 0° C., were added the product of Example 3 (0.085 g, 0.134 mmol) and 4-(dimethylamino)pyridine (0.066 g) and the reaction was allowed to warm to room temperature and was stirred for 16 hours. The reaction was diluted with dichloromethane, and the organic layer was washed with 10% citric acid, water and brine, dried over MgSO$_4$, filtered and evaporated. The residue was purified by chromatography on silica gel, eluting with a gradient starting with dichloromethane and ending with 5% methanol in ethyl acetate, to give the title compound (0.075 g, 56%).

Example 11E

Disodium 3-[((1S,3S)-1-((1S)-1-{[(2,6-dimethylphe-
noxy)acetyl]amino}-2-phenylethyl)-3-{[(2S)-3-me-
thyl-2-(2-oxotetrahydropyrimidin-1(2H)-yl)bu-
tanoyl]amino}-4-phenylbutyl)oxycarbonyl]-3,3-
dimethylpropyl phosphate To a solution of the product from Example 11D (0.066 g, 0.066 mmol) in a mixture of ethyl acetate (0.5 mL) and methanol (0.5 mL) was added Pd(OH)$_2$ on Carbon (0.066 g, 20% by wt. Pd), and the mixture was stirred under an atmosphere of hydrogen (balloon pressure) for 2.5 hours. The reaction was filtered through celite and the solvent was evaporated. Methanol and water were added and the pH was adjusted to 9 by addition of 10% Na$_2$CO$_3$ solution, followed by purification by chromatography using a C18 column, eluting with a gradient starting with water and ending with methanol, to give the title compound (0.039 g, 68% yield). $^1$H NMR (300 MHz, MeOH-d$_4$), δ ppm 0.82 (d, J=6.6 Hz, 3H), 0.87 (d, J=6.6 Hz, 3H), 1.30 (s, 6H), 1.43-1.54 (m, 1H), 1.67-1.87 (m, 3H), 1.89-2.13 (m, 3H), 2.18 (s, 6H), 2.59 (dd, J=10.3, 13.6 Hz, 1H), 2.71-2.89 (m, 4H), 3.01-3.06 (m, 1H), 3.08-3.17 (m, 2H), 3.88-3.95 (m, 2H), 4.15 (s, 2H), 4.25 (d, J=11.0 Hz, 1H), 4.42-4.50 (m, 1H), 4.90-4.95 (m, 1H), 5.06-5.10 (m, 1H), 6.89-6.94 (m, 1H), 6.98-7.01 (m, 2H), 7.10-7.31 (m, 10H).

Example 12 disodium N$^1$-((1S,3S,4S)-1-benzyl-5-phenyl-3-[1-
(phosphonatooxy)butoxy]-4-{[(1,3-thiazol-5-yl-
methoxy)carbonyl]amino}pentyl)-N$^2$-{[[(2-isopro-
pyl-1,3-thiazol-4-yl)methyl](methyl)amino]
carbonyl}-L-valinamide

Example 12A

N$^1$-((1S,3S,4S)-1-benzyl-3-[1-(butylthio)butoxy]-5-
phenyl-4-{[(1,3-thiazol-5-ylmethoxy)carbonyl]
amino}pentyl)-N$^2$-{[[(2-isopropyl-1,3-thiazol-4-yl)
methyl](methyl)amino]carbonyl}-L-valinamide To a solution of the compound of Example 1 (3.0 g, 4.2 mmol) and butyl sulfide (18 mL) in acetonitrile (24 mL) at 0° C. was added benzoyl peroxide (2.0 g) in three portions over 3 hours, and the reaction was stirred at 0° C. for 1 hour and then at room temperature for 1 hour. Additional benzoyl peroxide (4.0 g) was added in two portions over 2 hours at room temperature. The reaction was diluted with ethyl acetate and washed with 10% Na$_2$CO$_3$ and brine. The organic phase was dried over MgSO$_4$, filtered and evaporated. The concentrate was chromatographed on silica gel eluting with a gradient starting with 50% ethyl acetate in chloroform and ending with ethyl acetate to give the title compound (2.43 g, 68% yield).

Example 12B disodium N$^1$-((1S,3S,4S)-1-benzyl-5-phenyl-3-[1-
(phosphonatooxy)butoxy]-4-{[(1,3-thiazol-5-yl-
methoxy)carbonyl]amino}pentyl)-N$^2$-{[[(2-isopro-
pyl-1,3-thiazol-4-yl)methyl](methyl)amino]
carbonyl}-L-valinamide To a solution containing the product from Example 12A (1.2 g, 1.4 mmol), molecular sieves (4 Å, 6.0 g), and phosphoric acid (0.85 g) in DMF (28 mL) at 0° C. was added N-iodosuccinimide (0.406 g), and the mixture was stirred at 0° C. for 1 hour. To the cold reaction was added 10% Na$_2$CO$_3$ to adjust the pH to 9, and the mixture was diluted with methanol and filtered. The filtrate was treated with 1 M Na$_2$S$_2$O$_3$ until it was clear, diluted with methanol and filtered again. The solvent was evaporated, and the crude product was purified by HPLC on a C18 column, eluting with a gradient starting with water and ending with methanol to give the title compound (0.605 g, 47% yield).

$^1$H NMR (300 MHz, MeOH-d$_4$) δ ppm 0.88-0.98 (m, 9H), 1.33-1.36 (m, 6H), 1.44-2.24 (m, 7H), 2.56-2.85 (m, 4H), 2.88-2.98 (m, 1H), 3.01 (s, 3H), 3.90-4.03 (m, 1H), 4.03-4.16 (m, 2H), 4.18-4.26 (m, 0.5H), 4.29-4.39 (m, 0.5H), 4.46-4.65 (m, 2H), 4.93-5.02 (m, 1H), 5.08-5.14 (m, 1H), 5.22-5.30 (m, 1H), 6.97-7.25 (m, 11H), 7.65-7.74 (m, 1H), 8.91-8.92 (m, 1H).

Example 13

Disodium N$^1$-((1S,3S,4S)-1-benzyl-3-[2-methyl-1-
(phosphonatooxy)propoxy]-5-phenyl-4-{[(1,3-thia-
zol-5-ylmethoxy)carbonyl]amino}pentyl)-N$^2$-{[[(2-
isopropyl-1,3-thiazol-4-yl)methyl](methyl)amino]
carbonyl}-L-valinamide

Example 13A

N$^1$-((1S,3S,4S)-1-benzyl-3-[1-(isobutylthio)-2-meth-
ylpropoxy]-5-phenyl-4-{[(1,3-thiazol-5-ylmethoxy)
carbonyl]amino}pentyl)-N$^2$-{[[(2-isopropyl-1,3-
thiazol-4-yl)methyl](methyl)amino]carbonyl}-L-
valinamide To a solution of the compound of Example 1 (1.0 g, 1.38 mmol) and diisobutyl sulfide (6.2 mL) in acetonitrile (10 mL) at 0° C. was added benzoyl peroxide (2.0 g) in three portions over 30 minutes, and the reaction was stirred at 0° C. for 1 hour. The reaction was diluted with ethyl acetate and washed with 10% Na$_2$CO$_3$ and brine. The organic phase was dried over MgSO$_4$, filtered and evaporated. The residue was chromatographed on silica gel eluting with a gradient starting with 0-100% ethyl acetate/dichloromethane to provide the title product (0.890 g, 75% yield).

Example 13B

Disodium N¹-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide To a solution containing the product from Example 13A (0.888 g, 1.03 mmol), molecular sieves (4 Å, 3.5 g), and phosphoric acid (0.50 g) in DMF (20 mL) at 0° C. was added N-iodosuccinimide (0.46 g), and the mixture was stirred at 0° C. for 1 hour. To the cold reaction mixture was added 10% $Na_2CO_3$ to adjust the pH to 9, and the mixture was diluted with methanol, treated with 1 M $Na_2S_2O_3$ until it was clear, and filtered to remove the solids. The solvent was evaporated, and the crude product was purified by HPLC using C18 column, eluting with a gradient starting with water and ending with methanol to give the product (0.49 g, 52% yield). ¹H NMR (300 MHz, MeOH-$d_4$), δ ppm 0.86-1.03 (m, 12H), 1.33-1.36 (m, 6H), 1.44-1.75 (m, 1H), 1.85-2.27 (m, 3H), 2.54-2.9 (m, 5H), 3.01 (s, 3H), 3.78-4.38 (m, 4H), 4.46-4.68 (m, 2H), 4.91-5.15 (m, 3H), 6.97-7.26 (m, 11H), 7.64-7.73 (m, 1H), 8.91-8.92 (m, 1H).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound having formula (I), (II), or (III)

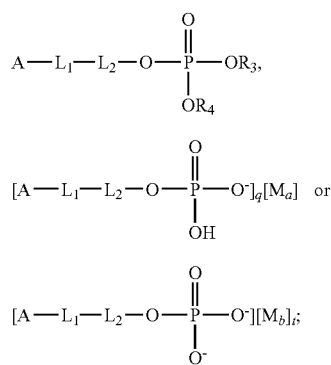

wherein:
- $L_1$ is selected from the group consisting of a bond, —C(O)—, and —C(O)O—, wherein the carbonyl of the —C(O)O— moiety is attached to A of formula (I), (II), or (III);
- $L_2$ is —$(CR_1R_2)_m$—,
- m is 1, 2, 3, 4, or 5;
- $R_1$ at each occurrence is independently selected from the group consisting of hydrogen and $C_1$-$C_{12}$ alkyl;
- $R_2$ at each occurrence is independently selected from the group consisting of hydrogen and $C_1$-$C_{12}$ alkyl;
- $R_3$ is selected from the group consisting of hydrogen, $C_1$-$C_{12}$ alkyl, and arylalkyl;
- $R_4$ is selected from the group consisting of hydrogen, $C_1$-$C_{12}$ alkyl, and arylalkyl;
- q is 1 or 2;
- t is 1 or 2;
- $M_a$ is selected from the group consisting of $M_1$ and $M_2$;
- $M_b$ is selected from the group consisting of $M_1$ and $M_2$;
- $M_1$ is selected from the group consisting of $Na^+$, $K^+$, and $^+N(R_5)(R_6)(R_7)(R_8)$;
- $M_2$ is selected from the group consisting of $Ca^{2+}$, $Ba^{2+}$, $Mg^{2+}$, $Zn^{2+}$, and $^+N(R_9)(R_{10})(R_{11})(R_{12})$, as to $R_5$ and $R_6$:
  - $R_5$ is selected from the group consisting of hydrogen, alkyl, hydroxyalkyl, arylalkyl, and —C(=NH)NH₂, and
  - $R_6$ is selected from the group consisting of hydrogen, alkyl, hydroxyalkyl, and arylalkyl, or, alternatively,
  - $R_5$ and $R_6$, together with the nitrogen atom to which they are attached, form a piperidine ring;
- $R_7$ is selected from the group consisting of hydrogen and alkyl;
- $R_8$ is selected from the group consisting of hydrogen and alkyl;
- as to $R_9$ and $R_{11}$:
  - $R_9$ is -alkyl-$N^+(Z_1)(Z_2)(Z_3)$, and
  - $R_{11}$ is selected from the group consisting of hydrogen and alkyl, or, alternatively,
  - $R_{19}$ and $R_{11}$, together with the nitrogen atom to which they are attached, form a piperazine ring;
- $R_{10}$ is hydrogen, alkyl or arylalkyl;
- $R_{12}$ is hydrogen or alkyl;
- $Z_1$ is selected from the group consisting of hydrogen and alkyl;
- $Z_2$ is selected from the group consisting of hydrogen and alkyl;
- $Z_3$ is selected from the group consisting of hydrogen, alkyl, and arylalkyl; and
- A is selected from the group consisting of

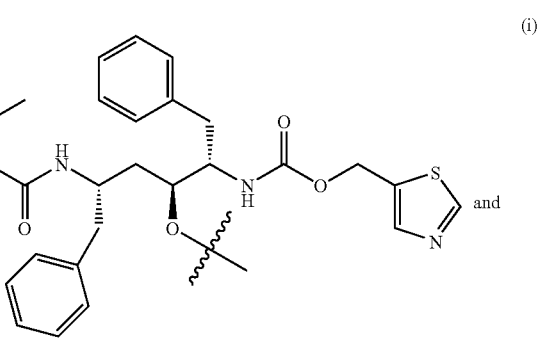

and

-continued

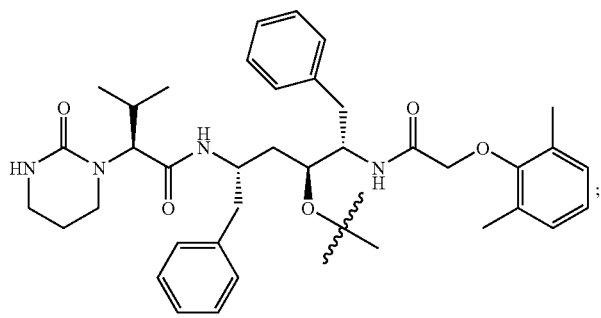
(ii)

provided that:
when q is 1, $M_a$ is $M_1$;
when q is 2, $M_a$ is $M_2$;
when t is 1, $M_b$ is $M_2$;
when t is 2, $M_b$ is $M_1$; and
provided that:
when A is $R_2$ is $C_1$-$C_{12}$ alkyl,
q is 1,
$M_a$ is selected from the group consisting of Na⁺, K⁺, and NH$_4$⁺,
t is 2, and
$M_b$ is selected from the group consisting of Na⁺, K⁺, and NH$_4$⁺.

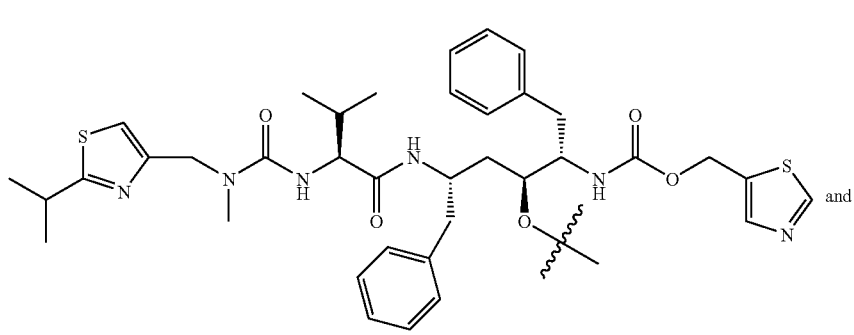
(i)

and $L_1$ is a bond, then $L_2$ is not —CH$_2$—.

2. The compound of claim 1, wherein:
$L_1$ is a bond,
m is 1,
$R_1$ is hydrogen, and
$R_2$ is hydrogen.

3. The compound of claim 1, wherein:
$L_1$ is a bond,
m is 1,
$R_1$ is hydrogen, and
$R_2$ is $C_1$-$C_{12}$ alkyl.

4. The compound of claim 1, wherein:
$L_1$ is a bond,
m is 1,
$R_1$ is hydrogen,
$R_2$ is hydrogen,
q is 1,
$M_a$ is selected from the group consisting of Na⁺, K⁺, and NH$_4$⁺,
t is 2, and
$M_b$ is selected from the group consisting of Na⁺, K⁺, and NH$_4$⁺.

5. The compound of claim 1, wherein:
$L_1$ is a bond,
m is 1,
$R_1$ is hydrogen, 6. The compound of claim 1, wherein $L_1$ is —C(O)—.

7. The compound of claim 1, wherein:
$L_1$ is —C(O)—,
$L_2$ is —(CR$_1$R$_2$)$_m$—, and
m is 3.

8. The compound of claim 1, wherein:
$L_1$ is —C(O)—,
$L_2$ is —(CR$_1$R$_2$)$_m$—,
m is 3,
q is 1,
$M_a$ is selected from the group consisting of Na⁺, K⁺, and NH$_4$⁺,
t is 2, and
$M_b$ is selected from the group consisting of Na⁺, K⁺, and NH$_4$⁺.

9. The compound of claim 1, wherein the compound is selected from the group consisting of
calcium N$^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide;
calcium [((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate; and calcium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate.

10. Disodium N¹-((1S,3S,4S)-1-benzyl-5-phenyl-3-[(phosphonatooxy)methoxy]-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide.

11. Calcium N¹-((1S,3S,4S)-1-benzyl-5-phenyl-3-[(phosphonatooxy)methoxy]4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide.

12. The compound of claim 1, wherein A is

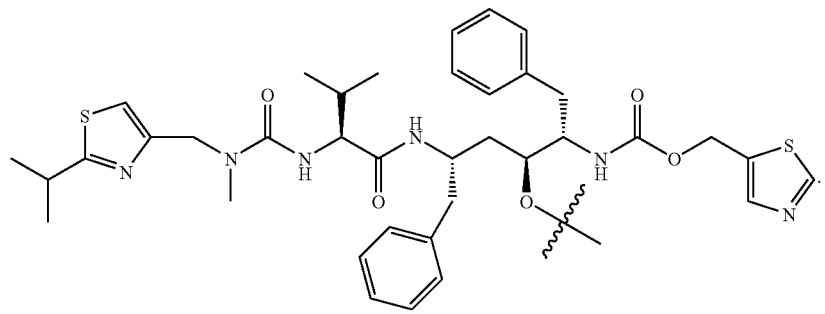

(i)

13. The compound of claim 12, wherein L₁ is a bond.
14. The compound of claim 12, wherein:
L₁ is a bond,
L₂ is —(CR₁R₂)$_m$—,
m is 1,
R₁ is hydrogen, and
R₂ is C₁-C₁₂ alkyl.
15. The compound of claim 12, wherein:
L₁ is a bond,
L₂ is —(CR₁R₂)$_m$—,
m is 1,
R₁ is hydrogen,
R₂ is C₁-C₁₂ alkyl,
q is 1,
M$_a$ is selected from the group consisting of Na⁺, K⁺, and NH₄⁺,
t is 2, and
M$_b$ is selected from the group consisting of Na⁺, K⁺, and NH₄⁺.
16. The compound of claim 12, wherein:
L₁ is —C(O)—,
L₂ is —(CR₁R₂)$_m$—, and
m is 3.
17. The compound of claim 12, wherein:
L₁ is —C(O)—,
L₂ is —(CR₁R₂)$_m$—,
m is 3,
q is 1,
M$_a$ is selected from the group consisting of Na⁺, K⁺, and NH₄⁺,
t is 2 and
M$_b$ is selected from the group consisting of Na⁺, K⁺, and NH₄⁺.
18. The compound of claim 12, wherein the compound is selected from the group consisting of disodium N¹-((1S,3S,4S)-1-benzyl-5-phenyl-3-[1-(phosphonatooxy)ethoxy]-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide;

disodium N¹-((1S,3S,4S)-1-benzyl-3-{[3,3-dimethyl-4-(phosphonatooxy)butanoyl]oxy}-5-phenyl-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide;

disodium N¹-((1S,3S,4S)-1-benzyl-5-phenyl-3-[1-(phosphonatooxy)butoxy]-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide; and disodium N¹-((1S,3S,4S)-1-benzyl-3-[2-methyl-1-(phosphonatooxy)propoxy]-5-phenyl-4-{[(1,3-thiazol-5-ylmethoxy)carbonyl]amino}pentyl)-N²-{[[(2-isopropyl-1,3-thiazol-4-yl)methyl](methyl)amino]carbonyl}-L-valinamide.

19. The compound of claim 1, wherein A is

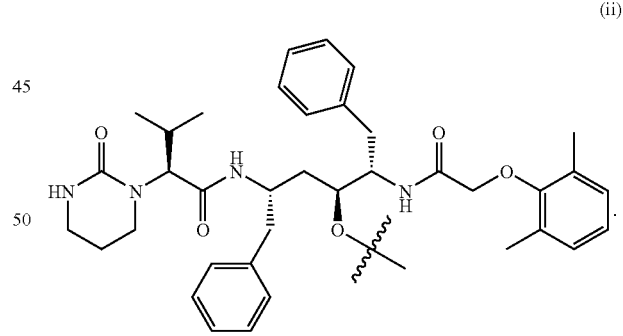

(ii)

20. The compound of claim 19, wherein L₁ is a bond.
21. The compound of claim 19, wherein:
L₁ is a bond,
L₂ is —(CR₁R₂)$_m$—,
m is 1,
R₁ is hydrogen, and
R₂ is hydrogen.
22. The compound of claim 19, wherein:
L₁ is a bond,
L₂ is —(CR₁R₂)$_m$—,
m is 1, $R_1$ is hydrogen, and
$R_2$ is $C_1$-$C_{12}$alkyl.

23. The compound of claim 19, wherein:
$L_1$ is a bond,
$L_2$ is —$(CR_1R_2)_m$—,
m is 1,
$R_1$ is hydrogen,
$R_2$ is $C_1$-$C_{12}$ alkyl,
q is 1,
$M_a$ is selected from the group consisting of Na$^+$, K$^+$, and NH$_4^+$,
t is 2, and
$M_b$ is selected from the group consisting of Na$^+$, K$^+$, and NH$_4^+$.

24. The compound of claim 19, wherein:
$L_1$ is a bond,
$L_2$ is —$(CR_1R_2)_m$—,
m is 1,
$R_1$ is hydrogen,
$R_2$ is hydrogen,
q is 1,
$M_a$ is selected from the group consisting of Na$^+$, K$^+$, and NH$_4^+$,
t is 2, and
$M_b$ is selected from the group consisting of Na$^+$, K$^+$, and NH$_4^+$.

25. The compound of claim 19, wherein:
$L_1$ is —C(O)—,
$L_2$ is —$(CR_1R_2)_m$—, and
m is 3.

26. The compound of claim 19, wherein:
$L_1$ is —C(O)—,
$L_2$ is —$(CR_1R_2)_m$—,
m is 3,
q is 1,
$M_a$ is selected from the group consisting of Na$^+$, K$^+$, and NH$_4^+$,
t is 2, and
$M_b$ is selected from the group consisting of Na$^+$, K$^+$, and NH$_4^+$.

27. The compound of claim 19, wherein the compound is selected from the group consisting of
disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate;
disodium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate;
disodium 3-[((1S,3S)-1-((1S)-1-{[(2,6-dimethylphenoxy)acetyl]amino}-2-phenylethyl)-3-{[(2.5)-3-methyl-2-(2-oxotetrahydropyrimidin-1(2H)-yl)butanoyl]amino}-4-phenylbutyl)oxycarbonyl]-2,2-dimethylpropyl phosphate; and
disodium 3-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxycarbonyl]-3,3-dimethylpropyl phosphate.

28. A pharmaceutical composition comprising:
a therapeutically effective amount of a compound or combination of compounds of claim 1, and
a pharmaceutically acceptable carrier.

29. The pharmaceutical composition of claim 28, wherein the compound of claim us disodium N$^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide.

30. A pharmaceutical composition comprising:
a therapeutically effective amount of disodium N$^1$-((1S,3S,4S)-1-benzyl-5-phenyl-3-[(phosphonatooxy)methoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide, and
a pharmaceutically acceptable carrier.

31. The pharmaceutical composition of claim 28, wherein the compound of claim 1 is disodium 1-[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]ethyl phosphate.

32. The pharmaceutical composition of claim 28, wherein the compound of claim 1 is disodium[((1S,3S)-1-((1S)-1-{[(2,6-dimethylphenoxy)acetyl]amino}-2-phenylethyl)-3-{[(2S)-3-methyl-2-(2-oxotetrahydropyrimidin-1(2H)-yl)butanoyl]amino}-4-phenylbutyl)oxy]methyl phosphate.

33. A pharmaceutical composition comprising:
a therapeutically effective amount of a compound or combination of compounds of claim 1, and one, two, three, four, five or six agents independently selected from the group consisting of a second HIV protease inhibitor, a HIV reverse transcriptase inhibitor, an HIV entry/fusion inhibitor, an HIV integrase inhibitor, and an HIV budding/maturation inhibitor, and
a pharmaceutically acceptable carrier.

34. The pharmaceutical composition of claim 33, wherein the second HIV protease inhibitor is selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684, and GW640385X.

35. The pharmaceutical composition of claim 33, wherein the HIV reverse transcriptase inhibitor is selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125.

36. The pharmaceutical composition of claim 33, wherein the HIV entry/fusion inhibitor is selected from the group consisting of enfuvirtide (T-20), T-1249, PRO2000, PRO542, PRO140, AMD-3100, BMS-806, FP21399, GW873140, Schering C (SCH-C), Schering D (SCH-D), TNX-355, and UK-427857.

37. The pharmaceutical composition of claim 33, wherein the HIV integrase inhibitor is selected from the group consisting of 5-1360, zintevir (AR-177), L-870812, and L-870810.

38. The pharmaceutical composition of claim 33, wherein the HIV budding/maturation inhibitor is PA-457.

39. The pharmaceutical composition of claim 33, wherein the compound of claim 1 is disodium N$^1$-((1S,3S,4S)-1-benzyl-5-phenyl-3-[1-(phosphonatooxy)ethoxy]-4-{[(1,3-thiazol-5-ylmethoxy)carbonyl]amino}pentyl)-N$^2$-{[[(2-isopropyl-1,3-thiazol-4-yl)methyl](methyl)amino]carbonyl}-L-valinamide.

40. A pharmaceutical composition comprising:
a therapeutically effective amount of disodium N$^1$-((1S,3S,4S)-1-benzyl-5-phenyl-3-[(phosphonatooxy)methoxy]-4-{[(1,3-thiazol-5-ylmethoxy)carbonyl]

amino}pentyl)-N²-{[[(2-isopropyl-1,3-thiazol-4-yl)methyl](methyl)amino]carbonyl}-L-valinamide, and one, two, three, four, five or six agents independently selected from the group consisting of a second HIV protease inhibitor, a HIV reverse transcriptase inhibitor, an HIV entry/fusion inhibitor, an HIV integrase inhibitor, and an HIV budding/maturation inhibitor, and a pharmaceutically acceptable carrier.

41. The pharmaceutical composition of claim 33, wherein the compound of claim 1 is disodium 1-[((1S,3S)-1-((15)-1-{[(2,6-dimethylphenoxy)acetyl]amino}-2-phenylethyl)-3-{[(2S)-3-methyl-2-(2-oxo tetrahydropyrimidin-1(2H)-yl)butanoyl]amino}-4-phenylbutyl)oxy]ethyl phosphate.

42. The pharmaceutical composition of claim 33, wherein the compound of claim 1 is disodium[((1S,3S)-1-((1S)-1-{[(2,6-dimethylphenoxy)acetyl]amino}-2-phenylethyl)-3-{[(2S)-3-methyl-2-(2-oxo tetrahydropyrimidin-1(2H)-yl)butanoyl]amino}-4-phenylbutyl)oxy]methyl phosphate.

* * * * *

UNITED STATES PATENT AND TRADEMARK OFFICE
CERTIFICATE OF CORRECTION

| | | |
|---|---|---|
| PATENT NO. | : 7,718,633 B2 | Page 1 of 1 |
| APPLICATION NO. | : 11/170197 | |
| DATED | : May 18, 2010 | |
| INVENTOR(S) | : David A. DeGoey et al. | |

It is certified that error appears in the above-identified patent and that said Letters Patent is hereby corrected as shown below:

Column 86, line 40, claim 1: "$R_{19}$ and $R_{11}$, together with the nitrogen atom to which" to read as
-- $R_9$ and $R_{11}$, together with the nitrogen atom to which --

Column 87, line 20, claim 1: "when q is 2, $M_3$ is $M_2$;" to read as -- when q is 2, $M_a$ is $M_2$; --

Column 89, line 1, claim 9: "calcium 1-[((1S,3S)-1-((1S)-1-{[(2,6-dimethylphenoxy)" to read as
-- calcium 1-[((1S,3S)-1-((1S)-1-{[(2,6-dimethylphenoxy) --

Column 89, line 60, claim 17: "$M_3$ is selected from the group consisting of $Na^+$, $K^+$, and" to read as
-- $M_a$ is selected from the group consisting of $Na^+$, $K^+$, and --

Column 90, line 34, claim 18: "disodium $N^1$-((1S,3S,4S)-1-benzyl-3-[2-methyl-1-(phos-" to read as
-- disodium $N^1$-((1S,3S,4S)-1-benzyl-3-[2-methyl-1-(phos- --

Column 91, line 10, claim 23: "$M_3$ is selected from the group consisting of $Na^+$, $K^+$, and" to read as
-- $M_a$ is selected from the group consisting of $Na^+$, $K^+$, and --

Column 91, line 52, claim 27: "acetyl]amino}-2-phenylethyl)-3-{[2.5)-3-methyl-2-" to read as
-- acetyl]amino}-2-phenylethyl)-3-{[2S)-3-methyl-2- --

Column 91, line 66, claim 29: "the compound of claim us disodium $N^1$-((1S,3S,4S)-1-ben-" to read as
-- the compound of claim 1 is disodium $N^1$-((1S,3S,4S)-1-ben- --

Column 92, line 54, claim 37: "sisting of 5-1360, zintevir (AR-177), L-870812, and" to read as
-- sisting of S-1360, zintevir (AR-177), L-870812, and--

Column 93, line 10, claim 41: "the compound of claim 1 is disodium 1-[((1S,3S)-1-((1S)-1-" to read as
-- the compound of claim 1 is disodium 1-[((1S,3S)-1-((1S)-1- --

Signed and Sealed this
Nineteenth Day of April, 2011

David J. Kappos
*Director of the United States Patent and Trademark Office*